US009844541B2

(12) United States Patent
Strasswimmer et al.

(10) Patent No.: US 9,844,541 B2
(45) Date of Patent: Dec. 19, 2017

(54) METHODS OF MODULATING FOLLICLE STIMULATING HORMONE ACTIVITY

(71) Applicant: Strasspharma LLC, Delray Beach, FL (US)

(72) Inventors: John Strasswimmer, Delray Beach, FL (US); Steven Ory, Coral Springs, FL (US)

(73) Assignee: Strasspharma, LLC, Delray Beach, FL (US)

( * ) Notice: Subject to any disclaimer, the term of this patent is extended or adjusted under 35 U.S.C. 154(b) by 0 days.

(21) Appl. No.: 14/648,300

(22) PCT Filed: Nov. 27, 2013

(86) PCT No.: PCT/US2013/072131
§ 371 (c)(1),
(2) Date: May 29, 2015

(87) PCT Pub. No.: WO2014/085523
PCT Pub. Date: Jun. 5, 2014

(65) Prior Publication Data
US 2015/0297575 A1     Oct. 22, 2015

Related U.S. Application Data

(60) Provisional application No. 61/731,343, filed on Nov. 29, 2012.

(51) Int. Cl.
*A61K 31/4418* (2006.01)
*G01N 33/68* (2006.01)

(52) U.S. Cl.
CPC ....... *A61K 31/4418* (2013.01); *G01N 33/689* (2013.01); *G01N 2800/36* (2013.01)

(58) Field of Classification Search
None
See application file for complete search history.

(56) References Cited

U.S. PATENT DOCUMENTS

| | | | |
|---|---|---|---|
| 6,277,566 | B1 | 8/2001 | Beachy et al. |
| 6,432,970 | B2 | 8/2002 | Beachy et al. |
| 7,230,004 | B2 | 6/2007 | Adams et al. |
| 7,888,364 | B2 | 2/2011 | Gunzner et al. |
| 2002/0006931 | A1 | 1/2002 | Beachy et al. |
| 2007/0021493 | A1 | 1/2007 | Guicherit et al. |
| 2007/0060546 | A1 | 3/2007 | Ruat et al. |
| 2008/0287420 | A1 | 11/2008 | Castro et al. |
| 2008/0293754 | A1 | 11/2008 | Austad et al. |
| 2008/0293755 | A1 | 11/2008 | Castro et al. |

FOREIGN PATENT DOCUMENTS

| | | | |
|---|---|---|---|
| WO | WO-01/019800 A2 | 3/2001 | |
| WO | WO-01/026644 A2 | 4/2001 | |
| WO | WO-01/027135 A2 | 4/2001 | |
| WO | WO-01/049279 A2 | 7/2001 | |
| WO | WO-01/074344 A2 | 10/2001 | |
| WO | WO-01/98344 A2 | 12/2001 | |
| WO | WO-03/0011219 A2 | 2/2003 | |
| WO | WO-03/0088970 A2 | 10/2003 | |
| WO | WO-2004/020599 A2 | 3/2004 | |
| WO | WO-2005/013800 A2 | 2/2005 | |
| WO | WO-2005/032343 A2 | 4/2005 | |
| WO | WO-2005/033288 A2 | 4/2005 | |
| WO | WO-2005/042700 A2 | 5/2005 | |
| WO | WO-2006/028958 A2 | 3/2006 | |
| WO | WO-2006/050351 A2 | 5/2006 | |
| WO | WO-2006/078283 A2 | 7/2006 | |
| WO | WO-2007/054623 A2 | 5/2007 | |
| WO | WO-2007/059157 A1 | 5/2007 | |
| WO | WO-2007/120827 A2 | 10/2007 | |
| WO | WO-2007/126455 A2 | 11/2007 | |
| WO | WO-2007/131201 A2 | 11/2007 | |
| WO | WO-2008/070357 A2 | 6/2008 | |
| WO | WO-2008/110611 A1 | 9/2008 | |
| WO | WO-2008/112913 A1 | 9/2008 | |
| WO | WO-2008/131354 A2 | 10/2008 | |

OTHER PUBLICATIONS

Aad, P.Y. et al., The Hedgehog System in Ovarian Follicles of Cattle Selected for Twin Ovulations and Births: Evidence of a Link Between the IGF and Hedgehog Systems, Biology of Reproduction, 87(4): Article 79, 10 pages (2012).

Alcedo, J. et al., The Drosophila smoothened Gene ncodes a Seven-Pass Membrane Protein, a Putative Receptor for the Hedgehog Signal, Cell 86(2): 221-232 (1996).

Allen, B.L. et al., Overlapping roles and collective requirement for the coreceptors Gas1, Cdo and Boc in Shh pathway function, Dev. Cell 20(6): 775-787 (2011).

Bai, C.B. et al., All mouse ventral spinal cord patterning by hedgehog is Gli dependent and involves an activator function of Gli3, Dev. Cell, 6(1): 103-115 (2004).

Bale, A.E. And Yu, K.P., The hedgehog pathway and basal cell carcinomas, Hum. Mol. Genet., 10(7): 757-762 (2001).

Beachy, P.A. et al., Interactions between Hedgehog proteins and their binding partners come into view, Genes Dev., 24(18):2001-2012 (2010).

Chen, J.K. et al., Inhibition of Hedgehog signaling by direct binding of cyclopamine to Smoothened, Genes Devel. 16(21): 2743-2748 (2002).

Chen, J.K. et al., Small molecule modulation of Smoothened activity, Proc. Natl. Acad. Sci. USA, 99(22): 14071-14076 (2002).

Chen, M.H. et al., Mice deficient in the fused homolog do not exhibit phenotypes indicative of perturbed hedgehog signaling during embryonic development, Mol. Cell. Biol., 25(16): 7042-7053 (2005).

Dai, P. et al., Sonic Hedgehog-induced activation of the Gli1 promoter is mediated by GLI3, J. Biol. Chem., 274(12): 8143-8152 (1999).

Erivedge, Highlights of Prescribing Information, 17 pages (Jan. 2012).

(Continued)

Primary Examiner — Samantha Shterengarts
(74) Attorney, Agent, or Firm — Choate, Hall & Stewart LLP; Brenda Herschbach Jarrell; Rolando Medina

(57) ABSTRACT

Hedgehog pathway modulators, such as hedgehog pathway activators or inhibitors, and the use of such modulators to modulate FSH signaling are described.

19 Claims, No Drawings

(56) References Cited

OTHER PUBLICATIONS

Forbes, A. et al., hedgehog is required for the proliferation and specification of ovarian somatic cells prior to egg chamber formation in Drosophila, Development, 122:1125-1135 (1996).

Genentech, Inc., Erivedge (vismodegib), Highlights of Prescribing Information, 19 pages (2012). URL: http://www.accessdata.fda.gov/drugsatfda_docs/label/2012/2033881bl.pdf> [Retrieved Mar. 3, 2013].

International Search Report for PCT/US2013/072131, 3 pages dated Mar. 28, 2014.

Kettel, L. et al., Endocrine responses to long-term administration of the antiprogesterone RU486 in patients with pelvic endometriosis, Fertility and Sterility, 56(3):402-407 (1991).

Kinzler, K.W. et al., Identification of an amplified, highly expressed gene in a human glioma, Science, 236(4797): 70-73 (1987).

Liu, H. et al., Clinical implications of hedgehog signaling pathway inhibitors, Chinese Journal of Cancer, 30(1): 13-26 (2011).

Lucas, B.S. et al., Design of 1-piperazinyl-4-arylphthalazines as potent Smoothened antagonists, Bioorg. Med. Chem. Lett., 20(12): 3618-22 (2010).

Lum, L. et al., The Hedgehog response network: sensors, switches, and routers, Science, 304(5678): 1755-1759 (2004).

Matise, M.P. and Joyner, A.L., Gli genes in development and cancer, Oncogene 18(55): 7852-7859 (1999).

Methot, N. and Basler, K., Suppressor of fused opposes hedgehog signal transduction by impeding nuclear accumulation of the activator form of Cubitus interruptus, Development, 127(18): 4001-4010 (2000).

Motoyama, J. et al, Differential requirement for Gli2 and Gli3 in ventral neural cell fate specification, Dev. Biol., 259(1): 150-161 (2003).

Murphy, A.A. et al., Regression of Uterine Leiomyomata in Response to the Antiprogesterone RU 486, Journal of Clinical Endocrinology and Metabolism, 76 (2): 513-517 (1993).

National Institute of Health Clinical Trial Identifier No. NCT00670189 (Apr. 29, 2008).

National Institute of Health Clinical Trial Identifier No. NCT00953758 (Aug. 4, 2009).

National Institute of Health Clinical Trial Identifier No. NCT01106508 (Apr. 16, 2010).

Pan, S. et al., Discovery of NVP-LDE225, a Potent and Selective Smoothened Antagonist, ACS Med. Chem. Lett., 1(3): 130-134 (2010).

Preat, T., Characterization of Suppressor of fused, a complete suppressor of the fused segment polarity gene of Drosophila melanogaster, Genetics, 132(3): 725-736 (1992).

Roche Pharma: ERIVEDGE(R) Capsules (150 mg) Material Safety Data Sheet, Retrieved from the Internet: http://ww.gene.com/download/pdf/ErivedgeMSDS.pdf (Jul. 20, 2012).

Sekulic, A. et al., Efficacy and Safety of Vismodegib in Advanced Basal-Cell Carcinoma, N. Engl. J. Med., 366(23): 2171-2179 (2012).

Siu, L.L. et al., a first-in-human, phase I study of an oral hedgehog (HH) pathway antagonist, BMS-833923 (XL139), in subjects with advanced or metastatic solid tumors, J. Clin. Oncol., 28(15 suppl): 2501 (2010). URL: <http://meeting.ascopubs.org/cgi/content/abstract/28/15_suppl/2501> [Retrieved Jun. 28, 2016].

Strasswimmer, J. et al., Amenorrhea secondary to a vismodegib-induced blockade of follicle-stimulating hormone-receptor activat, Fertility and Sterility, 102(2):555-557 (2014).

Written Opinion for PCT/US2013/072131, 12 pages dated Mar. 28, 2014.

Zhu, A.J. et al., Altered localization of Drosophila Smoothened protein activates Hedgehog signal transduction, Genes Dev., 17(10):1240-1252 (2003).

METHODS OF MODULATING FOLLICLE STIMULATING HORMONE ACTIVITY

CROSS REFERENCE TO RELATED APPLICATIONS

The present application claims the benefit of U.S. provisional application Ser. No. 61/731,343, filed on Nov. 29, 2012, the contents of which are herein incorporated by reference in their entirety.

SEQUENCE LISTING

In accordance with 37 CFR §1.52(e)(5), the present specification makes reference to a Sequence Listing (submitted electronically as a .txt file named "2010560_0006_SL.TXT"). The .txt file was generated on Aug. 7, 2017, and is 164,857 bytes in size. The entire contents of the Sequence Listing are herein incorporated by reference.

BACKGROUND

The gonadotropin Follicle Stimulating Hormone (FSH) is released from the anterior pituitary under the influence of gonadotropin-releasing hormone and estrogens, and from the placenta during pregnancy. In the female, FSH acts on the ovaries promoting development of follicles and is the major hormone regulating secretion of estrogens. In the male, FSH is responsible for the integrity of the seminiferous tubules and acts on Sertoli cells to support gametogenesis. The actions of the FSH hormone are mediated by a specific plasma membrane receptor that is a member of the large family of G-protein coupled receptors. Modulation of FSH signaling can affect reproductive functions in both females and males.

SUMMARY OF THE INVENTION

The present disclosure encompasses the discovery that the Hedgehog (Hh) pathway is involved in signaling through the FSH receptor. Specifically, the present disclosure encompasses the discovery that inhibition of the Hh pathway inhibits FSH binding to the FSH receptor. The present disclosure therefore provides hedgehog pathway modulators (e.g., activators or inhibitors) for use in medicine, and specifically in treatment and/or prevention (e.g., delay of onset) of certain disorders, e.g., gynecologic disorders.

Definitions

In order for the present invention to be more readily understood, certain terms are first defined below. Additional definitions for the following terms and other terms are set forth throughout the specification.

Combination therapy: The term "combination therapy", as used herein, refers to those situations in which two or more different pharmaceutical agents are administered in overlapping regimens so that the subject is simultaneously exposed to both agents. When used in combination therapy, two or more different agents may be administered simultaneously or separately. This administration in combination can include simultaneous administration of the two or more agents in the same dosage form, simultaneous administration in separate dosage forms, and separate administration. That is, two or more agents can be formulated together in the same dosage form and administered simultaneously. Alternatively, two or more agents can be simultaneously administered, wherein the agents are present in separate formulations. In another alternative, a first agent can be administered just followed by one or more additional agents. In the separate administration protocol, two or more agents may be administered a few minutes apart, or a few hours apart, or a few days apart.

Characteristic portion: As used herein, the term a "characteristic portion" of a substance, in the broadest sense, is one that shares some degree of sequence or structural identity with respect to the whole substance. In certain embodiments, a characteristic portion shares at least one functional characteristic with the intact substance. For example, a "characteristic portion" of a polypeptide or protein is one that contains a continuous stretch of amino acids, or a collection of continuous stretches of amino acids, that together are characteristic of a polypeptide or protein. In some embodiments, each such continuous stretch generally contains at least 2, 5, 10, 15, 20, 50, or more amino acids. In general, a characteristic portion of a substance (e.g., of a polypeptide or protein) is one that, in addition to the sequence and/or structural identity specified above, shares at least one functional characteristic with the relevant intact substance. In some embodiments, a characteristic portion may be biologically active.

Characteristic sequence: A "characteristic sequence" is a sequence that is found in all members of a family of polypeptides or nucleic acids, and therefore can be used by those of ordinary skill in the art to define members of the family.

Hedgehog pathway: As used herein, the terms "hedgehog pathway" and "hedgehog signaling pathway" are used interchangeably and refer to a chain of events (or a subset of events) normally mediated by binding of an Hh polypeptide to an appropriate receptor, such as a Ptc polypeptide. Hh pathway activation transmits an Hh signal in cells and/or tissues. In some embodiments, Hh pathway activation results in changes in degree of downstream gene expression level and/or phenotypic changes.

Hedgehog pathway activator: The term "hedgehog pathway activator", as used herein, refers to any substance that activates or increases the activity of an Hh signaling pathway. In some embodiments, an Hh pathway activator is an Hh polypeptide, a Cdo polypeptide, a Boc polypeptide, a Gas1 polypeptide, an Smo polypeptide, a Gli polypeptide, and/or a nucleic acid encoding such polypeptide. In some embodiments, an Hh pathway activator is a substance that activates the transcription, binding, activity or stability of an Hh polypeptide, a Cdo polypeptide, a Boc polypeptide, a Gas1 polypeptide, an Smo polypeptide, a Gli polypeptide, and/or a nucleic acid encoding such polypeptide. In some embodiments, an Hh pathway activator is a substance that inhibits the transcription, binding, activity or stability of a Ptc polypeptide, an Hhip polypeptide, an SuFu polypeptide, and/or a nucleic acid encoding such polypeptide.

Hedgehog pathway inhibitor: The term "hedgehog pathway inhibitor", as used herein, refers to any substance that inhibits or reduces the activity of an Hh signaling pathway. In some embodiments, an Hh pathway inhibitor is a Ptc polypeptide, an Hhip polypeptide, an SuFu polypeptide, and/or a nucleic acid encoding such polypeptide. In some embodiments, an Hh pathway inhibitor is a substance that inhibits the transcription, binding, activity or stability of an Hh polypeptide, a Cdo polypeptide, a Boc polypeptide, a Gas1 polypeptide, an Smo polypeptide, a Gli polypeptide, and/or a nucleic acid encoding such polypeptide. In some embodiments, an Hh pathway inhibitor is a substance that activates the transcription, binding, activity or stability of a Ptc polypeptide, an Hhip polypeptide, an SuFu polypeptide, and/or a nucleic acid encoding such polypeptide.

Hedgehog (Hh) pathway modulator: The term "hedgehog pathway modulator", as used herein, refers to any substance that modulates activity of an Hh pathway. In some embodiments, a hedgehog pathway modulator modulates the transcription, binding, activity and/or stability of an Hh pathway polypeptide and/or a nucleic acid encoding such polypeptide. In some embodiments, an Hh pathway modulator is an Hh pathway activator. In some embodiments, an Hh pathway modulator is an Hh pathway inhibitor.

Hedgehog (Hh) pathway polypeptide: As used herein, the term "hedgehog pathway polypeptide" refers to a polypeptide whose amino acid sequence includes at least one characteristic sequence of and/or shows at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, or 70% identity with a protein involved in a Hh pathway (e.g., Boc, Cdo, Gas1, Gli, Hh, Hhip, Ptc, Smo, or SuFu polypeptide). A wide variety of Hh pathway sequences from flies, vertebrates, and mammals are known in the art, such as those described herein; in some embodiments, an Hh pathway polypeptide shares at least one characteristic sequence of and/or shows the specified degree of overall sequence identity with one of the Boc, Cdo, Gas1, Gli, Hh, Hhip, Ptc, Smo, or SuFu sequences set forth herein (each of which may be considered a "reference" Hh pathway polypeptide). In some embodiments, an Hh pathway polypeptide as described herein shares at least one biological activity with a reference Hh pathway polypeptide as set forth herein. In some such embodiments, the shared biological activity relates to Hh signaling pathway activation or inhibition.

Hedgehog (Hh) polypeptide: As used herein, the term "hedgehog polypeptide" (or "Hh polypeptide") refers to a polypeptide whose amino acid sequence includes at least one characteristic sequence of and/or shows at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, or 70% identity with a hedgehog polypeptide (e.g., Desert (Dhh), Sonic (Shh) or Indian (Ihh)). A wide variety of Hh sequences from flies, vertebrates, and mammals are known in the art, such as those described herein; in some embodiments, a Hh polypeptide shares at least one characteristic sequence of and/or shows the specified degree of overall sequence identity with one of the Dhh, Shh, or Ihh sequences set forth herein (each of which may be considered a "reference" Hh polypeptide). In some embodiments, an Hh polypeptide as described herein shares at least one biological activity with a reference Hh polypeptide as set forth herein. In some such embodiments, the shared biological activity relates to Hh signaling pathway activation.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Identity: As used herein, the term "identity" refers to the overall relatedness between polymeric molecules, e.g., between nucleic acid molecules (e.g., DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0) using a PAM 120 weight residue table, a gap length penalty of 12 and a gap penalty of 4. The percent identity between two nucleotide sequences can, alternatively, be determined using the GAP program in the GCG software package using an NWSgapdna.CMP matrix.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids.

Reference sample: As used herein, a reference sample may include, but is not limited to, any or all of the following: a cell or cells, a portion of tissue, blood, serum, ascites, urine, saliva, and other body fluids, secretions, or excretions. The term "sample" also includes any material derived by processing such a sample. Derived samples may include nucleotide molecules or polypeptides extracted from the sample or obtained by subjecting the sample to techniques such as amplification or reverse transcription of mRNA, etc.

Subject: As used herein, the term "subject" or "patient" refers to any organism upon which embodiments of the invention may be used or administered, e.g., for experimental, diagnostic, prophylactic, and/or therapeutic purposes. Typical subjects include animals (e.g., mammals such as mice, rats, rabbits, non-human primates, and humans; insects; worms; etc.).

Suffering from: An individual who is "suffering from" a disease, disorder, or condition (e.g., a gynecologic condition) has been diagnosed with and/or exhibits one or more symptoms of the disease, disorder, or condition. In some embodiments, an individual who is suffering from gynecologic condition has a gynecologic condition, but does not display any symptoms of a gynecologic condition and/or has not been diagnosed with a gynecologic condition.

Susceptible to: An individual who is "susceptible to" a disease, disorder, or condition (e.g., a gynecologic condition) is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who displays conditions associated with development of the disease, disorder, or condition. In some embodiments, a risk of developing a disease, disorder, and/or condition is a population-based risk.

Symptoms are reduced: According to the present invention, "symptoms are reduced" when one or more symptoms of a particular disease, disorder or condition is reduced in magnitude (e.g., intensity, severity, etc.) or frequency. For purposes of clarity, a delay in the onset of a particular symptom is considered one form of reducing the frequency of that symptom. It is not intended that the present invention be limited only to cases where the symptoms are eliminated. The present invention specifically contemplates treatment such that one or more symptoms is/are reduced (and the condition of the subject is thereby "improved"), albeit not completely eliminated.

Target cell or target tissue: As used herein, the terms "target cell" or "target tissue" refer to any cell, tissue, or organism that is affected by a condition described herein and to be treated, or any cell, tissue, or organism in which a protein involved in a condition described herein is expressed. In some embodiments, target cells, target tissues, or target organisms include those cells, tissues, or organisms in which there is a detectable or abnormally high amount of FSH signaling (e.g., comparable to that observed in subjects suffering from or susceptible to a gynecologic condition). In some embodiments, target cells, target tissues, or target organisms include those cells, tissues or organisms that display a disease-associated pathology, symptom, or feature.

Therapeutic regimen: As used herein, the term "therapeutic regimen" refers to any method used to partially or completely alleviate, ameliorate, relieve, inhibit, prevent, delay onset of, reduce severity of and/or reduce incidence of one or more symptoms or features of a particular disease, disorder, and/or condition. It may include a treatment or series of treatments designed to achieve a particular effect, e.g., reduction or elimination of a detrimental condition or disease such as a gynecologic disorder. The treatment may include administration of one or more compounds either simultaneously, sequentially or at different times, for the same or different amounts of time. Alternatively, or additionally, the treatment may include exposure to radiation, chemotherapeutic agents, hormone therapy, or surgery. In addition, a "treatment regimen" may include genetic methods such as gene therapy, gene ablation or other methods known to reduce expression of a particular gene or translation of a gene-derived mRNA.

Therapeutic agent: As used herein, the phrase "therapeutic agent" refers to any agent that, when administered to a subject, has a therapeutic effect and/or elicits a desired biological and/or pharmacological effect.

Therapeutically effective amount: As used herein, the term "therapeutically effective amount" refers to an amount of an agent (e.g., a hedgehog modulator) that confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic agent or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic agent, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the subject; the time of administration, route of administration, and/or rate of excretion or metabolism of the specific fusion protein employed; the duration of the treatment; and like factors as is well known in the medical arts.

Treatment: As used herein, the term "treatment" (also "treat" or "treating") refers to any administration of a substance (e.g., provided compositions) that partially or completely alleviates, ameliorates, relieves, inhibits, delays onset of, reduces severity of, and/or reduces incidence of one or more symptoms, features, and/or causes of a particular disease, disorder, and/or condition (e.g., a gynecologic disorder). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

DETAILED DESCRIPTION

The present disclosure encompasses the surprising discovery that FSH activity can be modulated using hedgehog pathway modulators (e.g., hedgehog pathway activators or inhibitors). Accordingly, the disclosure provides, among other things, use of the hedgehog pathway as a diagnostic, prognostic and/or therapeutic target for modulating FSH activity, e.g., for gynecologic disorders.

Hedgehog Pathway

The hedgehog (Hh) pathway is well known (see, e.g., U.S. Pat. No. 6,277,566 B1; U.S. Pat. No. 6,432,970 B2; Lum et al., Science 304:1755-1759 (2004); and Bale et al., Hum. Mol. Genet. 10:757-762 (2001)). During growth, human cells need to communicate to neighboring cells whether it is time to divide or stop dividing. The Hh signaling pathway is a key regulator of this messaging.

The vertebrate family of Hh genes includes three members that exist in mammals, known as Desert (Dhh), Sonic (Shh) and Indian (Ihh) Hedgehogs, all of which encode secreted proteins. These various Hh proteins consist of a signal peptide, a highly conserved N-terminal region, and a more divergent C-terminal domain. Biochemical studies have shown that autoproteolytic cleavage of the Hh precursor protein proceeds through an internal thioester intermediate which subsequently is cleaved in a nucleophilic substitution. It is likely that the nucleophile is a small lipophilic molecule that becomes covalently bound to the C-terminal end of the N-peptide, tethering it to the cell surface. As a result of the tethering, a high local concentration of N-terminal Hh peptide is generated on the surface of Hh producing cells. It is this N-terminal peptide which is both necessary and sufficient for short- and long-range Hh signaling activities.

Smoothened (Smo) encodes a transmembrane protein of 1024 amino acids, which acts as a transducer of the Hh signal. Smo protein has 7 hydrophobic membrane-spanning domains, an extracellular amino-terminal region, and an intracellular carboxy-terminal region. Smo bears some similarity to G protein-coupled receptors and is most homologous to the Frizzled (Fz) family of serpentine proteins (Alcedo et al., Cell 86: 221 (1996)).

In an inactive Hh signaling pathway, the transmembrane protein receptor Patched (Ptc) inhibits the stabilization, phosphorylation, and/or activity of Smoothened (Smo). Activation of the pathway is initiated through binding of Hh polypeptide to Ptc. Hh binding to Ptc alters the interaction of Smo and Ptc, reversing the repression of Smo by Ptc (see Zhu et al., Genes Dev. 17:1240 (2003)).

Smo activation initiates a cascade that leads to the translocation of an active form of the transcription factor Gli to the nucleus of the cell. Three Gli proteins known in vertebrates are Gli1, Gli2 and Gli3 (Kinzler et al., Science 236:70-73 (1987); Bai et al, Dev. Cell 6:103-115 (2004); Motoyama et al, Dev. Biol. 259:150-161 (2003)). Gli proteins share high homology in the zinc finger domain, but have limited homology outside of this region (Matise et al., Oncogene 18:7852-7859 (1999)). Gli1 is a transcriptional activator, while Gli2 and Gli3 are bifunctional and can function as a transcriptional activator or, when proteolytically processed, a transcriptional repressor (Dai et al., J. Biol. Chem. 12:8143-8152 (1999)). In the inactive Hh pathway, Gli is prevented from entering the nucleus through interactions with cytoplasmic proteins, including Fused (Fu) and Suppressor of fused (Sufu) (see Methot et al., Dev. 127:4001-4010 (2000)); Chen et al., Mol. Cell. Biol. 25:7042-7053 (2005)); Preat, Genetics 132:725-736 (1992)). As a consequence, transcriptional activation of Hh target genes is repressed. The activation of Smo leads to translocation of Gli to the nucleus, which activates Hh pathway target gene expression, including of Wnts, TGF-beta, and Ptc and Gli themselves.

Additional Hh pathway proteins include Gas1, Cdo, and Boc, which promote Hh pathway signaling (see Allen et al., Dev. Cell 20:775-787 (2011)), and Hhip, which inhibits Hh pathway signaling (see Beachy et al., Genes Dev. 24:2001-2012 (2010)).

The Hh pathway is best studied in cell proliferation and differentiation during embryo development. While the Hh pathway is thought to be inactive in most normal adult tissues, it appears to be active in two areas: hair follicles and taste papillae of the tongue. In addition, Hh pathway polypeptides are identified in some areas of adult gastrointestinal tract, but their function is unclear. There is no published evidence implicating the Hh pathway in the reproductive tract physiology or reproduction.

When cellular division occurs uncontrolled, cancer appears. Hh pathway activation has been well documented in the pathogenesis of Basal Cell Carcinoma (BCC). This activation can occur at several levels in the signaling pathway, most commonly in patched (Ptc) or smoothened (Smo) gene products. Patients with BCC are usually treated with surgical, topical, or radiotherapy techniques. In situations where BCC has metastasized or become locally advanced to the point where traditional options are not optimal, oral therapy with an inhibitor of the Hh pathway is an option. Vismodegib (Erivedge™, Genentech, Inc., San Francisco, Calif.) is approved for this situation. Vismodegib binds to Smo, preventing further downstream signaling and preventing cell division. Major side effects include dysgeusia, alopecia, leg cramping, and gastrointestinal disturbances.

Nucleic Acids Encoding Hedgehog Pathway Polypeptides

Methods and compositions described herein include, for example, modulators of a hedgehog signaling pathway (e.g., modulators of one or more Hh pathway polypeptides). Nucleic acids encoding Hh pathway polypeptides (e.g., Boc, Cdo, Gas1, Gli, Hh, Hhip, Ptc, Smo, or SuFu) are known. According to the present disclosure, modulators of such nucleic acids (and polypeptides) are useful in the treatment of gynecologic disorders. In some embodiments, such nucleic acids have or include nucleotide sequences as set forth in SEQ ID NO:1, 3, 5, 7, 9, 11, 13, 15, 17, 19, 21, 23, 25, or 27, or characteristic sequence elements thereof or therein. In some embodiments, useful nucleic acids show at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, or 70% overall sequence identity with one or more of SEQ ID NO:1, 3, 5, 7, 9, 11, 13, 15, 17, 19, 21, 23, 25, or 27. Alternatively or additionally, in some embodiments, useful nucleic acids include at least 5, 6, 7, 8, 9, 10, 11, 12, 13, 14, 15, 16, 17, 18, 19, 20, 21, 22, 23, 24, 25 or more contiguous residues found in SEQ ID NO:1, 3, 5, 7, 9, 11, 13, 15, 17, 19, 21, 23, 25, or 27. In some embodiments, useful nucleic acids are generated in vitro; in some embodiments, useful nucleic acids are generated in vivo. In some embodiments, useful nucleic acids are generated using genetic engineering techniques (e.g., for production and/or mutagenesis of a reference sequence). To give but a few examples, in some embodiments, nucleic acid variants (e.g., of SEQ ID NO:1, 3, 5, 7, 9, 11, 13, 15, 17, 19, 21, 23, 25, or 27) are generated using techniques such as site directed mutagenesis, random chemical mutagenesis, Exonuclease III deletion procedures, and standard cloning techniques. In some embodiments, useful nucleic acids are generating using chemical synthesis and/or modification procedures.

A variety of methods of making nucleic acids that are "variants" with respect to a reference nucleic acid (e.g., a naturally-occurring or other reference nucleic acid) are well known in the art. These include, for example, procedures in which nucleic acid sequences obtained from natural isolates are modified to generate nucleic acids that encode polypeptides having characteristics that enhance their value in industrial or laboratory applications. In such some embodiments of such procedures, a large number of variant sequences having one or more nucleotide differences with respect to the sequence obtained from the natural isolate are generated and characterized. Typically, these nucleotide differences result in amino acid changes with respect to the polypeptides encoded by the nucleic acids from the natural isolates.

For example, variants can be created using error prone PCR (see, e.g., Leung et al., Technique 1:11-15, 1989; and Caldwell et al., PCR Methods Applic. 2:28-33, 1992). In error prone PCR, PCR is performed under conditions where the copying fidelity of the DNA polymerase is low, such that a high rate of point mutations is obtained along the entire length of the PCR product. Briefly, in such procedures, nucleic acids to be mutagenized are mixed with PCR primers, reaction buffer, $MgCl_2$, $MnCl_2$, Taq polymerase, and an appropriate concentration of dNTPs for achieving a high rate of point mutation along the entire length of the PCR product. For example, the reaction can be performed using 20 fmoles of nucleic acid to be mutagenized, 30 pmole of each PCR primer, a reaction buffer comprising 50 mM KCl, 10 mM Tris HCl (pH 8.3), and 0.01% gelatin, 7 mM $MgCl_2$, 0.5 mM $MnCl_2$, 5 units of Taq polymerase, 0.2 mM dGTP, 0.2 mM dATP, 1 mM dCTP, and 1 mM dTTP. PCR can be performed for 30 cycles of 94° C. for 1 min, 45° C. for 1 min, and 72° C. for 1 min. However, it will be appreciated that these parameters can be varied as appropriate. The mutagenized nucleic acids are then cloned into an appropriate vector and the activities of the polypeptides encoded by the mutagenized nucleic acids are evaluated.

Variants can also be created using oligonucleotide directed mutagenesis to generate site-specific mutations in any cloned DNA of interest. Oligonucleotide mutagenesis is described in, for example, Reidhaar-Olson et al., Science 241:53-57 (1988). Briefly, in such procedures a plurality of double stranded oligonucleotides bearing one or more mutations to be introduced into the cloned DNA are synthesized and inserted into the cloned DNA to be mutagenized. Clones containing the mutagenized DNA are recovered, and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in, for example, U.S. Pat. No. 5,965,408. Still another method of generating variants is sexual PCR mutagenesis. In sexual PCR mutagenesis, forced homologous recombination occurs between DNA molecules of different, but highly related, DNA sequence in vitro as a result of random fragmentation of the DNA molecule based on sequence homology. This is followed by fixation of the crossover by primer extension in a PCR reaction. Sexual PCR mutagenesis is described in, for example, Stemmer, Proc. Natl. Acad. Sci., USA 91:10747-10751 (1994).

Variants can also be created by in vivo mutagenesis. In some embodiments, random mutations in a nucleic acid sequence are generated by propagating the sequence in a bacterial strain, such as an E. coli strain, which carries mutations in one or more of the DNA repair pathways. Such "mutator" strains have a higher random mutation rate than that of a wild-type strain. Propagating a DNA sequence in one of these strains will generate random mutations within the DNA. Mutator strains suitable for use for in vivo mutagenesis are described in, for example, PCT Publication No. WO 91/16427.

Variants can also be generated using cassette mutagenesis. In cassette mutagenesis, a small region of a double stranded DNA molecule is replaced with a synthetic oligonucleotide "cassette" that differs from the native sequence. The oligonucleotide often contains a completely and/or partially randomized native sequence. Recursive ensemble mutagenesis can also be used to generate variants. Recursive ensemble mutagenesis is an algorithm for protein engineering (i.e., protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described in, for example, Arkin et al., Proc. Natl. Acad. Sci., USA 89:7811-7815 (1992).

In some embodiments, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described in, for example, Delegrave et al., Biotech. Res. 11:1548-1552 (1993). Random and site-directed mutagenesis are described in, for example, Arnold, Curr. Opin. Biotech. 4:450-455 (1993). In some embodiments, variants are created using shuffling procedures wherein portions of a plurality of nucleic acids that encode distinct polypeptides are fused together to create chimeric nucleic acid sequences that encode chimeric polypeptides as described in, for example, U.S. Pat. Nos. 5,965,408 and 5,939,250.

In some embodiments, nucleic acids for use in accordance with the present disclosure comprise naturally-occurring nucleotide residues. In some embodiments, nucleic acids for use in accordance with the present disclosure include one or more nucleotide "analogs". A nucleotide analog is a nucleotide (i.e., an entity that is incorporated into a nucleic acid polymer without significantly disrupting the structure and/or function of that polymer) whose chemical structure differs from that of reference naturally-occurring ribonucleic or deoxyribonucleic acid residues adenine, guanine, cytosine, thymine, and uracil. In some embodiments, a nucleotide analog differs from its reference nucleotide at the base moiety, sugar moiety, and/or phosphate backbone. In some embodiments, a nucleotide analog contributes to one or more altered features in a nucleic acid polymer into which it is incorporated as compared with a comparable nucleic acid polymer containing its reference nucleotide rather than the analog. For example, in some embodiments, such analog-containing polymer shows improved, stability, hybridization, and/or solubility.

In some embodiments, base moiety alterations found in nucleotide analogs include deoxyuridine for deoxythymidine and 5-methyl-2'-deoxycytidine or 5-bromo-2'-deoxycytidine for deoxycytidine. In some embodiments, sugar moiety alterations found in nucleotide analogs include modification of the 2' hydroxyl of the ribose sugar to form 2'-O-methyl or 2'-O-allyl sugars. In some embodiments, deoxyribose phosphate backbone alterations found in nucleotide analogs include morpholino nucleic acids, in which each base moiety is linked to a six-membered, morpholino ring, or peptide nucleic acids, in which the deoxyphosphate backbone is replaced by a pseudopeptide backbone and the four bases are retained (see, e.g., Summerton et al., Antisense Nucleic Acid Drug Dev. 7:187-195 (1997); Hyrup et al., Bioorgan. Med. Chem. 4:5-23(1996)). Alternatively or additionally, nucleotide analogs may have a phosphorothioate or phosphorodithioate backbone, a phosphoroamidite, or an alkyl phosphotriester backbone.

In certain instances, a Hh pathway polynucleotide or variant for use in accordance with the present disclosure includes alterations to codon(s) to optimize for expression in a particular host cell. For example, for expression in E. coli, a Hh pathway polynucleotide or variant can include one or more altered codons as described in, e.g., Grosjean et al., Gene 18:199-209 (1982).

Hedgehog Pathway Polypeptides

In some embodiments, methods and compositions described utilize a modulator of one or more Hh pathway polypeptides (e.g., Boc, Cdo, Gas1, Gli, Hh, Hhip, Ptc, Smo, or SuFu polypeptides). According to the present disclosure, such polypeptides are useful in the treatment of gynecologic disorders. In some embodiments, such polypeptides useful in the practice of the present disclosure have or include amino acid sequences as set forth in SEQ ID NO:2, 4, 6, 8, 10, 12, 14, 16, 18, 20, 22, 24, 26, or 28, or characteristic sequence elements thereof or therein. In some embodiments, useful polypeptides show at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, or 70% overall sequence identity with one or more of SEQ ID NO:2, 4, 6, 8, 10, 12, 14, 16, 18, 20, 22, 24, 26, or 28. Alternatively or additionally, in some embodiments, useful polypeptides include at least about 5, 10, 15, 20, 25, 30, 35, 40, 45, 50, 75, 100, or 150 or more contiguous amino acid residues found in SEQ ID NO:2, 4, 6, 8, 10, 12, 14, 16, 18, 20, 22, 24, 26, or 28.

In some embodiments, a useful polypeptide differs from its reference polypeptide (e.g., a polypeptide having or including an amino acid sequence as set forth in SEQ ID NO:2, 4, 6, 8, 10, 12, 14, 16, 18, 20, 22, 24, 26, or 28, or characteristic sequence elements thereof or therein) by one or more amino acid residues. For example, in some embodiments, the difference is a conservative or nonconservative substitution of one or more amino acid residues. Conservative substitutions are those that substitute a given amino acid in a polypeptide by another amino acid of similar characteristics. Typical conservative substitutions are the following replacements: replacement of an aliphatic amino acid, such as alanine, valine, leucine, and isoleucine, with another aliphatic amino acid; replacement of a serine with a threonine or vice versa; replacement of an acidic residue, such as aspartic acid and glutamic acid, with another acidic residue; replacement of a residue bearing an amide group, such as asparagine and glutamine, with another residue bearing an amide group; exchange of a basic residue, such as lysine and arginine, with another basic residue; and replacement of an aromatic residue, such as phenylalanine and tyrosine, with another aromatic residue.

In some embodiments, useful Hh pathway polypeptides include a substituent group on one or more amino acid residues. Still other useful polypeptides are associated with (e.g., fused, linked, or coupled to) another moiety (e.g., a peptide or molecule). For example, useful Hh pathway polypeptides can be fused, linked, or coupled to an amino acid sequence (e.g., a leader sequence, a secretory sequence, a proprotein sequence, a second polypeptide, or a sequence that facilitates purification, enrichment, or stabilization of the polypeptide). In certain other embodiments, a polypeptide includes a targeting agent, e.g., a targeting agent described herein.

A variety of methods of making polypeptides are known in the art and can be used to make Hh pathway polypeptides. For example, Hh pathway polypeptides can be recombinantly produced by utilizing a host cell system engineered to express a nucleic acid encoding a Hh pathway polypeptide (e.g., a nucleic acid described herein). Alternatively or additionally, a Hh pathway polypeptide can be produced by activating an endogenous gene (e.g., a nucleic acid encoding a Hh pathway polypeptide present endogenously in a cell). Alternatively or additionally, a Hh pathway polypeptide can be partially or fully prepared by chemical synthesis. Alternatively or additionally, a Hh pathway polypeptide can be purified from natural sources.

Where a Hh pathway polypeptide is recombinantly produced, any expression system can be used. Known expression systems include, without limitation, for example, egg, baculovirus, plant, yeast, or mammalian cells.

In some embodiments, a Hh pathway polypeptide suitable for use in methods described herein are produced in mammalian cells. Non-limiting examples of mammalian cells that can be used include BALB/c mouse myeloma line (NSO/l, ECACC No: 85110503); human retinoblasts (PER.C6, CruCell, Leiden, The Netherlands); monkey kidney CV1 line transformed by SV40 (COS-7, ATCC CRL 1651); human embryonic kidney line (293 or 293 cells subcloned for growth in suspension culture, Graham et al., J. Gen Virol., 36:59, 1977); human fibrosarcoma cell line (e.g., HT1080); baby hamster kidney cells (BHK, ATCC CCL 10); Chinese hamster ovary cells+/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2).

Hedgehog Pathway Activators

Hh pathway activators useful in the methods described herein include an Hh, Cdo, Boc, Gas1, Smo, or Gli polypeptide; a nucleic acid encoding an Hh, Cdo, Boc, Gas1, Smo, or Gli polypeptide; any substance that increases level and/or activity of an Hh, Cdo, Boc, Gas1, Smo, or Gli polypeptide; any substance that increases level and/or activity of a nucleic acid encoding a Cdo, Boc, Gas1, Smo, or Gli polypeptide; any substance that decreases level or activity of a Ptc, Hhip, and/or SuFu polypeptide; and/or any substance that decreases level or activity of a nucleic acid encoding a Ptc, Hhip, and/or SuFu polypeptide.

In some embodiments, an Hh pathway activator is or includes an Hh, Cdo, Boc, Gas1, Smo, and/or Gli polypeptide having an activating mutation (e.g., a difference of one or more amino acid residues relative to a reference Hh, Cdo, Boc, Gas1, Smo, and/or Gli polypeptide and a higher level of expression and/or activity as compared to such reference polypeptide). In some embodiments, an Hh pathway activator is or includes a Ptc, Hhip, and/or SuFu polypeptide having an inhibiting mutation (e.g., a difference of one or more amino acid residues relative to a reference Ptc, Hhip, and/or SuFu polypeptide and having a lower level of expression and/or activity as compared to such reference polypeptide).

Hedgehog Pathway Inhibitors

Hh pathway inhibitors useful in the methods described herein include a Ptc, Hhip, or SuFu polypeptide; a nucleic acid encoding a Ptc, Hhip, or SuFu polypeptide; any substance that increases level and/or activity of a Ptc, Hhip, and/or SuFu polypeptide, any substance that increases level and/or activity of a nucleic acid encoding a Ptc, Hhip, and/or SuFu polypeptide; any substance that decreases level or activity of an Hh, Cdo, Boc, Gas1, Smo, or Gli polypeptide; and/or any substance the decreases level of activity of a nucleic acid encoding an Hh, Cdo, Boc, Gas1, Smo, or Gli polypeptide.

In some embodiments, an Hh pathway inhibitor is or includes a Ptc, Hhip, and/or SuFu polypeptide having an activating mutation (e.g., a difference of one or more amino acid residues relative to a reference Ptc, Hhip, and/or SuFu polypeptide and having a higher level of expression and/or activity as compared to such reference polypeptide). In some embodiments, an Hh pathway inhibitor is or includes an Hh, Cdo, Boc, Gas1, Smo, and/or Gli polypeptide having an inhibiting mutation (e.g., a difference of one or more amino acid residues relative to a reference Hh, Cdo, Boc, Gas1, Smo, and/or Gli polypeptide and a lower level of expression and/or activity as compared to such reference polypeptide).

Exemplary, nonlimiting Hh pathway inhibitors useful in the methods described herein include steroidal alkaloids, such as cyclopamine, and derivatives thereof; other small molecules such as SANT-1, SANT-2, SANT-3, and SANT-4 (Chen et al., Proc. Natl. Acad. Sci., USA 99:14071-14076 (2002)); arsenical agents such as arsenic trioxide (ATO); steroidal alkaloids and derivatives thereof, including, for example, cyclopamine and jervine (see, e.g., Chen et al., Genes Devel. 16:2743-2748 (2002); and U.S. Pat. No. 6,432,970); and triparanol (see, e.g., U.S. Pat. No. 6,432, 970).

Additional nonlimiting Hh pathway inhibitors include those described and disclosed in U.S. Pat. No. 7,230,004, U.S. Publ. Nos. 2008/0293754; 2008/0287420; 2008/ 0293755; 2002/0006931; 2007/0021493; US 2007/ 0060546; and International Application Publication Nos. WO 2001/19800, WO 2001/26644, WO 2001/27135, WO 2001/49279, WO 2001/74344, WO 2003/011219, WO 2003/ 088970, WO 2004/020599, WO 2005/013800, WO 2005/ 033288, WO 2005/032343, WO 2005/042700, WO 2006/ 028958, WO 2006/050351, WO 2006/078283, WO 2007/ 054623, WO 2007/059157, WO 2007/120827, WO 2007/ 131201, WO 2008/070357, WO 2008/110611, WO 2008/ 112913, and WO 2008/131354.

Additional nonlimiting examples of Hh pathway inhibitors useful in the methods described herein include vismodegib (Erivedge™, Genentech, Inc., San Francisco, Calif.); BMS-833923 (also known as XL139; Siu et al., J. Clin. Oncol. 28:15s suppl abstr 2501 (2010), and National Institute of Health Clinical Trial Identifier No. NCT006701891); LDE-225 (Pan et al., ACS Med. Chem. Lett. 1:130-134 (2010)); LEQ-506 (National Institute of Health Clinical Trial Identifier No. NCT01106508); PF-04449913 (National Institute of Health Clinical Trial Identifier No. NCT00953758); and 1-piperazinyl-4-arylphthalazines or analogues thereof (Lucas et al., Bioorg. Med. Chem. Lett. 20:3618-22 (2010)).

Treatment of Disorders and Conditions

The present disclosure encompasses the finding that the Hh pathway is involved in signaling through the FSH receptor. Specifically, inhibition of the Hh pathway inhibits FSH binding to the FSH receptor. Accordingly, Hh pathway modulators described herein can be used to modulate FSH binding to the FSH receptor, e.g., to treat or prevent disorders or conditions mediated by or involving FSH signaling.

Follicle Stimulating Hormone and Follicle Stimulating Hormone Receptor

Follicle stimulating hormone (FSH) is a gonadotrophin hormone synthesized and secreted by gonadotropes in the anterior pituitary gland. FSH is a heterodimeric glycoprotein hormone consisting of two noncovalently linked subunits designated alpha and beta. In human FSH, the subunits are 92 amino acids and 111 amino acids, respectively, and each has two N-linked glycosylation sites. FSH has several biological functions in mammals. In males, for example, FSH, in combination with testosterone is required for the initiation and maintenance of qualitatively and quantitatively normal spermatogenesis. In females, FSH is necessary for selection and growth of ovarian follicles and for the production of estrogens from androgen substrate.

FSH is part of the hypothalamo-pituitary-ovarian axis, a classic endocrine closed loop biofeedback system, in which the gonadotrophins (e.g., follicle-stimulating hormone (FSH) and luteinizing hormone (LH)) stimulate ovarian hormone production (e.g., estrogen), which in turn exerts a negative feedback effect on the gonadotrophins, to maintain a regulated system. Gonadotrophins include hormones produced by the pituitary gland that regulate the gonads, such as follicle-stimulating hormone (FSH) and luteinizing hormone (LH). In women, gonadotropins regulate the development of the ovaries and eggs. In men, gonadotropins regulate the development of testes. The secretion of FSH is stimulated by gonadotropin releasing hormone (GnRH). At the beginning of each menstrual cycle, FSH stimulates the growth and recruitment of immature ovarian follicles in the ovary. After 5-6 days, one dominant follicle begins to develop more rapidly. The outer theca and inner granulosa cells of the follicle multiply and under the influence of FSH and LH begin to secrete estrogen and the peptide hormone inhibin. The increase in serum estrogen levels inhibits GnRH, which in turn leads to a decrease in FSH production. Similarly, inhibin inhibits the synthesis and secretion of FSH. Estrogens and inhibin secreted by the ovary inhibit the activity of FSH leading to regression of the smaller, less mature follicles. The estrogen levels peak just before midcycle, and the granulosa cells begin to secrete progesterone. These relative changes in estrogen and progesterone stimulate a brief surge in FSH and LH release that precedes and initiates ovulation.

FSH acts by binding to specific FSH receptors localized primarily in Sertoli cells of the testis and in granulosa cells of the ovary. The FSH receptor belongs to the family of G protein-coupled receptors (GPCR), which are complex membrane-associated receptors characterized by seven-transmembrane spanning domains. The intracellular portion of the FSH receptor is coupled to the G protein Gs and adenylyl cyclase. Upon receptor activation by binding of FSH within the extracellular domain of the receptor, a cascade of cAMP-protein kinase A mediated signaling events is initiated that ultimately leads to specific biological effects of FSH (see, e.g., Simoni et al., Endocr. Rev. 18:739-773 (1997)).

Disorders and Conditions

In some embodiments, an Hh pathway modulator described herein is provided to a female subject to modulate one or more ovarian function. In some embodiments, an Hh pathway activator is provided to a female subject lacking or having a low level of ovarian function (e.g., relative to a control female subject). For example, an Hh pathway activator can be provided to a female subject to increase level of fertility relative to a control subject. In some embodiments, an Hh pathway activator is provided to a female subject to activate and/or increase ovarian function (e.g., a female subject in need thereof).

In some embodiments, an Hh pathway inhibitor is provided to a female subject having a normal or high level of ovarian function (e.g., relative to a control female subject). For example, an Hh pathway inhibitor can be provided to a female subject to decrease level of fertility relative to a control subject. In some embodiments, an Hh pathway inhibitor is provided to a female subject to reduce and/or inhibit ovarian function (e.g., a female subject in need thereof).

In some embodiments, ovarian function refers to ovulation and/or reproductive functions. In some embodiments, ovarian function is measured by determining levels of one or more hormones involved in ovulation and/or reproduction (e.g., determining levels of one or more hormones in blood serum). Such hormones include, without limitation, progesterone, estrogen, FSH, anti mullerian hormone (AMH), inhibin (e.g., inhibin B), and/or androgen (e.g., testosterone). Additionally or alternatively, ovarian function can be measured by determining preservation of oocytes and/or by ultrasound imaging of the ovary.

In some embodiments, an Hh pathway inhibitor described herein is provided to a subject, e.g., a subject suffering from or susceptible to a gynecologic condition. Gynecologic conditions that can be treated using an Hh pathway modulator described herein include, e.g., endometriosis and leiomyomata. In some embodiments, an Hh pathway inhibitor is provided to one or more of target cells or tissues of the ovaries. In some embodiments, target cells or tissues include those cells or tissues that display a disease-associated pathology, symptom, or feature.

In some embodiments, one or more symptoms of endometriosis and/or leiomyomata are reduced in a subject following provision of (e.g., administration of) an Hh pathway inhibitor described herein. For example, provision of (e.g., administration of) an Hh pathway inhibitor can decrease size of diseased tissue and/or lesions (e.g., measured by imaging, e.g., ultrasound, laparoscopy, or MRI), decrease pain (e.g., cyclical dysmennorhea and/or static pain), reduce bleeding, reduce impingement on adjacent organs (e.g., bowel, bladder, or ureter), result in regularizations of menses, and/or improve infertility.

In some embodiments, an Hh pathway activator described herein is provided to a subject, e.g., a subject having a defective level of FSH signaling (e.g., a level of FSH signaling that is lower than a control subject), e.g., in one or more target cells or tissues. In some embodiments, a subject having a defective level of FSH signaling has a reduced level of fertility, e.g., compared to a control subject, and an Hh pathway activator can increase level of fertility.

In some embodiments, an Hh pathway inhibitor described herein is provided to a male subject, e.g., to decrease levels of one or more hormones (e.g., testosterone or dehydroepiandrosterone (DHEA)). In some embodiments, an Hh pathway inhibitor reduces spermatogenesis (e.g., as a male contraceptive). In some embodiments, an Hh pathway activator described herein is provided to a male subject, e.g., to increase levels of one or more hormones (e.g., testosterone or dehydroepiandrosterone (DHEA)). In some embodiments, an Hh pathway activator increases spermatogenesis (e.g., to increase level of fertility).

The term "improve," "increase" or "reduce," as used herein, indicates values that are relative to a control. In some embodiments, a suitable control is a baseline measurement, such as a measurement in the same individual prior to initiation of a treatment described herein, or a measurement in a control individual (or multiple control individuals) in the absence of a treatment described herein. A "control individual" is an individual afflicted with a gynecologic condition, who is about the same age and/or gender as the individual being treated (to ensure that the stages of the disease in the treated individual and the control individual(s) are comparable).

The individual (also referred to as "patient" or "subject") being treated is an individual having a condition described herein or having the potential to develop such condition. In some instances, a subject to be treated is genetically predisposed to developing a condition described herein.

Targeting Agents

An Hh pathway modulator (e.g., an Hh pathway activator or inhibitor) described herein can be provided in association with and/or can include a targeting agent, such as an agent to localize an Hh pathway modulator to a specific target cell or target tissue (e.g., reproductive tissue).

The present disclosure is not limited to any particular targeting agent, and a variety of targeting agents can be used. Examples of such targeting agents include, but are not limited to, nucleic acids (e.g., RNA and DNA), polypeptides (e.g., receptor ligands, signal peptides, avidin, Protein A, and antigen binding proteins), polysaccharides, biotin, hydrophobic groups, hydrophilic groups, drugs, and any organic molecules that bind to target cells or target tissues (e.g., receptors on target cells or target tissues).

Targeting agents can be associated with Hh pathway modulators in any of a number of ways. For example, polypeptide targeting agents can be coupled to or fused to an Hh pathway polypeptide. In other embodiments, a targeting agent is associated (e.g., covalently or noncovalently bound) to an Hh pathway modulator with either short (e.g., direct coupling), medium (e.g., using small-molecule bifunctional linkers such as SPDP (Pierce Biotechnology, Inc., Rockford, Ill.)), or long (e.g., PEG bifunctional linkers (Nektar Therapeutics, Inc., San Carlos, Calif.)) linkages.

In some instances, targeting agents are or comprise antigen binding proteins or antibodies or binding portions thereof. Antibodies can be generated to allow for specific targeting of antigens or immunogens (e.g., target cell or target tissue specific antigens). Such antibodies include, but are not limited to, polyclonal antibodies; monoclonal antibodies or antigen binding fragments thereof; modified antibodies such as chimeric antibodies, reshaped antibodies, humanized antibodies, or fragments thereof (e.g., Fv, Fab', Fab, F(ab')2); or biosynthetic antibodies, e.g., single chain antibodies, single domain antibodies (DAB), Fvs, or single chain Fvs (scFv) (see, e.g., in Harlow et al., Using Antibodies: A Laboratory Manual: Portable Protocol I. Cold Spring Harbor Laboratory (Dec. 1, 1998); Zola, Monoclonal Antibodies: Preparation and Use of Monoclonal Antibodies and Engineered Antibody Derivatives, Springer Verlag (Dec. 15, 2000; 1st edition)). Antibody attachment can be performed by any known method e.g., through standard covalent binding to free amine groups (see, e.g., Torchilin et al., Hybridoma 6:229-240 (1987); Torchilin et al, Biochim. Biophys. Acta 1511:397-411 (2001); Masuko et al., Biomacromol. 6:800-884 (2005)).

In some instances, a targeting agent is or comprises a nucleic acid (e.g., RNA or DNA). In some examples, nucleic acid targeting agents are designed to hybridize by base pairing to a particular nucleic acid (e.g., chromosomal DNA, mRNA, or ribosomal RNA). In some situations, nucleic acid targeting agents bind a ligand on a target cell or target tissue. For example, a nucleic acid can bind human nerve growth factor (Binkley et al., Nuc. Acids Res. 23:3198-205 (1995)). Nucleic acids that bind ligands can be identified by known methods, such as SELEX procedures (see, e.g., U.S. Pat. Nos. 5,475,096; 5,270,163; and 5,475,096; and WO 97/38134; WO 98/33941; and WO 99/07724). In some embodiments, targeting agents can be or comprise aptamers, for example that bind to particular sequences.

Therapeutic Administration

Hh pathway modulators (e.g., Hh pathway activators or inhibitors) described herein can be used to treat a gynecologic condition, e.g., subjects suffering from or susceptible to a gynecologic condition. The route and/or mode of administration of an Hh pathway modulator described herein can vary depending upon the desired results. One with skill in the art, i.e., a physician, is aware that dosage regimens can be adjusted to provide the desired response, e.g., a therapeutic response.

Methods of administration include, but are not limited to, intradermal, intramuscular, intraperitoneal, intravenous, subcutaneous, intranasal, epidural, oral, sublingual, intracerebral, intrathecal, intravaginal, transdermal, rectal, by inhalation, or topical, particularly to the ears, nose, eyes, or skin. The mode of administration is left to the discretion of the practitioner.

An Hh pathway modulator described herein can be formulated as a pharmaceutical composition that includes a suitable amount of a physiologically acceptable excipient (see, e.g., Remington's Pharmaceutical Sciences pp. 1447-1676 (Alfonso R. Gennaro, ed., 19th ed. 1995)). Such physiologically acceptable excipients can be, e.g., liquids, such as water and oils, including those of petroleum, animal, vegetable, or synthetic origin, such as peanut oil, soybean oil, mineral oil, sesame oil and the like. The physiologically acceptable excipients can be saline, gum acacia, gelatin, starch paste, talc, keratin, colloidal silica, urea and the like. In addition, auxiliary, stabilizing, thickening, lubricating, and coloring agents can be used. In one situation, the physiologically acceptable excipients are sterile when administered to an animal. The physiologically acceptable excipient should be stable under the conditions of manufacture and storage and should be preserved against the contaminating action of microorganisms. Saline solutions and aqueous dextrose and glycerol solutions can also be employed as liquid excipients, particularly for injectable solutions. Suitable physiologically acceptable excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Other examples of suitable physiologically acceptable excipients are described in Remington's Pharmaceutical Sciences pp. 1447-1676 (Alfonso R. Gennaro, ed., 19th ed. 1995). The pharmaceutical compositions, if desired, can also contain minor amounts of wetting or emulsifying agents, or pH buffering agents.

Liquid carriers can be used in preparing solutions, suspensions, emulsions, syrups, and elixirs. An Hh pathway modulator described herein can be suspended in a pharmaceutically acceptable liquid carrier such as water, an organic solvent, a mixture of both, or pharmaceutically acceptable oils or fat. The liquid carrier can contain other suitable pharmaceutical additives including solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particular containing additives described herein, e.g., cellulose derivatives, including sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. The liquid carriers can be in sterile liquid form for administration. The liquid carrier for pressurized compositions can be halogenated hydrocarbon or other pharmaceutically acceptable propellant.

In other instances, an Hh pathway modulator described herein is formulated for intravenous administration. Compositions for intravenous administration can comprise a sterile isotonic aqueous buffer. The compositions can also include a solubilizing agent. Compositions for intravenous administration can optionally include a local anesthetic such as lidocaine to lessen pain at the site of the injection. The ingredients can be supplied either separately or mixed together in unit dosage form, for example, as a dry lyophilized powder or water-free concentrate in a hermetically sealed container such as an ampule or sachette indicating the quantity of active agent. Where an Hh pathway modulator described herein is administered by infusion, it can be dispensed, for example, with an infusion bottle containing sterile pharmaceutical grade water or saline. Where an Hh pathway modulator described herein is administered by injection, an ampule of sterile water for injection or saline can be provided so that the ingredients can be mixed prior to administration.

An Hh pathway modulator described herein can be administered rectally or vaginally in the form of a conventional suppository. Suppository formulations can be made using methods known to those in the art from traditional materials, including cocoa butter, with or without the addition of waxes to alter the suppository's melting point, and glycerin. Water-soluble suppository bases, such as polyethylene glycols of various molecular weights, can also be used.

The amount of an Hh pathway modulator described herein that is effective for treating a gynecologic condition can be determined using standard clinical techniques known to those with skill in the art. In addition, in vitro or in vivo assays can optionally be employed to help identify optimal dosage ranges. The precise dose to be employed can also depend on the route of administration, the condition, the seriousness of the condition being treated, as well as various physical factors related to the individual being treated, and can be decided according to the judgment of a health-care practitioner.

Compositions described herein (e.g., therapeutically effective amounts of compositions described herein) can be administered as single administrations or as multiple administrations. Such compositions can be administered at regular intervals, depending on the nature, severity and extent of the subject's condition (e.g., gynecologic condition). In some embodiments, a therapeutically effective amount of a therapeutic agent (e.g., an Hh pathway modulator) is administered periodically at regular intervals (e.g., once every year, once every six months, once every five months, once every three months, bimonthly (once every two months), monthly (once every month), biweekly (once every two weeks), or weekly).

As used herein, the term "therapeutically effective amount" is largely determined based on the total amount of the therapeutic agent contained in pharmaceutical compositions described herein. Generally, a therapeutically effective amount is sufficient to achieve a meaningful benefit to a subject (e.g., treating, modulating, curing, preventing and/or ameliorating a gynecologic condition). For example, a therapeutically effective amount can be an amount sufficient to achieve a desired therapeutic and/or prophylactic effect, such as an amount sufficient to treat a gynecologic condition or the symptoms thereof. Generally, the amount of a therapeutic agent (e.g., an Hh pathway modulator) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays can optionally be employed to identify optimal dosage ranges. A therapeutically effective amount can be administered in a dosing regimen that can include multiple unit doses.

It is to be further understood that for any particular subject, specific dosage regimens can be adjusted over time according to the individual need and the professional judgment of the person administering or supervising the administration of an Hh pathway modulator and that dosage ranges set forth herein are exemplary only and are not intended to limit the scope or practice of the claimed invention.

In some instances, a pharmaceutical composition described herein is in unit dosage form, e.g., as a tablet, capsule, powder, solution, suspension, emulsion, granule, or suppository. In such form, the pharmaceutical composition can be sub-divided into unit doses containing appropriate quantities of an Hh pathway modulator described herein. The unit dosage form can be a packaged pharmaceutical composition, for example, packeted powders, vials, ampoules, pre-filled syringes or sachets containing liquids. The unit dosage form can be, for example, a capsule or tablet itself, or it can be the appropriate number of any such compositions in package form. Such unit dosage form can contain from about 1 mg/kg to about 250 mg/kg, and can be given in a single dose or in two or more divided doses.

Gene Therapy

In embodiments in which an Hh pathway modulator consists of or comprises a nucleic acid encoding an Hh pathway polypeptide, the present disclosure includes methods of administering such nucleic acid to a subject. In some embodiments, a nucleic acid encoding an Hh pathway inhibitor (e.g., Ptc, Hhip, or SuFu polypeptide) is administered to a subject to treat a gynecologic condition.

In some embodiments, a nucleic acid encoding an Hh pathway polypeptide is inserted into a viral vector for delivery to a subject. For example, retrovirus vectors can be used as a recombinant delivery system for transferring nucleic acids encoding Hh pathway polypeptides in vivo (see, e.g., Dropulic, Hum. Gene Ther. 22:649-57 (2011); and Kumar et al., Curr. Gene Ther. 11:144-53 (2011)). Retroviruses useful in methods of the present disclosure include, but are not limited to, murine leukemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), FBR murine osteosarcoma virus (FBR MSV), Moloney murine sarcoma virus (Mo-MSV), Abelson murine leukemia virus (A-MLV), Avian myelocytomatosis virus-29 (MC29), Avian erythroblastosis virus (AEV) and all other retroviridiae including lentiviruses (see, e.g., Coffin et al., "Retroviruses", 1997 Cold Spring Harbor Laboratory Press Eds: J M Coffin, S M Hughes, H E Varmus, pp 758-763)). A replication defective retrovirus can be packaged into virions that can be used to infect a target cell through the use of a helper virus by standard techniques (see, e.g., Current Protocols in Molecular Biology, Ausubel, F. M. et al. (eds.) Greene Publishing Associates, (1989), Sections 9.10-9.14).

In other embodiments, adenovirus-derived vectors are used to deliver nucleic acids encoding Hh pathway polypeptides. The genome of an adenovirus can be manipulated such that it encodes and expresses an Hh pathway polypeptide, but is inactivated in terms of its ability to replicate in a normal lytic viral life cycle (see, e.g., Berkner et al. (1988) BioTechniques 6:616; Rosenfeld et al. (1991) Science 252: 431-434; and Rosenfeld et al. (1992) Cell 68:143-155). Suitable adenoviral vectors useful in the methods of the present disclosure include those derived from the adenovirus strain Ad type 5 d1324 or other strains of adenovirus (e.g., Ad2, Ad3, Ad7 etc.).

In some embodiments, an adeno-associated virus (AAV) is used to deliver a nucleic acid encoding an Hh pathway polypeptide (see, e.g., Muzyczka et al. (1992) Curr. Topics in Micro. and Immunol. 158:97-129). A variety of nucleic acids have been introduced into different cell types using AAV vectors (see, e.g., Hermonat et al. (1984) Proc. Natl. Acad. Sci. USA 81:6466-6470; Tratschin et al. (1985) Mol. Cell. Biol. 4:2072-2081; Wondisford et al. (1988) Mol. Endocrinol. 2:32-39; Tratschin et al. (1984) J. Virol. 51:611-619; and Flotte et al. (1993) J. Biol. Chem. 268:3781-3790). Particularly useful AAVs include those that normally infect humans (e.g., serotypes 1, 2, 3A, 3B, 4, 5, and 6) or primates (e.g., serotypes 1 and 4).

In other embodiments, non-viral methods are useful to deliver a nucleic acid encoding an Hh pathway polypeptide to a subject. Such nonviral methods of gene transfer can exploit mechanisms normally used by mammalian cells for uptake and intracellular transport of macromolecules. For example, liposomal delivery systems, poly-lysine conjugates, and artificial viral envelopes can be used. In some embodiments, a nucleic acid encoding an Hh pathway polypeptide is entrapped in liposomes bearing positive charges on their surface (e.g., lipofectins). In some embodiments, a liposome can be conjugated to a targeting agent described herein (see, e.g., Mizuno et al. (1992) No Shinkei Geka 20:547-551).

Certain cationic polymers ("complexation agents") known to spontaneously bind to and condense nucleic acids into nanoparticles can also be used including, e.g., naturally occurring proteins, peptides, or derivatives, as well as synthetic cationic polymers such as polyethylenimine (PEI), polylysine (PLL), etc. Many useful polymers contain both chargeable amino groups, to allow for ionic interaction with negatively charged DNA phosphate, and a degradable region, such as a hydrolyzable ester linkage. Examples of these include, without limitation, poly(alpha-(4-aminobutyl)-L-glycolic acid), network poly(amino ester), and poly (beta-amino esters). Such complexation agents can protect DNA against degradation, e.g., by nucleases, serum components, etc., and create a less negative surface charge, which may facilitate passage through hydrophobic membranes (e.g., cytoplasmic, lysosomal, endosomal, nuclear) of the cell. Certain complexation agents facilitate intracellular trafficking events such as endosomal escape, cytoplasmic transport, and nuclear entry, and can dissociate from the nucleic acid.

Cell-Based Therapy

An Hh pathway polynucleotide can also be advantageously provided to a cell ex vivo, followed by administration of the living cell to the subject. In some embodiments, primary or secondary cells are genetically engineered to express an Hh pathway polypeptide. Such cells can be obtained from a variety of tissues and include cell types which can be maintained propagated in culture. For example, primary and secondary cells include fibroblasts, endothelial cells, glial cells, and neural cells. In some embodiments, primary cells are obtained from an individual to whom a genetically engineered primary or secondary cells is to be administered. Primary cells can also be obtained from a donor (other than the recipient) of the same species or another species (e.g., mouse, rat, rabbit, cat, dog, pig, cow, bird, sheep, goat, horse).

Primary or secondary cells (e.g., of vertebrate or mammalian origin) can be transfected with a nucleic acid encoding an Hh pathway polypeptide. In some embodiments, a cell is transfected with an exogenous nucleic acid sequence that includes a nucleic acid encoding an Hh pathway polypeptide and an additional nucleic acid sequence (e.g., a regulatory sequence, e.g., a promoter, which causes expression, e.g., inducible expression or upregulation, of an endogenous Hh pathway sequence). Transfected primary or secondary cells may also include DNA encoding a selectable marker that confers a selectable phenotype upon them, facilitating their identification and isolation.

Methods for treating disease by implanting a cell that has been modified to express a recombinant protein are also well known. See, for example, U.S. Pat. No. 5,399,346. Although use of human cells for ex vivo therapy is preferred in some embodiments, other cells such as bacterial cells may be implanted in a subject's vasculature, continuously releasing a therapeutic agent. See, for example, U.S. Pat. Nos. 4,309,776 and 5,704,910.

Combination Therapy

In some embodiments, an Hh pathway modulator described herein is administered to a subject in combination with one or more additional therapies, e.g., to treat a gynecologic condition or one or more symptoms of a gynecologic condition. For example, an Hh pathway modulator can be administered in combination with vismodegib (Erivedge™, Genentech, San Francisco, Calif.).

In some embodiments, combined administration of an Hh pathway modulator and a second agent results in an improvement in a gynecologic condition or a symptom thereof to an extent that is greater than one produced by either the Hh pathway modulator or the second agent alone. The difference between the combined effect and the effect of each agent alone can be a statistically significant difference.

In some embodiments, combined administration of an Hh pathway modulator and a second agent allows administration of the second agent at a reduced dose, at a reduced number of doses, and/or at a reduced frequency of dosage compared to a standard dosing regimen approved for the second agent. For example, approved standard regimen for Erivedge™ is 150 mg once daily. Accordingly, for administration in combination with an Hh pathway modulator, a therapeutically effective amount of Erivedge™ can be a dosage of less than about 150 mg and/or a frequency of greater than about once daily.

Kits

An Hh pathway modulator described herein (e.g., a pharmaceutical composition comprising an Hh pathway modulator) can be provided in a kit. In some instances, the kit includes (a) a container that contains an Hh pathway modulator described herein (e.g., a pharmaceutical composition comprising an Hh pathway modulator) and, optionally (b) informational material. The informational material can be descriptive, instructional, marketing or other material that relates to the methods described herein and/or the use of an Hh pathway modulator, e.g., for therapeutic benefit.

The informational material of the kits is not limited in its form. In some instances, the informational material can include information about production of an Hh pathway modulator, molecular weight of an Hh pathway modulator, concentration, date of expiration, batch or production site information, and so forth. In other situations, the informational material relates to methods of administering an Hh pathway modulator, e.g., in a suitable amount, manner, or mode of administration (e.g., a dose, dosage form, or mode of administration described herein). The method can be a method of treating a subject having a gynecologic condition.

In some cases, the informational material, e.g., instructions, is provided in printed matter, e.g., a printed text, drawing, and/or photograph, e.g., a label or printed sheet. The informational material can also be provided in other formats, such as Braille, computer readable material, video recording, or audio recording. In other instances, the informational material of the kit is contact information, e.g., a physical address, email address, website, or telephone number, where a user of the kit can obtain substantive information about an Hh pathway modulator therein and/or their use in the methods described herein. The informational material can also be provided in any combination of formats.

In addition to an Hh pathway modulator, a kit can include other ingredients, such as a solvent or buffer, a stabilizer, or a preservative. A kit can also include other agents, e.g., a second or third agent, e.g., other therapeutic agents. The components can be provided in any form, e.g., liquid, dried or lyophilized form. The components can be substantially pure (although they can be combined together or delivered separate from one another) and/or sterile. When the components are provided in a liquid solution, the liquid solution can be an aqueous solution, such as a sterile aqueous solution. When the components are provided as a dried form, reconstitution generally is by the addition of a suitable solvent. The solvent, e.g., sterile water or buffer, can optionally be provided in the kit.

A kit can include one or more containers for an Hh pathway modulator and/or other agents. In some cases, a kit contains separate containers, dividers or compartments for an Hh pathway modulator and informational material. For example, an Hh pathway modulator can be contained in a bottle, vial, or syringe, and the informational material can be contained in a plastic sleeve or packet. In other situations, the separate elements of a kit are contained within a single, undivided container. For example, an Hh pathway modulator can be contained in a bottle, vial or syringe that has attached thereto the informational material in the form of a label. In some cases, a kit can include a plurality (e.g., a pack) of individual containers, each containing one or more unit dosage forms (e.g., a dosage form described herein) of an Hh pathway modulator. Containers can include a unit dosage, e.g., a unit that includes an Hh pathway modulator. For example, a kit can include a plurality of syringes, ampules, foil packets, blister packs, or medical devices, e.g., each containing a unit dose. The containers of kits can be air tight, waterproof (e.g., impermeable to changes in moisture or evaporation), and/or light-tight.

A kit can optionally include a device suitable for administration of an Hh pathway modulator, e.g., a syringe or other suitable delivery device. A device can be provided preloaded with an Hh pathway modulator, e.g., in a unit dose, or can be empty, but suitable for loading.

Methods of Identifying Modulators of Hh Pathway Polypeptide Expression or Activity Hh pathway polypeptides described herein (e.g., Boc, Cdo, Gas1, Gli, Hh, Hhip, Ptc, Smo, or SuFu polypeptides) are useful for identifying agents that can be potentially used to treat a disorder described herein, e.g., a gynecologic disorder. For example, an agent that increases expression or activity of a Ptc, Hhip, and/or SuFu polypeptide, or an agent that decreases expression or activity of an Hh, Cdo, Boc, Gas1, Smo, or Gli polypeptide can be identified as an agent that can be used to treat a gynecologic disorder. Numerous methods exist for evaluating whether an agent alters Hh pathway polypeptide expression or Hh pathway polypeptide activity or level. In one embodiment, the ability of a test agent to modulate (e.g., increase or decrease) (e.g., permanently or temporarily) expression from an Hh pathway polynucleotide promoter is evaluated by e.g., routine reporter (e.g., LacZ, luciferase, or GFP) transcription assay. For example, a cell or transgenic animal whose genome comprises a reporter gene operably linked to an Hh pathway polynucleotide promoter, can be contacted with a test agent, and the ability of the test agent to increase or decrease reporter activity is indicative of the ability of the agent to modulate an Hh pathway polypeptide.

In some embodiments, effects of a test agent on Hh pathway polypeptide expression or Hh pathway polypeptide activity or level can be evaluated in a cell, cell lysate, or subject, preferably a non-human experimental mammal, and more preferably a rodent (e.g., a rat, mouse, rabbit), or explant thereof. Methods of assessing Hh pathway polypeptide expression are well known in the art, e.g., Northern analysis, ribonuclease protection assay, reverse transcription-polymerase chain reaction (RT-PCR) or RNA in situ hybridization (see, e.g., Sambrook et al. Molecular Cloning: A Laboratory Manual (3rd ed. 2001)). The level of Hh pathway polypeptide can be monitored by, e.g., Western analysis, immunoassay, or in situ hybridization. In some embodiments, a DNA construct encoding an Hh pathway polypeptide/GFP fusion protein is transfected into cells, and level of GFP fluorescence in the presence or absence of a test agent is determined. An increase in fluorescence in the presence of the test agent is indicative of the ability of the test agent to increase Hh pathway polypeptide level.

In some embodiments, the effect of a test agent on Hh pathway polypeptide expression or Hh pathway polypeptide activity or level is confirmed in a second assay, e.g., is observed as a change, in the presence of the test agent, in the ability of the Hh pathway polypeptide to activate or inhibit an Hh signaling pathway.

Agents and test agents to be used in the methods described herein include crude or partially or substantially purified extracts of organic sources, e.g., botanical (e.g., herbal) and algal extracts, inorganic elements or compounds, as well as partially or substantially purified or synthetic agents, e.g., small molecules, polypeptides, antibodies, and polynucleotides, and libraries of these.

In one example, combinatorial chemical libraries can be produced or obtained that sample chemical compounds that are structurally or chemically related or unrelated. Preparation and screening of combinatorial chemical libraries is well known to those of skill in the art. Such combinatorial chemical libraries include, but are not limited to, peptide libraries (see, e.g., U.S. Pat. No. 5,010,175; Furka, Int. J. Pept. Prot. Res. 37:487-493 (1991); and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries, peptide nucleic acid libraries (see, e.g., U.S. Pat. No. 5,539,083), antibody libraries (see, e.g., Vaughn et al., Nature Biotechnology, 14(3):309-314 (1996) and PCT/US96/10287), carbohydrate libraries (see, e.g., Liang et al., Science, 274:1520-1522 (1996) and U.S. Pat. No. 5,593,853), and small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

All publications, patent applications, patents, and other references mentioned herein are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

The disclosure is further illustrated by the following examples. The examples are provided for illustrative purposes only. They are not to be construed as limiting the scope or content of the disclosure in any way.

EXAMPLES

Example 1—Case Study of Patient Treated with Vismodegib (Erivedge™)

A 34 year old nulliparous woman with a known diagnosis of Gorlin syndrome (Basal cell carcinoma nevus syndrome: Online Mendelian Inheritance in Man #109400) presented with more than 100 discrete BCC papules on the upper trunk and head, and neck regions. She was diagnosed and treated for lymphoma in 1988, prior to the BCCNS diagnosis and received chemotherapy and radiation therapy to the mantle zone, followed by radical neck dissection. She has remained in remission and her therapy had no apparent effect on menstrual function. She experienced menarche at age 13 and had regular menses at 30 to 35 day intervals until starting the current therapy. Medications included synthroid 0.15 mg for longstanding hypothyroidism.

On exam, she demonstrated prominent sclerosis of the lateral neck areas, consistent with chronic surgery and radiation changes. Several of her BCC lesions, while not clinically large, appeared in this area of combined radiation and surgical sclerosis overlying the carotid sheath. Multi-disciplinary consultation recommended against further surgery. She commenced therapy with vismodegib (Erivedge™ Genentech, Inc., San Francisco, Calif.) 150 mg daily. One month later, she became amenorrheic. Approximately four months later, she developed hair loss, slight dysgeusia, and minor leg cramping. Six months after commencing therapy, she had near complete clinical resolution of all lesions. Shortly thereafter she underwent a reproductive endocrinology evaluation. Pertinent exam findings included evidence of moderate atrophic vaginal changes suggesting hypoestrogenism. Transvaginal ultrasonography revealed a small, retroflexed uterus with a small pedunculated leiomyoma and normal ovaries, bilaterally containing multiple pre-antral follicles.

Results of reproductive endocrine testing were unique and novel (Table 1). Her elevated FSH and low estrogen level were indicative of a markedly diminished ovarian reserve. However, the presence of preantral follicles and the high AMH value indicated preservation of normal ovarian potential and possible reversal of effect following cessation of therapy. These findings suggest that the hedgehog pathway may be involved in FSH cell signaling action at the ovarian follicle level wherein normal FSH action is blocked interrupting the negative feedback mechanism of FSH suppression via estradiol and inhibin.

TABLE 1

| Hormone | level | Normal range |
| --- | --- | --- |
| Anti-mulerian hormone (AMH) | 2.6 | <6.9 |
| Leutinizing hormone (LH) | 25.3 | Ovulation Phase range: 14.0-95.6 |
| Follicle stimulating hormone (FSH) | 16.0 | Follicular Phase: 2-8 IU/L |
| Estradiol | 26.9 | Follicular Phase range: 12.5-166 pg/ml |
| Progesterone | 0.4 | Follicular Phase range: 0.2-1.5 Postmenopausal range: |

CONCLUSION

The endocrine profile of a patient who developed amenorrhea while taking vismodegib (Erivedge™) was determined. Endocrine testing of this patient suggested the ovary was in a senescent state, resulting in secondary amenorrhea. Secondary amenorrhea, absence of established menses, may result from a variety of conditions, including suppression of the pituitary release of FSH or its hypothalamic control via gonadotropin releasing hormone GnRH. This can be drug induced, but patients presenting in this manner typically have very low or non-detectable gonadotropin (FSH and LH) levels and low estrogen levels. Alternatively, patients with ovarian failure (follicle depletion or menopause) present with high gonadotropins, which may be induced by radiation and/or medication such as chemotherapy. This patient's prior lymphoma therapy could have produced such a scenario, but onset 23 years after completing treatment and the abrupt occurrence of amenorrhea after years of regular menses following initiation of vismodegib suggested this was unlikely.

Most extraordinary, the paradoxical evidence suggesting a diminished ovarian reserve with elevated FSH and LH levels and low estradiol level, contrasted with a normal anti-mullerian hormone (AMH) level and ultrasound evidence of a normal ovarian preantral follicle count implying normal reproductive potential, provided strong evidence of a unique effect of vismodegib on the FSH receptor and its ligand-dependent signaling. This led to the conclusion that the cause of amenorrhea in at least this female patient treated with visomdegib was due to blockage of the follicle stimulating hormone (FSH) receptor (FSH-R) signaling. Thus, vismodegib blocked the action of FSH on the FSH-R, preventing FSH-R-mediated signal transduction.

EQUIVALENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

```
SEQUENCES
Boc nucleotide sequence - NM_033254.2
                                                              (SEQ ID NO: 1)
gtttctcatagttggcgtcttctaaaggaaaaacactaaaatgaggaactcagcggaccgggagcgacgcagcttgagggaagcat ccctagctgttggcgcagaggggcgaggctgaagccgagtggcccgaggtgtctgaggggctggggcaaaggtgaaagagtttcag aacaagcttcctggaacccatgacccatgaagtcttgtcgacatttataccgtctgagggtagcagctcgaaagtagaagaagtgg agtgttgccagggacggcagtatctctttgtgtgaccctggcggcttatgggacgttggcttcagacctttgtgatacaccatgct gcgtgggacgatgacggcgtggagaggaatgaggcctgaggtcacactggcttgcctcctcctagccacagcaggctgctttgctg acttgaacgaggtccctcaggtcaccgtccagcctgcgtccaccgtccagaagcccggaggcactgtgatcttgggctgcgtggtg gaacctccaaggatgaatgtaacctggcgcctgaatggaaaggagctgaatggctcggatgatgctctgggtgtcctcatcaccca cgggaccctcgtcatcactgcccttaacaaccacactgtgggacggtaccagtgtgtggcccggatgcctgcggggctgtggcca gcgtgccagccactgtgacactagccaatctccaggacttcaagttagatgtgcagcacgtgattgaagtggatgagggaaacaca
```

-continued

```
gcagtcattgcctgccacctgcctgagagccaccccaaagcccaggtccggtacagcgtcaaacaagagtggctggaggcctccag aggtaactacctgatcatgccctcagggaacctccagattgtgaatgccagccaggaggacgagggcatgtacaagtgtgcagcct acaacccagtgacccaggaagtgaaaacctccggctccagcgacaggctacgtgtgcgccgctccaccgctgaggctgcccgcatc atctaccccccagaggcccaaaccatcatcgtcaccaaaggccagagtctcattctggagtgtgtggccagtggaatcccaccccc acgggtcacctgggccaaggatgggtccagtgtcaccggctacaacaagacgcgcttcctgctgagcaacctcctcatcgacacca ccagcgaggaggactcaggcacctaccgctgcatggccgacaatggggttgggcagcccggggcagcggtcatcctctacaatgtc caggtgtttgaaccccctgaggtcaccatggagctatcccagctggtcatccctggggccagagtgccaagcttacctgtgaggt gcgtgggaaccccccgccctccgtgctgtggctgaggaatgctgtgcccctcatctccagccagcgcctccggctctcccgcaggg ccctgcgcgtgctcagcatggggcctgaggacgaaggcgtctaccagtgcatggccgagaacgaggttgggagcgcccatgccgta gtccagctgcggacctccaggccaagcataacccaaggctatggcaggatgctgagctggctactggcacacctcctgtatcacc ctccaaactcggcaaccctgagcagatgctgaggggcaaccggcgctcccagacccccaacgtcagtggggcctgcttccccgc agtgtccaggagagaaggggcagggggctcccgccgaggctcccatcatcctcagctcgccccgcacctccaagacagactcatat gaactggtgtggcggcctcggcatgagggcagtggccggcgccaatcctctactatgtggtgaaacaccgcaaggtcacaaattc ctctgacgattggaccatctctggcattccagccaaccagcaccgcctgaccctcaccagacttgaccccgggagcttgtatgaag tggagatggcagcttacaactgtgcgggagagggccagacagccatggtcaccttccgaactggacggcggcccaaacccgagatc atggccagcaaagagcagcagatccagagagacgaccctggagccagtcccagagcagcagccagccagaccacggccgcctctc ccccccagaagctcccgacaggcccaccatctccacggcctccgagacctcagtgtacgtgacctggattccccgtgggaatggtg ggttcccaatccagtccttccgtgtggagtacaagaagctaaagaaagtgggagactggattctggccaccagcgccatcccccca tcgcggctgtccgtggagatcacgggcctagagaaaggcacctcctacaagtttcgagtccgggctctgaacatgctggggagag cgagcccagcgcccctctcggccctacgtggtgtcgggctacagcggtcgcgtgtacgagaggcccgtggcaggtccttatatca ccttcacggatgcggtcaatgagaccaccatcatgctcaagtggatgtacatcccagcaagtaacaacaacaccccaatccatggc ttttatatctattatcgacccacagacagtgacaatgatagtgactacaagaaggatatggtggaaggggacaagtactggcactc catcagccacctgcagccagagacctcctacgacattaagatgcagtgcttcaatgaaggagggggagagcgagttcagcaacgtga tgatctgtgagaccaaagctcggaagtcttctggccagcctggtcgactgccacccccaactctggccccaccacagccgcccctt cctgaaaccatagagcggccggtgggcactggggccatggtggctcgctccagcgacctgccctatctgattgtcggggtcgtcct gggctccatcgttctcatcatcgtcaccttcatccccttctgcttgtggagggcctggtctaagcaaaaacatacaacagacctgg gttttcctcgaagtgcccttccaccctcctgcccgtatactatggtgccattgggaggactcccaggccaccaggccagtggacag ccctacctcagtggcatcagtggacgggcctgtgctaatgggatccacatgaatagggctgcccctcggctgcagtgggctaccc gggcatgaagcccagcagcactgcccaggcgagcttcagcagcagagtgacaccagcagcctgctgaggcagacccatcttggca atggatatgaccccaaagtcaccagatcacgaggggtcccaagtctagcccggacgagggctcttcttatacacactgcccgac gactccactcaccagctgctgcagccccatcacgactgctgccaacgccaggagcagcctgctgctgtgggccagtcaggggtgag gagagccccgacagtcctgtcctggaagcagtgtgggaccctccatttcactcagggcccccatgctgcttgggccttgtgccag ttgaagaggtggacagtcctgactcctgccaagtgagtggaggagactggtgtcccagcacccgtaggggcctacgtaggacag gaacctggaatgcagctctccccggggccactggtgcgtgtgtcttttgaaacaccacctctcacaatttaggcagaagctgatat cccagaaagactatatattgttttttttttaaaaaaaaaagaagaaaaaagagacagagaaaattggtatttattttttctattat agccatatttatatatttatgcacttgtaaataaatgtatatgttttataattctggagagacataaggagtcctacccgttgagg ttggagagggaaaataaagaagctgccacctaacaggagtcacccaggaaagcaccgcacaggctggcgcgggacagactcctaac ctgggcctctgcagtggcaggcgaggctgcaggaggcccacagataagctggcaagaggaaggatcccaggcacatggttcatca cgagcatgagggaacagcaaggggcacggtatcacagcctggagacacccacacagatggctggatccggtgctacgggaaacatt ttcctaagatgcccatgagaacagaccaagatgtgtacagcactatgagcattaaaaaaaccttccagaatcaataatccgtggcaa catatctctgtaaaaacaaacactgtaacttctaaataaatgtttagtcttccctgtaaccttcaaaaaaaaaaaaaaa
```

-continued

Boc amino acid sequence - NP_150279.1

(SEQ ID NO: 2)

MLRGTMTAWRGMRPEVTLACLLLATAGCFADLNEVPQVTVQPASTVQKPGGTVILGCVVEPPRMNVTWRLNGKELNGSDDALGVLI
THGTLVITALNNHTVGRYQCVARMPAGAVASVPATVTLANLQDFKLDVQHVIEVDEGNTAVIACHLPESHPKAQVRYSVKQEWLEA
SRGNYLIMPSGNLQIVNASQEDEGMYKCAAYNPVTQEVKTSGSSDRLRVRRSTAEAARIIYPPEAQTIIVTKGQSLILECVASGIP
PPRVTWAKDGSSVTGYNKTRFLLSNLLIDTTSEEDSGTYRCMADNGVGQPGAAVILYNVQVFEPPEVTMELSQLVIPWGQSAKLTC
EVRGNPPPSVLWLRNAVPLISSQRLRLSRRALRVLSMGPEDEGVYQCMAENEVGSAHAVVQLRTSRPSITPRLWQDAELATGTPPV
SPSKLGNPEQMLRGQPALPRPPTSVGPASPQCPGEKGQGAPAEAPIILSSPRTSKTDSYELVWRPRHEGSGRAPILYYVVKHRKVT
NSSDDWTISGIPANQHRLTLTRLDPGSLYEVEMAAYNCAGEGQTAMVTFRTGRRPKPEIMASKEQQIQRDDPGASPQSSSQPDHGR
LSPPEAPDRPTISTASETSVYVTWIPRGNGGFPIQSFRVEYKKLKKVGDWILATSAIPPSRLSVEITGLEKGTSYKFRVRALNMLG
ESEPSAPSRPYVVSGYSGRVYERPVAGPYITFTDAVNETTIMLKWMYIPASNNNTPIHGFYIYYRPTDSDNDSDYKKDMVEGDKYW
HSISHLQPETSYDIKMQCFNEGGESEFSNVMICETKARKSSGQPGRLPPPTLAPPQPPLPETIERPVGTGAMVARSSDLPYLIVGV
VLGSIVLIIVTFIPFCLWRAWSKQKHTTDLGFPRSALPPSCPYTMVPLGGLPGHQASGQPYLSGISGRACANGIHMNRGCPSAAVG
YPGMKPQQHCPGELQQQSDTSSLLRQTHLGNGYDPQSHQITRGPKSSPDEGSFLYTLPDDSTHQLLQPHHDCCQRQEQPAAVGQSG
VRRAPDSPVLEAVWDPPFHSGPPCCLGLVPVEEVDSPDSCQVSGGDWCPQHPVGAYVGQEPGMQLSPGPLVRVSFETPPLTI

Cdo nucleotide sequence - FB701823.1

(SEQ ID NO: 3)

gtttctcatagttggcgtcttctaaaggaaaaacactaaaatgaggaactcagcggaccgggagcgacgcagcttgagggaagcat
ccctagctgttggcgcagaggggcgaggctgaagccgagtggcccgaggtgtctgaggggctggggcaaaggtgaaagagtttcag
aacaagcttcctggaacccatgacccatgaagtcttgtcgacatttataccgtctgagggtagcagctcgaaactagaagaagtgg
agtgttgccaggacggcagtatctctttgtgtgaccctggcggcctatgggacgttggcttcagacctttgtgatacaccatgct
gcgtgggacgatgacgcgtggagaggaatgaggcctgaggtcacactggcttgcctcctcctagccacagcaggctgctttgctg
acttgaacgaggtccctcaggtcaccgtccagcctgcgtccaccgtccagaagcccggaggcactgtgatcttgggctgcgtggtg
gaacctccaaggatgaatgtaacctggcgcctgaatggaaaggagctgaatggctcggatgatgctctgggtgtcctcatcaccca
cgggacccctcgtcatcactgcccttaacaaccacactgtgggacggtaccagtgtgtggcccggatgcctgcggggctgtggcca
gcgtgccagccactgtgacactagccaatctccaggacttcaagttagatgtgcagcacgtgattgaagtggatgagggaaacaca
gcagtcattgcctgccacctgcctgagagccaccccaaagcccaggtccggtacagcgtcaaacaagagtggctggaggcctccag
aggtaactacctgatcatgccctcagggaacctccagattgtgaatgccagccaggaggacgagggcatgtacaagtgtgcagcct
acaacccagtgacccaggaagtgaaaacctccggctccagcgacaggctacgtgtgcgccgctccaccgctgaggctgcccgcatc
atctaccccccagaggcccaaaccatcatcgtcaccaaaggccagagtctcattctggagtgtgtggccagtggaatcccacccc
acgggtcacctgggccaaggatgggtccagtgtcaccggctacaacaagacgcgcttcctgctgagcaacctcctcatcgacacca
ccagcgaggaggactcaggcacctaccgctgcatggccgacaatgggttgggcagcccggggcagcggtcatcctctacaatgtc
caggtgtttgaaccccctgaggtcaccatggagctatcccagctggtcatccctggggccagagtgccaagcttacctgtgaggt
gcgtgggaaccccgccctccgtgctgtggctgaggaatgctgtgcccctcatctccagccagcgcctccggctctcccgcaggg
ccctgcgcgtgctcagcatggggcctgaggacgaaggcgtctaccagtgcatggccgagaacgaggttgggagcgcccatgccgta
gtccagctgcggacctccaggccaagcataaccccaaggctatggcaggatgctgagctggctactggcacacctcctgtatcacc
ctccaaaactcggcaaccctgagcagatgctgagggggcaaccggcgctcccagaccccaacgtcagtggggcctgcttccccga
agtgtccaggagagaaggggcaggggctcccgccgaggctcccatcatcctcagctcgccccgcacctccaagacagactcatat
gaactggtgtggcggcctcggcatgagggcagtggccgggcgccaatcctctactatgtggtgaaacaccgcaagcaggtcacaaa
ttcctctgacgattggaccatctctggcattccagccaaccagcaccgcctgaccctcaccagacttgaccccgggagcttgtatg
aagtggagatggcagcttacaactgtgcgggagagggccagacagccatggtcaccttccgaactggacggcggcccaaacccgag
atcatggccagcaaagagcagcagatccagagagacgaccctggagccagtccccagagcagcagccagccagaccacggccgcct -continued

```
ctcccccccagaagctcccgacaggcccaccatctccacggcctccgagacctcagtgtacgtgacctggattcccgtgggaatg gtgggttcccaatccagtccttccgtgtggagtacaagaagctaaagaaagtgggagactggattctggccaccagcgccatcccc ccatcgcggctgtccgtggagatcacgggcctagagaaaggcacctcctacaagtttcgagtccgggctctgaacatgctggggga gagcgagcccagcgcccctctcggccctacgtggtgtcgggctacagcggtcgcgtgtacgagaggcccgtggcaggtccttata tcaccttcacggatgcggtcaatgagaccaccatcatgctcaagtggatgtacatcccagcaagtaacaacaacaccccaatccat ggcttttatatctattatcgacccacagacagtgacaatgatagtgactacaagaaggatatggtggaaggggacaagtactggca ctccatcagccacctgcagccagagacctcctacgacattaagatgcagtgcttcaatgaaggaggggagagcgagttcagcaacg tgatgatctgtgagaccaaagctcggaagtcttctggccagcctggtcgactgccacccccaactctggccccaccacagccgccc cttcctgaaaccatagagcggccggtgggcactggggccatggtggctcgctccagcgacctgccctatctgattgtcggggtcgt cctgggctccatcgttctcatcatcgtcaccttcatccccttctgcttgtggagggcctggtctaagcaaaaacatacaacagacc tgggttttcctcgaagtgcccttccaccctcctgcccgtatactatggtgccattgggaggactcccaggccaccaggccagtgga cagcccacctcagtggcatcagtggacgggcctgtgctaatgggatccacatgaatagggggctgcccctcggctgcagtgggcta cccgggcatgaagcccagcagcactgcccaggcgagcttcagcagcagagtgacaccagcagcctgctgaggcagacccatcttg gcaatggatatgaccccaaagtcaccagatcacgaggggtcccaagtctagcccggacgagggctcttcttatacacactgccc gacgactccactcaccagctgctgcagccccatcacgactgctgccaacgccaggagcagcctgctgctgtgggccagtcagggt gaggagagcccccgacagtcctgtcctggaagcagtgtgggaccctccatttcactcagggccccatgctgcttgggccttgtgc cagttgaagaggtggacagtcctgactcctgccaagtgagtggaggagactggtgtcccagcacccgtaggggcctacgtagga caggaacctggaatgcagctctccccggggccactggtgcgtgtgtcttttgaaacaccacctctcacaatttaggcagaagctga tatcccagaaagactatatattgttttttttttaaaaaaaaaaagaagaaaaaagagacagagaaaattggtatttattttctatt atagccatatttatatatttatgcacttgtaaataaatgtatatgttttataattctggagagacataaggagtcctacccgttga ggttggagagggaaaataaagaagctgccacctaacaggagtcacccaggaaagcaccgcacaggctggcgcgggacagactccta acctggggcctctgcagtggcaggcgaggctgcaggaggcccacagataagctggcaagaggaaggatcccaggcacatggttcat cacgagcatgagggaacagcaaggggcacggtatcacagcctggagacacccacacagatggctggatccggtgctacgggaaaca ttttcctaagatgcccatgagaacagaccaagatgtgtacagcactatgagcattaaaaaaccttccagaatcaataatccgtggc aacatatctctgtaaaaacaaacactgtaacttctaaataaatgtttagtcttccctgtaaaa
```

Cdo amino acid sequence - NP_001230526.1
(SEQ ID NO: 4)

```
MHPDLGPLCTLLYVTLTILCSSVSSDLAPYFTSEPLSAVQKLGGPVVLHCSAQPVTTRISWLHNGKTLDGNLEHVKIHQGTLTILS
LNSSLLGYYQCLANNSIGAIVSGPATVSVAVLGDFGSSTKHVITAEEKSAGFIGCRVPESNPKAEVRYKIRGKWLEHSTENYLILP
SGNLQILNVSLEDKGSYKCAAYNPVTHQLKVEPIGRKLLVSRPSSDDVHILHPTHSQALAVLSRSPVTLECVVSGVPAPQVYWLKD
GQDIAPGSNWRRLYSHLATDSVDPADSGNYSCMAGNKSGDVKYVTYMVNVLEHASISKGLQDQIVSLGATVHFTCDVHGNPAPNCT
WFHNAQPIHPSARHLTAGNGLKISGVTVEDVGMYQCVADNGIGFMHSTGRLEIENDGGFKPVIITAPVSAKVADGDFVTLSCNASG
LPVPVIRWYDSHGLITSHPSQVLRSKSRKSQLSRPEGLNLEPVYFVLSQAGASSLHIQAVTQEHAGKYICEAANEHGTTQAEASLM
VVPFETNTKAETVTLPDAAQNDDRSKRDGSETGLLSSFPVKVHPSAVESAPEKNASGISVPDAPIILSPPQTHTPDTYNLVWRAGK
DGGLPINAYFVKYRKLDDGVGMLGSWHTVRVPGSENELHLAELEPSSLYEVLMVARSAAGEGQPAMLTFRTSKEKTASSKNTQASS
PPVGIPKYPVVSEAANNNFGVVLTDSSRHSGVPEAPDRPTISTASETSVYVTWIPRANGGSPITAFKVEYKRMRTSNWLVAAEDIP
PSKLSVEVRSLEPGSTYKFRVIAINHYGESFRSSASRPYQVVGFPNRFSSRPITGPHIAYTEAVSDTQIMLKWTYIPSSNNNTPIQ
GFYIYYRPTDSDNDSDYKRDVVEGSKQWHMIGHLQPETSYDIKMQCFNEGGESEFSNVMICETKVKRVPGASEYPVKDLSTPPNSL
GSGGNVGPATSPARSSDMLYLIVGCVLGVMVLILMVFIAMCLWKNRQQNTIQKYDPPGYLYQGSDMNGQMVDYTTLSGASQINGNV
HGGFLTNGGLSSGYSHLHHKVPNAVNGIVNGSLNGGLYSGHSNSLTRTHVDFEHPHHLVNGGGMYTAVPQIDPLECVNCRNCRNNN
RCFTKTNSTFSSSPPPVVPVVAPYPQDGLEMKPLSHVKVPVCLTSAVPDCGQLPEESVKDNVEPVPTQRTCCQDIVNDVSSDGSED
PAEFSRGQEGMINLRIPDHLQLAKSCVWEGDSCAHSETEINIVSWNALILPPVPEGCAEKTMWSPPGIPLDSPTEVLQQPRET
```

Gas1 nucleotide sequence - BC136586.1

(SEQ ID NO: 5)

caaacttttccaccggctccgcgtccgccgctccccgcgcctcgtctccttccccctcctctcccggcggccgccgctgcccgcga tggtggccgcgctgctgggcggcggcggcgaggcccgcggggggacagtgccgggcgcctggctgtgcctgatggcgctgctgcag ctgctgggctcggccgccgcggggatcggggctggcgcacggccgccgcctcatctgctggcaggcgctgctgcagtgccagggga gccggagtgcagctacgcctacaaccaatacgccgaggcgtgcgcgccggtgctggcgcagcacggcgggggcgacgcgcccgggg ccgccgccgccgctttcccggcctcggccgcctcttctcgtcgcgctggcgctgcccgagtcactgcatctcggccctcattcag ctcaaccacacgcgccgcgggcccgccctggaggactgtgactgcgcgcaggacgagaactgcaagtccaccaagcgcgccattga gccgtgcctgccccggacgagcggcggcggcgcggcggccccggcgcgggcggggtcatgggctgcaccgaggcccggcggcgct gcgaccgcgacagccgctgcaacctggcgctgagccgctacctgacctactgcggcaaagtcttcaacgggctgcgctgcacggac gaatgccgcaccgtcattgaggacatgctggctatgcccaaggcggcgctgctcaacgactgcgtgtgcgacggcctcgagcggcc catctgcgagtcggtcaaggagaacatggcccgcctgtgcttcggcgccgagctgggcaacggccccggcagcagcggctcggacg ggggcctggacgactactacgatgaggactacgatgacgagcagcgcaccggggggcgcgggtggtgagcagccgctggacgacgac gacggcgtcccgcaccaccgcgcccgggcagcggcgctgctgcatcgggcggccgcggggacctgccctatgggcctgggcgcag gagcagcggcggcggccgcttggcgcccggggcgcctggaccccactcgcctccatcttgctgctgctgcttgggccgctct tttagccctcgcgcccccgccgttggctgcgggagagcccgcgtcccactcccgtgctcgcctcgacccgcgccgggcacctgt ggcttgggacagatagaagggatggttggggatacttcccaaaactttttccaagtcaacttggtgtagccggttccccggccacg actctgggcacttcccctgaagctcctctccggagct Gas1 amino acid sequence - CAH71308.1

(SEQ ID NO: 6)

MVAALLGGGGEARGGTVPGAWLCLMALLQLLGSAPRGSGLAHGRRLICWQALLQCQGEPECSYAYNQYAEACAPVLAQHGGGDAPG

AAAAAFPASAASFSSRWRCPSHCISALIQLNHTRRGPALEDCDCAQDENCKSTKRAIEPCLPRTSGGGAGGPGAGGVMGCTEARRR

CDRDSRCNLALSRYLTYCGKVFNGLRCTDECRTVIEDMLAMPKAALLNDCVCDGLERPICESVKENMARLCFGAELGNGPGSSGSD

GGLDDYYDEDYDDEQRTGGAGGEQPLDDDDGVPHPPRPGSGAAASGGRGDLPYGPRRSSGGGGRLAPRGAWTPLASILLLLLGPL

F

Gli1 nucleotide sequence - NM_005269.2

(SEQ ID NO: 7)

atgttcaactcgatgaccccaccaccaatcagtagctatggcgagccctgctgtctccggccccctcccagtcaggggcccccag tgtggggacagaaggactgtctggcccgcccttctgccaccaagctaacctcatgtccggcccccacagttatgggccagccagag agaccaacagctgcaccgagggcccactcttttcttctccccggagtgcagtcaagttgaccaagaagcgggcactgtccatctca cctctgtcggatgccagcctggacctgcagacggttatccgcacctcacccagctccctcgtagctttcatcaactcgcgatgcac atctccaggaggctcctacggtcatctctccattggcaccatgagcccatctctgggattcccagcccagatgaatcaccaaaaag ggccctcgccttcctttggggtccagccttgtggtccccatgactctgcccggggtgggatgatcccacatcctcagtcccgggga cccttcccaacttgccagctgaagtctgagctggacatgctggttggcaagtgccggaggaaccctggaaggtgatatgtccag ccccaactccacaggcatacaggatcccctgttggggatgctggatgggcgggaggacctcgagagagaggagaagcgtgagcctg aatctgtgtatgaaactgactgccgttgggatggctgcagccaggaatttgactcccaagagcagctggtgcaccacatcaacagc gagcacatccacggggagcggaaggagttcgtgtgccactgggggggctgctccagggagctgaggcccttcaaagcccagtacat gctggtggttcacatgcgcagacacactggcgagaagccacacaagtgcacgtttgaagggtgccggaagtcatactcacgcctcg aaaacctgaagacgcacctgcggtcacacacgggtgagaagccatacatgtgtgagcacgagggctgcagtaaagccttcagcaat gccagtgaccgagccaagcaccagaatcggacccattccaatgagaagccgtatgtatgtaagctccctggctgcaccaaacgcta tacagatcctagctcgctgcgaaaacatgtcaagacagtgcatggtcctgacgcccatgtgaccaaacggcaccgtggggatggcc ccctgcctcgggcaccatccattctacagtggagcccaagagggagcgggaaggaggtcccatcagggaggaaagcagactgact gtgccagagggtgccatgaagccacagccaagccctggggcccagtcatcctgcagcagtgaccactccccggcagggagtgcagc

```
caatacagacagtggtgtggaaatgactggcaatgcaggggcagcactgaagacctctccagcttggacgagggaccttgcattg
ctggcactggtctgtccactcttcgccgccttgagaacctcaggctggaccagctacatcaactccggccaatagggacccggggt
ctcaaactgcccagcttgtcccacaccggtaccactgtgtcccgccgcgtgggcccccagtctctcttgaacgccgcagcagcag
ctccagcagcatcagctctgcctatactgtcagccgccgctcctccctggcctctcctttccccctggctccccaccagagaatg
gagcatcctccctgcctggccttatgcctgcccagcactacctgcttcgggcaagatatgcttcagccagaggggtggtacttcg
cccactgcagcatccagcctggatcggataggtggtcttcccatgcctccttggagaagccgagccgagtatccaggatacaaccc
caatgcaggggtcaccggagggccagtgacccagcccaggctgctgaccgtcctgctccagctagagtccagaggttcaagagcc
tgggctgtgtccataccccacccactgtggcaggggaggacagaactttgatccttacctcccaacctctgtctactcaccacag
cccccagcatcactgagaatgctgccatggatgctagagggctacaggaagagccagaagttgggacctccatggtgggcagtgg
tctgaaccctatatggacttccacctactgatactctgggatatgggggacctgaaggggcagcagctgagccttatggagcga
ggggtccaggctctctgcctcttgggcctggtccaccccaactatggccccaaccctgtcccagcaggcctcatatcctgac
cccacccaagaaacatgggtgagttcccttcccactctgggctgtaccaggcccaaggctctaggtggaacctacagccagtg
tcctcgacttgaacattatggacaagtgcaagtcaagccagaacagggtgcccagtggggtctgactccacaggactggcaccct
gcctcaatgcccaccccagtgaggggcccccacatccacagcctctcttttcccattaccccagccctctcctccccaatatctc
cagtcaggcccctatcccagccacccctgattatcttccttcagaacccaggcctgcctggactttgattcccccacccattc
cacagggcagctcaaggctcagcttgtgtgtaattatgttcaatctcaacaggagctactgtgggagggtgggggcagggaagatg
ccccgcccaggaaccttcctaccagagtcccaagtttctgggggggttcccaggttagcccaagccgtgctaaagctccagtgaac
acatatggacctggctttggacccaacttgcccaatcacaagtcaggttcctatcccaccccttcaccatgccatgaaaattttgt
agtgggggcaaataggcgcttcacataggggcagcagcaccacctcgacttctgcccccattgcccacttgctatgggcctctcaaag
tgggaggcacaaaccccagctgtggtcatcctgaggtgggcaggctaggagggggtcctgccttgtaccctcctcccgaaggacag
gtatgtaaccccctggactctcttgatcttgacaacactcagctggactttgtggctattctggatgagccccagggctgagtcc
tcctccttcccatgatcagcggggcagctctggacataccccacctccctctgggcccccaacatggctgtgggcaacatgagtg
tcttactgagatccctacctggggaaacagaattcctcaactctagtgcctaa
```

Gli1 amino acid sequence - NP_005260.1

(SEQ ID NO: 8)

MFNSMTPPPISSYGEPCCLRPLPSQGAPSVGTEGLSGPPFCHQANLMSGPHSYGPARETNSCTEGPLFSSPRSAVKLTKKRALSIS
PLSDASLDLQTVIRTSPSSLVAFINSRCTSPGGSYGHLSIGTMSPSLGFPAQMNHQKGPSPSFGVQPCGPHDSARGGMIPHPQSRG
PFPTCQLKSELDMLVGKCREEPLEGDMSSPNSTGIQDPLLGMLDGREDLEREEKREPESVYETDCRWDGCSQEFDSQEQLVHHINS
EHIHGERKEFVCHWGGCSRELRPFKAQYMLVVHMRRHTGEKPHKCTFEGCRKSYSRLENLKTHLRSHTGEKPYMCEHEGCSKAFSN
ASDRAKHQNRTHSNEKPYVCKLPGCTKRYTDPSSLRKHVKTVHGPDAHVTKRHRGDGPLPRAPSISTVEPKREREGGPIREESRLT
VPEGAMKPQPSPGAQSSCSSDHSPAGSAANTDSGVEMTGNAGGSTEDLSSLDEGPCIAGTGLSTLRRLENLRLDQLHQLRPIGTRG
LKLPSLSHTGTTVSRRVGPPVSLERRSSSSSSISSAYTVSRRSSLASPFPPGSPPENGASSLPGLMPAQHYLLRARYASARGGGTS
PTAASSLDRIGGLPMPPWRSRAEYPGYNPNAGVTRRASDPAQAADRPAPARVQRFKSLGCVHTPPTVAGGGQNFDPYLPTSVYSPQ
PPSITENAAMDARGLQEEPEVGTSMVGSGLNPYMDFPPTDTLGYGGPEGAAAEPYGARGPGSLPLGPGPPTNYGPNPCPQQASYPD
PTQETWGEFFSHSGLYPGPKALGGTYSQCPRLEHYGQVQVKPEQGCPVGSDSTGLAPCLNAHPSEGPFHPQPLFSHYPQPSPPQYL
QSGPYTQFPPDYLPSEPRPCLDFDSPTHSTGQLKAQLVCNYVQSQQELLWEGGGREDAPAQEPSYQSPKFLGGSQVSPSRAKAPVN
TYGPGFGPNLPNHKSGSYPTPSPCHENFVVGANRASHRAAAPPRLLPPLPTCYGPLKVGGTNPSCGHPEVGRLGGGPALYPPPEGQ
VCNPLDSLDLDNTQLDFVAILDEPQGLSPPPSHDQRGSSGHTPPPSGPFNMAVGNMSVLLRSLPGETEFLNSSA

Gli2 nucleotide sequence - NM_001081125

(SEQ ID NO: 9)

```
atggagacttctgccccagcccctgcactggagaagaaagaagccaagagtggtctcttggaggacagcagcttcccgacccagg
gaaaaaggcctgtcctctggcggtggccgcagctgtagccgcccacggagttcctcagcagctcctgccggctttccacgcgcctt
tgccgattgacatgagacaccaggagggaaggtaccattatgaccctcactctgtccacagtgtacgcgggcctccaccctaagt
```

-continued

```
ggcagccctgtcatctcagatatctccttgatacgactttctccacaccctgctggccctggagagtcacccttcagcgcccacca
cccctacgtgaaccccatatggagcactacctccggtctgtgcacagcagcccacactctcaatgatctctgccgccaggggcc
tcagccctgctgatgtggcccacgaacatctgaaagagaggggactctttagcctcgcagccccaggcaccaacccttcagactat
taccaccagatgaccctcatggcaagccaccccaccccttatggggaccttctaatgcagagcggggtgctgctagcgcacccca
tctccatgactacctcaaccctgtggatgcatcacgattctctagtccacgtgtgaccccacgactgagccgcaagcgggctctgt
ccatctccccgctctcagatgccagcctcgacctacaacgcatgattcggacctctcccaactcgctggtagcttacatcaacaac
tccaggagcagctcagcagccagtggctcttatggacatctgtctgctggtgccctcagcccagccttcacttttccccaccccat
caatcctgtggcctaccagcagatcctgagccagcagcggggcctgggctcagcctttggacacacaccaccccctgatccagcctt
cacccaccttcttggcccagcagcccatgactctcacctccatcagcaccatgcctacccaactcagcagcagtagcagcaactgt
ctaaatgatgccaaccagaacaagcagaacagcgagtcagctgtgagcagcaccgtgaaccccatcaccattcataagcggagcaa
ggtcaagactgaggctgagggcctgcgtccagcatcccgcttggactgacacaggagcagctggccgatctcaaggaagacctgg
acagggatgactgtaagcaggaggccgaggtggtcatctacgagaccaactgccactgggcagactgcaccaaggagtatgacaca
caggagcagctggtgcatcatatcaacaatgaacacatccacggggagaagaaggagttcgtgtgccgctggcaggcctgcacgag
agagcagaagcccttcaaggcccagtacatgctggttgttcacatgcgcagacacacgggtgagaagccacacaagtgcacgttcg
aaggctgttccaaggcctactctcgcctggagaacctgaagacacacctgcgttcacacacaggagagaagccatatgtgtgtgaa
cacgaaggctgtaacaaagccttctccaatgcctcagaccgcgccaagcaccagaaccgcactcactccaatgagaaaccctacat
ctgcaagatcccaggctgcaccaagaggtacacagaccccagctcactccgcaagcatgtgaagactgtccatgggccagacgccc
atgtcaccaagaaacagcgtaatgatgtgcatgtccgtgctccactgctcaaggagaatggggataatgaggccagcgccgagcca
ggtggccggggacctgaggagagtgtggaggccagtagcaccagccacactgtggaggactgcctacatatcaaagccatcaagac
agagagctccgggctttgtcagtccaccccggggcccagtcatcctgcagcagcgagccctctcccctgggcagtgccccaaca
atgacagtggcatggagatgccggggacagggcctgggagtctgggagacctgacagcactggctgacacgtgtccaggagctgac
acctcagccctggctgcaccctccactggtggcctgcagctgcgcaaacacatgagcaccgtgcatcgctttgagcagctgaagag
agagaagctcaagtcactgaaggattcctgctcgtgggccggcccagctccacacacccgcaacaccaagctgcctcccctt ccag
tcaatggttctgtcctggaaaacttcaacaatacaggggggcggtggaccggcaggactgctgcccagccagcggctaccagagctg
accgaagtgacgatgctgagccagctgcaggaacgaagagacagctccaccagcaccatgagctcggcctacactgtgagccgccg
ctcctctggcatctccccatacttctctagccgtcgctccagcgaggcttcgcctctcggtggcctacgcccgcacaacgccagct
cagcagactcctatgacccatctccacagatgcctctcggcgctccagtgaagccagccagtgcagtggcggtggcccagggctg
ctcaacctcacacctgcgcagcagtacaacctgcgtgccaagtacgcagcggccacaggtggaccaccgcccacgccactgccggg
cctcgatcgtgtaagccttcgtacccgcctggccttgctggatgctcctgagcgtgcacttcctggtgcctgcccacatccactgg
ggccacggcgtggcagcgatgggcctacctatagccatggtcatggccatggctacgcaggtgcggctccagcattcccccacgag
gggccaaacagcagcacacggcgggccagcgaccctgtgcggcgccctgaccccttattctgcctcgagtgcaacgtttccacag
tacccacaacatgaatccaggttcactgccaccctgcgctgatcggcgtggcctgcacgtacagagccaccccagcgtagacagca
acctgacccgcaacgcctactctcccagaccccctagcatcaatgagaacgtggtgatggaggccgtggctgctggggtagacggc
ccagggctagagtgcgacctggggctggtggaggatgagctggtgctgccagatgatgtggtacagtacatcaaggctcacaccgg
tggtaccttggatgacggcattcggcaggggtatcccacagaaggtactggcttccccgagaactctaagctgcccagtcctgggc
tacaaggccaccgcaggctagcagctgccgactccaacatgggtccttctgctcctggactcggggctgccagctgagctacagc
ccctcctccaacctcaacaagagcaacatgcctgtgcagtggaatgaggtgagttctggcaccgtggatgccctgcctacccaggt
gaagccacctcctttccctcacagcaacctggctgtggtccaacagaagccagcctttggccagtatccaggatataatccacaat
ccgtgcagagcagctccggaggtctagacagcacccagccgcacctacagcttcgaggagccccctctgcatcaagagggagctac
acgcaacagcctcgacagccagctgcaggcagtcagtgcctgggtatgagtgcggccatgagcccgcaggccagctacagccaagc
```

-continued

```
ccaccccagctgagcccaaacattgtcagcggatctctgaaccagttttctccctcctgcagcaatatggcagccaagcccagcc
acctgggactccctcagcaaatggaagttgtcccaatgccaccatcatgaatggccatcaacgggagcacgggtccccaattca
tccctggctgcggtgtcacaacctcacccagtcctgagctatccccagcaggacagctaccaacagggctccaaccttctgtcatc
ccatcagcctggcttcatggagtcccagcagaacgcgggctttggtctcatgcagcctcggccacccctggaacccaacacggcca
gccgtcaccgtggagtacgttctgggcaacagcagttgtatgccaggaccactggccaagccatggtcacatcagccaaccaagag
acagcagaagctatgcccaagggaccagcagggaccatggtatccctagctcctcagccatctcaggacacagggcgggcacaaga
tcagaacacgctatactactatggccagatccacatgtatgaacagaatggaggctgcccagccgtgcagccccagccgccacaac
cacaagcttgctcagacagtatccagcctgagccttttgccttcaccgggagtcaaccaggtgtctagcaccgtggactcccagctc
ctggagcccccccagattgactttgatgccatcatggatgatggtgatcactcgagtttgttttctggtgcactgagcccaacccct
tctccacaatctctcccagaattcctcacgcctcaccacaccccggaattccttgacactgccctccatccctgcgggcatcagca
acatggccgtgggcgacatgagttccatgctcaccagcctggctgaagagagcaagttttaaacatgatgacctaa
```

Gli2 amino acid sequence - NP_001074594

(SEQ ID NO: 10)

METSAPAPALEKKEAKSGLLEDSSFPDPGKKACPLAVAAAVAAHGVPQQLLPAFHAPLPIDMRHQEGRYHYDPHSVHSVHGPPTLS
GSPVISDISLIRLSPHPAGPGESPFSAHHPYVNPHMEHYLRSVHSSPTLSMISAARGLSPADVAHEHLKERGLFSLAAPGTNPSDY
YHQMTLMASHPTPYGDLLMQSGGAASAPHLHDYLNPVDASRFSSPRVTPRLSRKRALSISPLSDASLDLQRMIRTSPNSLVAYINN
SRSSSAASGSYGHLSAGALSPAFTFPHPINPVAYQQILSQQRGLGSAFGHTPPLIQPSPTFLAQQPMTLTSISTMPTQLSSSSSNC
LNDANQNKQNSESAVSSTVNPITIHKRSKVKTEAEGLRPASPLGLTQEQLADLKEDLDRDDCKQEAEVVIYETNCHWADCTKEYDT
QEQLVHHINNEHIHGEKKEFVCRWQACTREQKPFKAQYMLVVHMRRHTGEKPHKCTFEGCSKAYSRLENLKTHLRSHTGEKPYVCE
HEGCNKAFSNASDRAKHQNRTHSNEKPYICKIPGCTKRYTDPSSLRKHVKTVHGPDAHVTKKQRNDVHVRAPLLKENGDNEASAEP
GGRGPEESVEASSTSHTVEDCLHIKAIKTESSGLCQSSPGAQSSCSSEPSPLGSAPNNDSGMEMPGTGPGSLGDLTALADTCPGAD
TSALAAPSTGGLQLRKHMSTVHRFEQLKREKLKSLKDSCSWAGPAPHTRNTKLPPLPVNGSVLENFNNTGGGGPAGLLPSQRLPEL
TEVTMLSQLQERRDSSTSTMSSAYTVSRRSSGISPYFSSRRSSEASPLGGLRPHNASSADSYDPISTDASRRSSEASQCSGGGPGL
LNLTPAQQYNLRAKYAAATGGPPPTPLPGLDRVSLRTRLALLDAPERALPGACPHPLGPRRGSDGPTYSHGHGHGYAGAAPAFPHE
GPNSSTRRASDPVRRPDPLILPRVQRFHSTHNMNPGSLPPCADRRGLHVQSHPSVDSNLTRNAYSPRPPSINENVVMEAVAAGVDG
PGLECDLGLVEDELVLPDDVVQYIKAHTGGTLDDGIRQGYPTEGTGFPENSKLPSPGLQHRRLAAADSNMGPSAPGLGGCQLSYS
PSSNLNKSNMPVQWNEVSSGTVDALPTQVKPPPFPHSNLAVVQQKPAFGQYPGYNPQSVQSSSGGLDSTQPHLQLRGAPSASRGSY
TQQPRQPAAGSQCLGMSAAMSPQASYSQAHPQLSPNIVSGSLNQFSPSCSNMAAKPSHLGLPQQMEVVPNATIMNGHQREHGVPNS
SLAAVSQPHPVLSYPQQDSYQQGSNLLSSHQPGFMESQQNAGFGLMQPRPPLEPNTASRHRGVRSGQQQLYARTTGQAMVTSANQE
TAEAMPKGPAGTMVSLAPQPSQDTGRAQDQNTLYYYGQIHMYEQNGGCPAVQPQPPQPQACSDSIQPEPLPSPGVNQVSSTVDSQL
LEPPQIDFDAIMDDGDHSSLFSGALSPTLLHNLSQNSSRLTTPRNSLTLPSIPAGISNMAVGDMSSMLTSLAEESKFLNMMT

Gli3 nucleotide sequence - NM_000168.5

(SEQ ID NO: 11)

```
atggaggcccagtcccacagctccacgaccactgaaaagaaaaagttgagaattccatagtgaagtgctccactcgaacagatgt
gagcgagaaagccgttgcctccagcaccacttctaatgaggatgaaagtcctggacagacttatcacagagagagaagaaacgcaa
tcactatgcagccacagaatgtccaggggctcagcaaagtcagtgaggaaccttcaacatcgagtgacgagagggcctcattgatc
aagaaagagatccatgggtccctgccacacgtggcggagccctctgtgccgtaccgcgggacggtgtttgccatggaccccaggaa
tggttacatggagcccactaccacccctcctcatcttttccctgccttccatcctcctgtaccaattgatgccagacatcatgagg
gccgttaccattacgatccatctccgattcctccattgcatatgacttccgccttatctagtagccctacgtatccggacctgccc
ttcattaggatctcccccacaccggaacccactgctgcttccgagtctcccttcagccctccacatccctacattaatccctacat
ggactatatccgctccttgcacagcagcccatcgctctccatgatctcagcaacccgtgggctgagccctacagatgcgccccatg
caggagtcagcccagcagaatactatcatcagatggccctgctaactggccagcgcagccctatgcagacattattccctcagct
gccaccgccggcacgggggccatccacatggaatatcttcatgctatggatagcaccagattctccagccccaggctgtcagccag
```

-continued gccgagccgaaaacgtacactgtccatatcaccactctccgatcatagctttgaccttcagaccatgataaggacgtctcccaact ccttggtcacgattctcaataattcccgtagcagctcttcagcaagtggctcctatggtcacttatctgcaagtgcaatcagccct gccttgagcttcacctactcttccgcgcccgtctctctccacatgcatcagcagatcctaagccgacaacagagcttaggttcagc ctttggacacagccctccactcatccaccctgccccaacttttccaacacagaggcctattccagggatccctacggttctgaacc ccgtccaggtcagctccggcccttctgagtcctcacagaacaagcccacgagtgagtctgcagtgagcagcactggtgacccgatg cacaacaagaggtccaagatcaaacccgatgaagacctccccagcccaggggctcggggcagcaggaacagcccgaaggaacaac ccttgtcaaggaggaagggacaaagatgaaagcaaacaggagcctgaagtcatctatgagacaaactgccactgggaaggctgcg cgagggagttcgacacccaagagcagcttgtgcaccatataaataacgaccatattcatggagagaagaaggagttcgtgtgcagg tggctggactgctcaagagagcagaaacccttcaaagcccagtatatgttggtagtgcatatgagaagacacacgggcgagaagcc tcacaaatgcactttgaaggttgcacaaaggcctactcgagactagaaaacttgaaaacacacttgagatctcacactggagaga aaccatacgtctgtgagcacgaaggttgcaacaaggctttctcaaatgcctctgatcgcgccaaacaccaaaacagaacgcattcc aatgagaaaccatatgtgtgcaaaatcccaggctgcactaagcgttacacagacccaagctccctccggaaacatgtgaagacagt gcatggcccagaggctcatgtcaccaagaagcagcgaggggacatccatcctcggccgccaccccgagagattccggcagccatt cacagtccaggtcgcctggccgaccgactcagggagcccttggtgagcagcaggacctcagcaacactacctcaaagcgggaagaa tgcctccaggtgaaaaccgtcaaggcagagaagccaatgacatctcagccaagccctggtggtcagtcttcatgcagcagccaaca gtcccccatcagcaactattccaacagtgggctcgagcttcctctgaccgatggaggtagtataggagacctcagtgccatcgatg aaacccccaatcatggactcaaccatttccactgcaaccacagcccttgctttgcaagccaggagaaacccggcagggaccaaatgg atggagcacgtaaaactagaaaggctaaaacaagtgaatggaatgtttccgcgactgaaccccattctaccccctaaagccctgc ggtctctcctctcataggaaatggcacacagtccaacaacacctgcagcttgggtgggcccatgacgcttctcccgggcagaagcg acctctctggggtggacgtcactatgctgaacatgctcaacagaagggacagcagcgccagcaccatcagctcggcctacctgagc agccgccgctcctcagggatctcgccctgcttctccagccgccgctccagcgaggcgtcacaggccgagggccggccgcagaacgt gagcgtggccgactcctacgacccccatctccaccgacgcctcgcgccgctccagcgaagccagccagagcgacggcctgcccagcc tgctcagcctcacgcccgcccagcagtaccgcctcaaggccaagtacgcggctgccacaggagggccgccgccgacgcccctgccc aacatggagaggatgagcctgaagacgcgcctggcgctgctcggggatgccctcgagcctggcgtggccctgcctccagttcatgc cccgaggaggtgcagcgacggggagcccacggctacgggcggcgccacctgcagccgcacgatgcgccgggccacggcgtgagga gggccagcgacccggtgcggacaggctccgagggcctggccctgcctcgtgtgccgcgcttcagcagcctcagcagctgcaacccc ccggcgatggccacgtccgcggagaagcgcagtctcgtgcttcagaattacacgcggcccgagggcggccagtcccgaaacttcca ctcgtcccctgtcctcccagcatcaccgagaacgtcaccctggagtccctgaccatggacgctgatgccaacctgaacgatgagg atttcctgccggacgacgtggtgcagtatttaaattcccagaaccaagcagggtacgagcagcacttccccagcgccctcccggac gacagcaaagtgccccacgggcccggtgactttgacgcgcccgggctgccagacagccacgctggccagcagttccatgccctcga gcagccctgccccgagggcagcaaaaccgacctgcccattcagtggaacgaagtcagctccggaagcgccgacctgtcctcctcca agctcaagtgtgggccgcggcccgctgtgccgcagactcgcgcctttgggttctgcaacggcatggtcgtccacccgcagaacccc ttgaggagcgggcctgctggggctatcagacccttcggggagaacagcaaccccatcggtggcccagagcacttgatgctccacaa cagccccggaagtggcaccagtggaaacgccttccatgaacagccctgtaaggccccgcagtatgggaactgtctcaacaggcagc cagtggcccctggtgcactcgacggtgcctgtggtgcgggattcaagcctcaaagctgaagagcaccccatgcaagggagcggg ggccagctgaatttcggcctgccggtagcgccaaatgagtcagctggcagcatggtgaatggcatgcagaaccaggacccagtggg acaggggtacctggctcaccagctcctcggcgacagcatgcagcacccggggggcaggccgccccggtcagcagatgcttgggcaga ttagtgctacctcacacatcaacatctaccaagggccagagagctgcctgccaggggctcacggcatgggcagccagccgtcaagc ttggcagttgtcaggggctaccagccatgtgccagctttgggggcagcaggcgccaggctatgccgagggacagccttgctctgca gtcaggacagctcagtgacacaagtcagacctgcagggtgaatggtatcaagatggagatgaaagggcagccccatccgctgtgct -continued

```
ctaatctgcagaattactctggtcagttctatgaccaaaccgtgggcttcagtcagcaagacacgaaagctggttcattctctatt tcagacgccagctgcctgctacaggggaccagcgccaaaaactctgagttactttccccaggtgctaatcaggtgacaagcacagt ggacagcctcgacagccatgacctggaaggggtacagattgacttcgatgccatcatagacgatggggaccactccagcctgatgt cgggggccctgagcccaagtatcattcagaacctttcccatagctcctcccgcctcaccacgcctcgggcgtccctcccattccca gcgctgtccatgagcaccaccaacatggctatcggggacatgagttctttgctgacctccctagcggaagaaagcaaattccttgc agttatgcaatag
```

Gli3 amino acid sequence - NP_000159.3

(SEQ ID NO: 12)

MEAQSHSSTTTEKKKVENSIVKCSTRTDVSEKAVASSTTSNEDESPGQTYHRERRNAITMQPQNVQGLSKVSEEPSTSSDERASLI
KKEIHGSLPHVAEPSVPYRGTVFAMDPRNGYMEPHYHPPHLFPAFHPPVPIDARHHEGRYHYDPSPIPPLHMTSALSSSPTYPDLP
FIRISPHRNPTAASESPFSPPHPYINPYMDYIRSLHSSPSLSMISATRGLSPTDAPHAGVSPAEYYHQMALLTGQRSPYADIIPSA
ATAGTGAIHMEYLHAMDSTRFSSPRLSARPSRKRTLSISPLSDHSFDLQTMIRTSPNSLVTILNNSRSSSSASGSYGHLSASAISP
ALSFTYSSAPVSLHMHQQILSRQQSLGSAFGHSPPLIHPAPTFPTQRPIPGIPTVLNPVQVSSGPSESSQNKPTSESAVSSTGDPM
HNKRSKIKPDEDLPSPGARGQQEQPEGTTLVKEEGDKDESKQEPEVIYETNCHWEGCAREFDTQEQLVHHINNDHIHGEKKEFVCR
WLDCSREQKPFKAQYMLVVHMRRHTGEKPHKCTFEGCTKAYSRLENLKTHLRSHTGEKPYVCEHEGCNKAFSNASDRAKHQNRTHS
NEKPYVCKIPGCTKRYTDPSSLRKHVKTVHGPEAHVTKKQRGDIHPRPPPPRDSGSHSQSRSPGRPTQGALGEQQDLSNTTSKREE
CLQVKTVKAEKPMTSQPSPGGQSSCSSQQSPISNYSNSGLELPLTDGGSIGDLSAIDETPIMDSTISTATTALALQARRNPAGTKW
MEHVKLERLKQVNGMFPRLNPILPPKAPAVSPLIGNTQSNNTCSLGGPMTLLPGRSDLSGVDVTMLNMLNRRDSSASTISSAYLS
SRRSSGISPCFSSRRSSEASQAEGRPQNVSVADSYDPISTDASRRSSEASQSDGLPSLLSLTPAQQYRLKAKYAAATGGPPPTPLP
NMERMSLKTRLALLGDALEPGVALPPVHAPRRCSDGGAHGYGRRHLQPHDAPGHGVRRASDPVRTGSEGLALPRVPRFSSLSSCNP
PAMATSAEKRSLVLQNYTRPEGGQSRNFHSSPCPPSITENVTLESLTMDADANLNDEDFLPDDVVQYLNSQNQAGYEQHFPSALPD
DSKVPHGPGDFDAPGLPDSHAGQQFHALEQPCPEGSKTDLPIQWNEVSSGSADLSSSKLKCGPRPAVPQTRAFGFCNGMVVHPQNP
LRSGPAGGYQTLGENSNPYGGPEHLMLHNSPGSGTSGNAFHEQPCKAPQYGNCLNRQPVAPGALDGACGAGIQASKLKSTPMQGSG
GQLNFGLPVAPNESAGSMVNGMQNQDPVGQGYLAHQLLGDSMQHPGAGRPGQQMLGQISATSHINIYQPESCLPGAHGMGSQPSS
LAVVRGYQPCASFGGSRRQAMPRDSLALQSGQLSDTSQTCRVNGIKMEMKGQPHPLCSNLQNYSGQFYDQTVGFSQQDTKAGSFSI
SDASCLLQGTSAKNSELLSPGANQVTSTVDSLDSHDLEGVQIDFDAIIDDGDHSSLMSGALSPSIIQNLSHSSSRLTTPRASLPFP
ALSMSTTNMAIGDMSSLLTSLAEESKFLAVMQ

Sonic Hh nucleotide sequence - NM_000193.2

(SEQ ID NO: 13)

```
atgctgctgctggcgagatgtctgctgctagtcctcgtctcctcgctgctggtatgctcgggactggcgtgcggaccgggcagggg gttcgggaagaggaggcaccccaaaaagctgacccctttagcctacaagcagtttatccccaatgtggccgagaagaccctaggcg ccagcggaaggtatgaagggaagatctccagaaactccgagcgatttaaggaactcacccccaattacaaccccgacatcatattt aaggatgaagaaaacaccggagcggacaggctgatgactcagaggtgtaaggacaagttgaacgctttggccatctcggtgatgaa ccagtggccaggagtgaaactgcgggtgaccgagggctgggacgaagatggccaccactcagaggagtctctgcactacgagggcc gcgcagtggacatcaccacgtctgaccgcgaccgcagcaagtacggcatgctggcccgcctggcggtggaggccggcttcgactgg gtgtactacgagtccaaggcacatatccactgctcggtgaaagcagagaactcggtggcggccaaatcgggaggctgcttcccggg ctcggccacggtgcacctggagcagggcggcaccaagctggtgaaggacctgagccccggggaccgcgtgctggcggcggacgacc agggccggctgctctacagcgacttcctcactttcctggaccgcgacgacggcgccaagaaggtcttctacgtgatcgagacgcgg gagccgcgcgagcgcctgctgctcaccgccgcgcacctgctctttgtggcgccgcacaacgactcggccaccgggagcccgaggc gtcctcgggctcggggccgccttccggggcgcactgggcctcggcgctgttcgccagccgcgtgcgcccgggccagcgcgtgt acgtggtggccgagcgtgacggggaccgccggctcctgcccgccgctgtgcacagcgtgaccctaagcgaggaggccgcgggcgcc tacgcgccgctcacggcccagggcaccattctcatcaaccgggtgctggcctcgtgctacggggtcatcgaggagcacagctgggc gcaccggccttcgcgcccttccgcctggcgcacgcgctcctggctgcactggcccgcgcgcacggaccgcggcggggacagcg

```

-continued

```
gcggcggggaccgcgggggcggcggcggcagagtagccctaaccgctccaggtgctgccgacgctccgggtgcggggccaccgcg ggcatccactggtactcgcagctgctctaccaaataggcacctggctcctggacagcgaggccctgcacccgctgggcatggcggt caagtccagctga
```

Sonic Hh amino acid sequence - NP_000184.1

(SEQ ID NO: 14)

```
MLLLARCLLLVLVSSLLVCSGLACGPGRGFGKRRHPKKLTPLAYKQFIPNVAEKTLGASGRYEGKISRNSERFKELTPNYNPDIIF

KDEENTGADRLMTQRCKDKLNALAISVMNQWPGVKLRVTEGWDEDGHHSEESLHYEGRAVDITTSDRDRSKYGMLARLAVEAGFDW

VYYESKAHIHCSVKAENSVAAKSGGCFPGSATVHLEQGGTKLVKDLSPGDRVLAADDQGRLLYSDFLTFLDRDDGAKKVFYVIETR

EPRERLLLTAAHLLFVAPHNDSATGEPEASSGSGPPSGGALGPRALFASRVRPGQRVYVVAERDGDRRLLPAAVHSVTLSEEAAGA

YAPLTAQGTILINRVLASCYAVIEEHSWAHRAFAPFRLAHALLAALAPARTDRGGDSGGGDRGGGGGRVALTAPGAADAPGAGATA

GIHWYSQLLYQIGTWLLDSEALHPLGMAVKSS
```

Indian Hh nucleotide sequence - NM_002181.3

(SEQ ID NO: 15)

```
atgtctcccgcccggctccggccccgactgcacttctgcctggtcctgttgctgctgctggtggtgccggcggcatgggctgcgg gccgggtcgggtggtgggcagccgccggcgaccgccacgcaaactcgtgccgctcgcctacaagcagttcagccccaatgtgcccg agaagaccctgggcgccagcggacgctatgaaggcaagatcgctcgcagctccgagcgcttcaaggagctcaccccaattacaat ccagacatcatcttcaaggacgaggagaacacaggcgccgaccgcctcatgacccagcgctgcaaggaccgcctgaactcgctggc tatctcggtgatgaaccagtggcccggtgtgaagctgcgggtgaccgagggctgggacgaggacggccaccactcagaggagtccc tgcattatgagggccgcgcggtggacatcaccacatcagaccgcgaccgcaataagtatggactgctggcgcgcttggcagtggag gccggctttgactgggtgtattacgagtcaaaggccacgtgcattgctccgtcaagtccgagcactcggccgcagccaagacggg cggctgcttccctgccggagcccaggtacgcctggagagtggggcgcgtgtggccttgtcagccgtgaggccgggagaccgtgtgc tggccatggggaggatgggagcccaccttcagcgatgtgctcatttcctggaccgcgagcctcacaggctgagagccttccag gtcatcgagactcaggaccccccacgccgcctggcactcacacccgctcacctgctctttacggctgacaatcacacggagccggc agcccgcttccgggccacatttgccagccacgtgcagcctggccagtacgtgctggtggctggggtgccaggcctgcagcctgccc gcgtggcagctgtctctacacacgtggccctcggggcctacgccccgctcacaaagcatgggacactggtggtggaggatgtggtg gcatcctgcttcgcggccgtggctgaccaccacctggctcagttggccttctggcccctgagactctttcacagcttggcatgggg cagctggaccccggggagggtgtgcattggtaccccagctgctctaccgcctggggcgtctcctgctagaagagggcagcttcc acccactgggcatgtccggggcagggagctga
```

Indian Hh amino acid sequence - NP_002172.2

(SEQ ID NO: 16)

```
MSPARLRPRLHFCLVLLLLLVVPAAWGCGPGRVVGSRRRPPRKLVPLAYKQFSPNVPEKTLGASGRYEGKIARSSERFKELTPNYN

PDIIFKDEENTGADRLMTQRCKDRLNSLAISVMNQWPGVKLRVTEGWDEDGHHSEESLHYEGRAVDITTSDRDRNKYGLLARLAVE

AGFDWVYYESKAHVHCSVKSEHSAAAKTGGCFPAGAQVRLESGARVALSAVRPGDRVLAMGEDGSPTFSDVLIFLDREPHRLRAFQ

VIETQDPPRRLALTPAHLLFTADNHTEPAARFRATFASHVQPGQYVLVAGVPGLQPARVAAVSTHVALGAYAPLTKHGTLVVEDVV

ASCFAAVADHHLAQLAFWPLRLFHSLAWGSWTPGEGVHWYPQLLYRLGRLLLEEGSFHPLGMSGAGS
```

Desert Hh nucleotide sequence - NM_021044.2

(SEQ ID NO: 17)

```
atggctctcctgaccaatctactgcccctgtgctgcttggcacttctggcgctgccagcccagagctgcgggccgggccggggcc ggttggccggcgccgctatgcgcgcaagcagctcgtgccgctactctacaagcaatttgtgcccggcgtgccagagcggaccctgg gcgccagtgggccagcggaggggagggtggcaaggggctccgagcgcttccgggacctcgtgcccaactacaaccccgacatcatc ttcaaggatgaggagaacagtggagccgaccgcctgatgacccagcgttgtaaggagcgggtgaacgctttggccattgccgtgat gaacatgtggcccggagtgcgcctacgagtgactgagggctgggacgaggacggccaccacgctcaggattcactccactacgaag gccgtgctttggacatcactacgtctgaccgcgaccgcaacaagtatgggttgctggcgcgcctcgcagtggaagccggcttcgac tgggtctactacgagtcccgcaaccacgtccacgtgtcggtcaaagctgataactcactggcggtccgggcgggcggctgctttcc
```

-continued

```
gggaaatgcaactgtgcgcctgtggagcggcgagcggaaagggctgcgggaactgcaccgcggagactgggttttggcggccgatg cgtcaggccgggtggtgcccacgccggtgctgctcttcctggaccgggacttgcagcgccgggcttcatttgtggctgtggagacc gagtggcctccacgcaaactgttgctcacgccctggcacctggtgtttgccgctcgagggccggcgcccgcgccaggcgactttgc accggtgttcgcgcgccggctacgcgctggggactcggtgctggcgcccggcggggatgcgcttcggccagcgcgcgtggcccgtg tggcgcgggaggaagccgtgggcgtgttcgcgccgctcaccgcgcacgggacgctgctggtgaacgatgtcctggcctcttgctac gcggttctggagagtcaccagtgggcgcaccgcgcttttgccccccttgagactgctgcacgcgctaggggcgctgctccccggcgg ggccgtccagccgactggcatgcattggtactctcggctcctctaccgcttagcggaggagctactgggctga
```

Desert Hh amino acid sequence - NP_066382.1

(SEQ ID NO: 18)

MALLTNLLPLCCLALLALPAQSCGPGRGPVGRRRYARKQLVPLLYKQFVPGVPERTLGASGPAEGRVARGSERFRDLVPNYNPDII
FKDEENSGADRLMTERCKERVNALAIAVMNMWPGVRLRVTEGWDEDGHHAQDSLHYEGRALDITTSDRDRNKYGLLARLAVEAGFD
WVYYESRNHVHVSVKADNSLAVRAGGCFPGNATVRLWSGERKGLRELHRGDWVLAADASGRVVPTPVLLFLDRDLQRRASFVAVET
EWPPRKLLLTPWHLVFAARGPAPAPGDFAPVFARRLRAGDSVLAPGGDALRPARVARVAREEAVGVFAPLTAHGTLLVNDVLASCY
AVLESHQWAHRAFAPLRLLHALGALLPGGAVQPTGMHWYSRLLYRLAEELLG

Hhip nucleotide sequence - NM_022475.2

(SEQ ID NO: 19)

```
atgctgaagatgctctcctttaagctgctgctgctggccgtggctctgggcttctttgaaggagatgctaagtttggggaaagaaa cgaagggagcggagcaaggaggagaaggtgcctgaatgggaaccccccgaagcgcctgaaaaggagagacaggaggatgatgtccc agctggagctgctgagtgggggagagatgctgtgcggtggcttctaccctcggctgtcctgctgcctgcggagtgacagcccgggg ctagggcgcctggagaataagatattttctgttaccaacaacacagaatgtgggaagttactggaggaaatcaaatgtgcactttg ctctccacattctcaaagcctgttccactcacctgagagagaagtcttggaaagagacctagtacttcctctgctctgcaaagact attgcaaagaattcttttacacttgccgaggccatattccaggtttccttcaaacaactgcggatgagttttgcttttactatgca agaaaagatggtgggttgtgctttccagattttccaagaaaacaagtcagaggaccagcatctaactacttggaccagatggaaga atatgacaaagtggaagagatcagcagaaagcacaaacacaactgcttctgtattcaggaggttgtgagtgggctgcggcagcccg ttggtgccctgcatagtggggatggctcgcaacgtctcttcattctggaaaaagaaggttatgtgaagatacttacccctgaagga gaaattttcaaggagccttatttggacattcacaaacttgttcaaagtggaataaagggaggagatgaaagaggactgctaagcct cgcattccatcccaattacaagaaaaatggaaagttgtatgtgtcctataccaccaaccaagaacggtgggctatcgggcctcatg accacattcttagggttgtggaatacacagtatccagaaaaaatccacaccaagttgatttgagaacagccagagtctttcttgaa gttgcagaactccacagaaagcatctggggaggacaactgctcttttggccctgacggcttttgtacatcattcttggtgatggga tgattacactggatgatatggaagaaatggatgggttaagtgatttcacaggctcagtgctacggctggatgtggacacagacatgt gcaacgtgccttattccataccaaggagcaacccacacttcaacagcaccaaccagcccccgaagtgtttgctcatgggctccac gatccaggcagatgtgctgtgatagacatccccactgatataaacatcaatttaacgatactgtgttcagactccaatgaaaaaa cagatcatcagccagaattctacagataataaaggggaaagattatgaaagtgagccatcacttttagaattcaagccattcagta atggtcctttggttggtggatttgtataccggggctgccagtcagaaagattgtatggaagctacgtgtttggagatcgtaatggg aatttcctaactctccagcaaagtcctgtgacaaagcagtggcaagaaaaaccactctgtctcggcactagtgggtcctgtagagg ctacttttccggtcacatcttgggatttggagaagatgaactaggtgaagtttacattttatcaagcagtaaaagtatgacccaga ctcacaatggaaaactctacaaaattgtagatcccaaaagacctttaatgcctgaggaatgcagagccacggtacaacctgcacag acacttgacttcagagtgctccaggctctgtcgaaacggctactgcaccccacgggaaagtgctgctgcagtccaggctggggaggg ggacttctgcagaactgcaaaatgtgagccagcatgtcgtcatggaggtgtctgtgttagaccgaacaagtgcctctgtaaaaaag gatatcttggtcctcaatgtgaacaagtggacagaaacatccgcagagtgaccagggcaggtattcttgatcagatcattgacatg acatcttacttgctggatctaacaagttacattgtatag
```

Hhip amino acid sequence - NP_071920.1

(SEQ ID NO: 20)

MLKMLSFKLLLLAVALGFFEGDAKFGERNEGSGARRRRCLNGNPPKRLKRRDRRMMSQLELLSGGEMLCGGFYPRLSCCLRSDSPG
LGRLENKIFSVTNNTECGKLLEEIKCALCSPHSQSLFHSPEREVLERDLVLPLLCKDYCKEFFYTCRGHIPGFLQTTADEFCFYYA
RKDGGLCFPDFPRKQVRGPASNYLDQMEEYDKVEEISRKHKHNCFCIQEVVSGLRQPVGALHSGDGSQRLFILEKEGYVKILTPEG
EIFKEPYLDIHKLVQSGIKGGDERGLLSLAFHPNYKKNGKLYVSYTTNQERWAIGPHDHILRVVEYTVSRKNPHQVDLRTARVFLE
VAELHRKHLGGQLLFGPDGFLYIILGDGMITLDDMEEMDGLSDFTGSVLRLDVDTDMCNVPYSIPRSNPHFNSTNQPPEVFAHGLH
DPGRCAVDRHPTDININLTILCSDSNGKNRSSARILQIIKGKDYESEPSLLEFKPFSNGPLVGGFVYRGCQSERLYGSYVFGDRNG
NFLTLQQSPVTKQWQEKPLCLGTSGSCRGYFSGHILGFGEDELGEVYILSSSKSMTQTHNGKLYKIVDPKRPLMPEECRATVQPAQ
TLTSECSRLCRNGYCTPTGKCCCSPGWEGDFCRTAKCEPACRHGGVCVRPNKCLCKKGYLGPQCEQVDRNIRRVTRAGILDQIIDM
TSYLLDLTSYIV

Ptc1 nucleotide sequence - NM_001083602.1

(SEQ ID NO: 21)

tggggaaggctactggccggaaagcgccgctgtggctgagagcgaagtttcagagactcttatttaaactggggttgttacattcaa
aaaaactgcggcaagttcttggttgtgggcctcctcatatttggggccttcgcggtgggattaaaagcagcgaacctcgagaccaa
cgtggaggagctgtgggtgaagttggaggacgagtaagtcgtgaattaaattatactcgccagaagattggagaagaggctatgt
ttaatcctcaactcatgatacagacccctaaagaagaaggtgctaatgtcctgaccacagaagcgctcctacaacacctggactcg
gcactccaggccagccgtgtccatgtatacatgtacaacaggcagtggaaattgaacatttgtgttacaaatcaggagagcttat
cacagaaacaggttacatggatcagataatagaatatctttacccttgtttgattattacacctttggactgcttctgggaagggg
cgaaattacagtctgggacagcataccatcctaggtaaacctccttttgcggtggacaaacttcgaccctttggaattcctggaagag
ttaaagaaaataaactatcaagtggacagctgggaggaaatgctgaataaggctgaggttggtcatggttacatggaccgcccctg
cctcaatccggccgatccagactgccccgccacagccccaacaaaaattcaaccaaacctcttgatatggcccttgttttgaatg
gtggatgtcatggcttatccagaaagtatatgcactggcaggaggagttgattgtgggtggcacagtcaagaacagcactggaaaa
ctcgtcagcgcccatgccctgcagaccatgttccagttaatgactcccaagcaaatgtacgagcacttcaaggggtacgagtatgt
ctcacacatcaactggaacgaggacaaagcggcagccatcctggaggcctggcagaggacatatgtggaggtggttcatcagagtg
tcgcacagaactccactcaaaaggtgctttccttcaccaccacgaccctggacgacatcctgaaatccttctctgacgtcagtgtc
atccgcgtggccagcggctacttactcatgctcgccatgcctgtctaaccatgctgcgctgggactgctccaagtcccagggtgc
cgtggggctggctggcgtcctgctggttgcactgtcagtggctgcaggactgggcctgtgctcattgatcggaatttcctttaacg
ctgcaacaactcaggttttgccatttctcgctcttggtgttggtgtggatgatgttttcttctggcccacgccttcagtgaaaca
ggacagaataaaagaatccctttgaggacaggaccggggagtgcctgaagcgcacaggagccagcgtggccctcacgtccatcag
caatgtcacagccttcttcatggccgcgttaatcccaattcccgctctgcgggcgttctccctccaggcagcggtagtagtggtgt
tcaattttgccatggttctgctcattttcctgcaattctcagcatggatttatatcgacgcgaggacaggagactggatattttc
tgctgttttacaagcccctgcgtcagcagagtgattcaggttgaacctcaggcctacaccgacacacgacaatacccgctacag
ccccccacctccctacagcagccacagctttgcccatgaaacgcagattaccatgcagtccactgtccagctccgcacggagtacg
accccacacgcacgtgtactacaccaccgctgagccgcgctccgagatctctgtgcagcccgtcaccgtgacacaggacaccctc
agctgccagagcccagagagcaccagctccacaagggacctgctctcccagttctccgactccagcctccactgcctcgagccccc
ctgtacgaagtggacactctcatcttttgctgagaagcactatgctcctttcctcttgaaaccaaaagccaaggtagtggtgatct
tccttttctgggcttgctggggtcagcctttatggcaccacccgagtgagagacgggctggaccttacggacattgtacctcgg
gaaaccagagaatatgactttattgctgcacaattcaaatacttttctttctacaacatgtatatagtcacccagaaagcagacta
cccgaatatccagcacttactttacgacctacacaggagtttcagtaacgtgaagtatgtcatgttggaagaaaacaaacagcttc
ccaaaatgtggctgcactacttcagagactggcttcagggacttcaggatgcatttgacagtgactgggaaaccgggaaaatcatg
ccaaacaattacaagaatggatcagacgatggagtccttgcctacaaaactcctggtgcaaaccggcagccgcgataagcccatcga -continued

```
catcagccagttgactaaacagcgtctggtggatgcagatggcatcattaatcccagcgctttctacatctacctgacggcttggg tcagcaacgaccccgtcgcgtatgctgcctcccaggccaacatccggccacaccgaccagaatgggtccacgacaaagccgactac atgcctgaaacaaggctgagaatcccggcagcagagcccatcgagtatgcccagttccctttctacctcaacggcttgcgggacac ctcagactttgtggaggcaattgaaaaagtaaggaccatctgcagcaactatacgagcctggggctgtccagttaccccaacggct accccttcctcttctgggagcagtacatcggcctccgccactggctgctgctgttcatcagcgtggtgttggcctgcacattcctc gtgtgcgctgtcttccttctgaaccccggacggccgggatcattgtgatggtcctggcgctgatgacggtcgagctgttcggcat gatgggcctcatcggaatcaagctcagtgccgtgccgtggtcatcctgatcgcttctgttggcataggagtggagttcaccgttc acgttgctttggccttcctgacggccatcggcgacaagaaccgcagggctgtgcttgccctggagcacatgtttgcaccgtcctg gatggcgccgtgtccactctgctgggagtgctgatgctggcgggatctgagttcgacttcattgtcaggtatttctttgctgtgct ggcgatcctcaccatcctcggcgttctcaatgggctggttttgcttcccgtgcttttgtctttctttggaccatatcctgaggtgt ctccagccaacggcttgaaccgctgcccacaccctcccctgagccaccccccagcgtggtccgcttcgccatgccgcccggccac acgcacagcgggtctgattcctccgactcggagtatagttcccagacgacagtgtcaggcctcagcgaggagcttcggcactacga ggcccagcagggcgcgggaggccctgcccaccaagtgatcgtggaagccacagaaaacccgtcttcgcccactccactgtggtcc atcccgaatccaggcatcacccaccctcgaacccgagacagcagccccacctggactcagggtccctgcctcccggacggcaaggc cagcagcccgcagggacccccccagagaaggcttgtggccacccccctacagaccgcgcagagacgcttttgaaatttctactga agggcattctggccctagcaatagggcccgctggggccctcgcggggcccgttctcacaaccctcggaacccagcgtccactgcca tgggcagctccgtgccggctactgccagcccatcaccactgtgacggcttctgcctccgtgactgtcgccgtgcacccgccgcct gtccctgggcctggcggaaccccgaggggactctgcccaggctaccctgagactgaccacggcctgtttgaggacccccacgt gccttccacgtccggtgtgagaggagggattcgaaggtggaagtcattgagctgcaggacgtggaatgcgaggagaggccccggg gaagcagctccaactga
```

Ptc1 amino acid sequence - NP_001077071.1

(SEQ ID NO: 22)

MGKATGRKAPLWLRAKFQRLLFKLGCYIQKNCGKFLVVGLLIFGAFAVGLKAANLETNVEELWVEVGGRVSRELNYTRQKIGEEAM

FNPQLMIQTPKEEGANVLTTEALLQHLDSALQASRVHVYMYNRQWKLEHLCYKSGELITETGYMDQIIEYLYPCLIITPLDCFWEG

AKLQSGTAYLLGKPPLRWTNFDPLEFLEELKKINYQVDSWEEMLNKAEVGHGYMDRPCLNPADPDCPATAPNKNSTKPLDMALVLN

GGCHGLSRKYMHWQEELIVGGTVKNSTGKLVSAHALQTMFQLMTPKQMYEHFKGYEYVSHINWNEDKAAAILEAWQRTYVEVVHQS

VAQNSTQKVLSFTTTTLDDILKSFSDVSVIRVASGYLLMLAYACLTMLRWDCSKSQGAVGLAGVLLVALSVAAGLGLCSLIGISFN

AATTQVLPFLALGVGVDDVFLLAHAFSETGQNKRIPFEDRTGECLKRTGASVALTSISNVTAFFMAALIPIPALRAFSLQAAVVVV

FNFAMVLLIFPAILSMDLYRREDRRLDIFCCFTSPCVSRVIQVEPQAYTDTHDNTRYSPPPPYSSHSFAHETQITMQSTVQLRTEY

DPHTHVYYTTAEPRSEISVQPVTVTQDTLSCQSPESTSSTRDLLSQFSDSSLHCLEPPCTKWTLSSFAEKHYAPFLLKPKAKVVVI

FLFLGLLGVSLYGTTRVRDGLDLTDIVPRETREYDFIAAQFKYFSFYNMYIVTQKADYPNIQHLLYDLHRSFSNVKYVMLEENKQL

PKMWLHYFRDWLQGLQDAFDSDWETGKIMPNNYKNGSDDGVLAYKLLVQTGSRDKPIDISQLTKQRLVDADGIINPSAFYIYLTAW

VSNDPVAYAASQANIRPHRPEWVHDKADYMPETRLRIPAAEPIEYAQFPFYLNGLRDTSDFVEAIEKVRTICSNYTSLGLSSYPNG

YPFLFWEQYIGLRHWLLLFISVVLACTFLVCAVFLLNPWTAGIIVMVLALMTVELFGMMGLIGIKLSAVPVVILIASVGIGVEFTV

HVALAFLTAIGDKNRRAVLALEHMFAPVLDGAVSTLLGVLMLAGSEFDFIVRYFFAVLAILTILGVLNGLVLLPVLLSFFGPYPEV

SPANGLNRLPTPSPEPPPSVVRFAMPPGHTHSGSDSSDSEYSSQTTVSGLSEELRHYEAQQGAGGPAHQVIVEATENPVFAHSTVV

HPESRHHPPSNPRQQPHLDSGSLPPGRQGQQPRRDPPREGLWPPPYRPRRDAFEISTEGHSGPSNRARWGPRGARSHNPRNPASTA

MGSSVPGYCQPITTVTASASVTVAVHPPPVPGPGRNPRGGLCPGYPETDHGLFEDPHVPFHVRCERRDSKVEVIELQDVECEERPR

GSSSN

Ptc2 nucleotide sequence - AF091501.1

(SEQ ID NO: 23)

```
atgactcgatcgccgccccctcagagagctgccccgagttacacaccccagctcgaaccgcagcacccagatcctagctgggag cctgaaggctccactctggcttcgtgcttacttccagggcctgctcttctctctgggatgcgggatccagagacattgtggcaaag
```

-continued

```
tgctctttctgggactgttggcctttggggccctggcattaggtctccgcatggccattattgagacaaacttggaacagctctgg
gtagaagtgggcagccgggtgagccaggagctgcattacaccaaggagaagctgggggaggaggctgcatacacctctcagatgct
gatacagaccgcacgccaggagggagagaacatcctcacacccgaagcacttggcctccacctccaggcagccctcactgccagta
aagtccaagtatcactctatgggaagtcctgggatttgaacaaaatctgctacaagtcaggagttcccttattgaaaatggaatg
attgagtggatgattgagaagctgtttccgtgcgtgatcctcaccccctcgactgcttctgggagggagccaaactccaaggggg
ctccgcctacctgcccggccgcccggatatccagtggaccaacctggatccagagcagctgctggaggagctgggtcccttgcct
cccttgagggcttccgggagctgctagacaaggcacaggtgggccaggcctacgtggggcggccctgtctgcaccctgatgacctc
cactgcccacctagtgcccccaaccatcacagcaggcaggctcccaatgtggctcacgagctgagtgggggctgccatggcttctc
ccacaaattcatgcactggcaggaggaattgctgctgggaggcatggccagagaccccaaggagagctgctgagggcagaggccc
tgcagagcaccttcttgctgatgagtccccgccagctgtacgagcatttccggggtgactatcagacacatgacattggctggagt
gaggagcaggccagcacagtgctacaagcctggcagcggcgctttgtgcagctggcccaggaggccctgcctgagaacgcttccca
gcagatccatgccttctcctccaccaccctggatgacatcctgcatgcgttctctgaagtcagtgctgcccgtgtggtgggaggct
atctgctcatgctggcctatgcctgtgtgaccatgctgcggtgggactgcgcccagtcccagggttccgtgggccttgccggggta
ctgctggtggccctggcggtggcctcaggccttgggctctgtgccctgctcggcatcaccttcaatgctgccactacccaggtgct
gcctttcttggctctgggaatcggcgtggatgacgtattcctgctggcgcatgccttcacagaggctctgcctggcacccctctcc
aggagcgcatgggcgagtgtctgcagcgcacgggcaccagtgtcgtactcacatccatcaacaacatggccgccttcctcatggct
gccctcgttcccatccctgcgctgcgagccttctccctacaggcggccatagtggttggctgcacctttgtagccgtgatgcttgt
cttcccagccatcctcagcctggacctacggcggcgccactgccagcgccttgatgtgctctgctgcttctccagtccctgctctg
ctcaggtgattcagatcctgccccaggagctgggggacgggacagtaccagtgggcattgcccacctcactgccacagttcaagcc
tttacccactgtgaagccagcagccagcatgtggtcaccatcctgcctcccaagcccacctggtgcccccaccttctgacccact
gggctctgagctcttcagccctggagggtccacacgggaccttctaggccaggaggaggagacaaggcagaaggcagcctgcaagt
ccctgccctgtgccgctggaatcttgcccatttcgcccgctatcagtttgcccgttgctgctccagtcacatgccaaggccatc
gtgctggtgctctttggtgctcttctgggcctgagcctctacggagccaccttggtgcaagacggcctggccctgacggatgtggt
gcctcggggcaccaaggagcatgccttcctgagcgcccagctcaggtacttctccctgtacgaggtggccctggtgacccagggtg
gctttgactacgccattcccaacgcgccctctttgatctgcaccagcgcttcagttccctcaaggcggtgctgcccccaccggcc
acccaggcaccccgcacctggctgcactattaccgcaactggctacagggaatccaggctgcctttgaccaggactgggcttctgg
gcgcatcacccgccactcgtaccgcaatggctctgaggatggggccctggcctacaagctgctcatccagactggagacgcccagg
agcctctggatttcagccagctgaccacaaggaagctggtggacagagagggactgattccacccgagctcttctacatggggctg
accgtgtgggtgagcagtgaccccctgggtctggcagcctcacaggccaacttctacccccccacctcctgaatggctgcacgacaa
atacgacaccacgggggagaaccttcgcatcccgccagctcagcccttggagtttgcccagttccccttcctgctgcgtggcctcc
agaagactgcagactttgtggaggccatcgagggggcccgggcagcatgcgcagaggccggccaggctggggtgcacgcctacccc
agcggctcccccttcctcttctgggaacagtatctgggcctgcggcgctgcttcctgctggccgtctgcatcctgctggtgtgcac
tttcctcgtctgtgctctgctgctcctcaaccccctggacggctggcctcatagtgctggtcctggcgatgatgacagtggaactct
ttggtatcatgggtttcctgggcatcaagctgagtgccatccccgtggtgatccttgtggcctctgtaggcattggcgttgagttc
acagtccacgtggctctgggcttcctgaccacccagggcagccggaacctgcggggccgcccatgcccttgagcacacatttgcccc
cgtgaccgatggggccatctccacattgctgggtctgctcatgcttgctggttcccactttgacttcattgtaaggtacttctttg
cggcgctgacagtgctcacgctcctgggcctcctccatggactcgtgctgctgcctgtgctgctgtccatcctgggcccgccgcca
gaggtgatacagatgtacaaggaaagcccagagatcctgagtccaccagctccacagggaggcgggcttaggtgggggcatcctc
ctccctgccccagagctttgccagagtgactacctccatgaccgtggccatccaccaccccccctgcctggtgcctacatccatc
cagcccctgatgagccccttggtccctgctgccactagctctggcaacctcagttccaggggaccaggtccagccactgggtga
```

Ptc2 amino acid sequence - AAC79847.1

(SEQ ID NO: 24)

MTRSPPLRELPPSYTPPARTAAPQILAGSLKAPLWLRAYFQGLLFSLGCGIQRHCGKVLFLGLLAFGALALGLRMAIIETNLEQLW
VEVGSRVSQELHYTKEKLGEEAAYTSQMLIQTARQEGENILTPEALGLHLQAALTASKVQVSLYGKSWDLNKICYKSGVPLIENGM
IEWMIEKLFPCVILTPLDCFWEGAKLQGGSAYLPGRPDIQWTNLDPEQLLEELGPFASLEGFRELLDKAQVGQAYVGRPCLHPDDL
HCPPSAPNHHSRQAPNVAHELSGGCHGFSHKFMHWQEELLLGGMARDPQGELLRAEALQSTFLLMSPRQLYEHFRGDYQTHDIGWS
EEQASTVLQAWQRRFVQLAQEALPENASQQIHAFSSTTLDDILHAFSEVSAARVVGGYLLMLAYACVTMLRWDCAQSQGSVGLAGV
LLVALAVASGLGLCALLGITFNAATTQVLPFLALGIGVDDVFLLAHAFTEALPGTPLQERMGECLQRTGTSVVLTSINNMAAFLMA
ALVPIPALRAFSLQAAIVVGCTFVAVMLVFPAILSLDLRRRHCQRLDVLCCFSSPCSAQVIQILPQELGDGTVPVGIAHLTATVQA
FTHCEASSQHVVTILPPQAHLVPPPSDPLGSELFSPGGSTRDLLGQEEETRQKAACKSLPCARWNLAHFARYQFAPLLLQSHAKAI
VLVLFGALLGLSLYGATLVQDGLALTDVVPRGTKEHAFLSAQLRYFSLYEVALVTQGGFDYAHSQRALFDLHQRFSSLKAVLPPPA
TQAPRTWLHYYRNWLQGIQAAFDQDWASGRITRHSYRNGSEDGALAYKLLIQTGDAQEPLDFSQLTTRKLVDREGLIPPELFYMGL
TVWVSSDPLGLAASQANFYPPPPEWLHDKYDTTGENLRIPPAQPLEFAQFPFLLRGLQKTADFVEAIEGARAACAEAGQAGVHAYP
SGSPFLFWEQYLGLRRCFLLAVCILLVCTFLVCALLLLNPWTAGLIVLVLAMMTVELFGIMGFLGIKLSAIPVVILVASVGIGVEF
TVHVALGFLTTQGSRNLRAAHALEHTFAPVTDGAISTLLGLLMLAGSHFDFIVRYFFAALTVLTLLGLLHGLVLLPVLLSILGPPP
EVIQMYKESPEILSPPAPQGGGLRWGASSSLPQSFARVTTSMTVAIHPPPLPGAYIHPAPDEPPWSPAATSSGNLSSRGPGPATG

Smo nucleotide sequence - NM_005631.4

(SEQ ID NO: 25)

atggccgctgcccgcccagcgcggggccggagctcccgctcctggggctgctgctgctgctgctggggaccgggccgggg
ggcggcctcgagcgggaacgcgaccgggcctgggcctcggagcgcgggcgggagcgcgaggaggagcgcggcggtgactggccctc
cgccgccgctgagccactgcggccgggctgcccctgcgagccgctgcgctacaacgtgtgcctgggctcggtgctgccctacggg
gccacctccacactgctggccggagactcggactcccaggaggaagcgcacggcaagctcgtgctctggtcgggcctccggaatgc
ccccgctgctgggcagtgatccagccctgctgtgtgccgtatacatgcccaagtgtgagaatgaccgggtggagctgcccagcc
gtaccctctgccaggccacccgaggcccctgtgccatcgtggagagggagcggggctggcctgacttcctgcgctgcactcctgac
cgcttccctgaaggctgcacgaatgaggtgcagaacatcaagttcaacagttcaggccagtgcgaagtgcccttggttcggacaga
caaccccaagagctggtacgaggacgtggagggctgcggcatccagtgccagaacccgctcttcacagaggctgagcaccaggaca
tgcacagctacatcgcggccttcggggccgtcacgggcctctgcacgctcttcacccttggccacattcgtggctgactggcggaac
tcgaatcgctaccctgctgttattctcttctacgtcaatgcgtgcttctttgtgggcagcattggctggctggcccagttcatgga
tggtgcccgccgagagatcgtctgccgtgcagatggcaccatgaggcttggggagcccacctccaatgagactctgtcctgcgtca
tcatctttgtcatcgtgtactacgccctgatggctggtgtggtttggtttgtggtcctcacctatgcctggcacacttccttcaaa
gccctgggcaccacctaccagcctctctcgggcaagacctcctacttccacctgctcacctggtcactcccctttgtcctcactgt
ggcaatccttgctgtggcgcaggtggatgggactctgtgagtgggatttgttttgtgggctacaagaactaccgataccgtgcgg
gcttcgtgctggccccaatcggcctggtgctcatcgtgggaggctacttcctcatccgaggagtcatgactctgttctccatcaag
agcaaccaccccgggctgctgagtgagaaggctgccagcaagatcaacgagaccatgctgcgcctgggcattttggcttcctggc
ctttggctttgtgctcattaccttcagctgccacttctacgacttcttcaaccaggctgagtgggagcgcagcttccgggactatg
tgctatgtcaggccaatgtgaccatcgggctgcccaccaagcagcccatccctgactgtgagatcaagaatcgcccgagccttctg
gtggagaagatcaacctgtttgccatgtttggaactggcatcgccatgagcacctgggtctggaccaaggccacgctgctcatctg
gaggcgtacctggtgcaggttgactgggcagagtgacgatgagccaaagcggatcaagaagagcaagatgattgccaaggccttct
ctaagcggcacgagctcctgcagaacccaggccaggagctgtccttcagcatgcacactgtgtcccacgacgggcccgtggcgggc
ttggcctttgacctcaatgagccctcagctgatgtctcctctgcctgggcccagcatgtcaccaagatggtggctcggagaggagc
catactgccccaggatatttctgtcaccccctgtggcaactccagtgcccccagaggaacaagccaacctgtggctggttgaggcag
agatctccccagagctgcagaagcgcctgggccggaagaagaagaggaggaagaggaagaaggaggtgtgcccgctggccgcgccc
cctgagcttcaccccctgcccctgccccagtaccattcctcgactgcctcagctgccccggcagaaatgcctggtggctgcagg -continued tgcctggggagctggggactcttgccgacagggagcgtggaccctggtctccaacccattctgcccagagcccagtcccctcagg atccatttctgccagtgcaccggcccccgtggcatgggctcatggccgccgacagggcctggggcctattcactcccgcaccaac ctgatggacacagaactcatggatgcagactcggacttctga Smo amino acid sequence - NP_005622.1

(SEQ ID NO: 26)

MAAARPARGPELPLLGLLLLLLLGDPGRGAASSGNATGPGPRSAGGSARRSAAVTGPPPPLSHCGRAAPCEPLRYNVCLGSVLPYG

ATSTLLAGDSDSQEEAHGKLVLWSGLRNAPRCWAVIQPLLCAVYMPKCENDRVELPSRTLCQATRGPCAIVERERGWPDFLRCTPD

RFPEGCTNEVQNIKFNSSGQCEVPLVRTDNPKSWYEDVEGCGIQCQNPLFTEAEHQDMHSYIAAFGAVTGLCTLFTLATFVADWRN

SNRYPAVILFYVNACFFVGSIGWLAQFMDGARREIVCRADGTMRLGEPTSNETLSCVIIFVIVYYALMAGVVWFVVLTYAWHTSFK

ALGTTYQPLSGKTSYFHLLTWSLPFVLTVAILAVAQVDGDSVSGICFVGYKNYRYRAGFVLAPIGLVLIVGGYFLIRGVMTLFSIK

SNHPGLLSEKAASKINETMLRLGIFGFLAFGFVLITFSCHFYDFFNQAEWERSFRDYVLCQANVTIGLPTKQPIPDCEIKNRPSLL

VEKINLFAMFGTGIAMSTWVWTKATLLIWRRTWCRLTGQSDDEPKRIKKSKMIAKAFSKRHELLQNPGQELSFSMHTVSHDGPVAG

LAFDLNEPSADVSSAWAQHVTKMVARRGAILPQDISVTPVATPVPPEEQANLWLVEAEISPELQKRLGRKKKRRKRKKEVCPLAPP

PELHPPAPAPSTIPRLPQLPRQKCLVAAGAWGAGDSCRQGAWTLVSNPFCPEPSPPQDPFLPSAPAPVAWAHGRRQGLGPIHSRTN

LMDTELMDADSDF

SuFu nucleotide sequence - NM_016169.3

(SEQ ID NO: 27)

atggcggagctgcggcctagcggcgccccggccccaccgcgcccccggccctggcccgactgccccccggccttcgcttcgct ctttccccgggactgcacgccatctacggagagtgccgccgcctttaccctgaccagccgaacccgctccaggttaccgctatcg tcaagtactggttgggtggcccagacccttggactatgttagcatgtacaggaatgtggggagcccttctgctaacatccccgag cactggcactacatcagcttcggcctgagtgatctctatggtgacaacagagtccatgagtttacaggaacagatggacctagtgg ttttggctttgagttgacctttcgtctgaagagagaaactggggagtctgccccaccaacatggcccgcagagttaatgcagggct tggcacgatacgtgttccagtcagagaacaccttctgcagtggggaccatgtgtcctggcacagccctttggataacagtgagtca agaattcagcacatgctgctgacagaggacccacagatgcagcccgtgcagacacccttggggtagttaccttcctccagatcgt tggtgtctgcactgaagagctacactcagcccagcagtggaacgggcagggcatcctggagctgctgcggacagtgcctattgctg gcggcccctggctgataactgacatgcggaggggagagaccatatttgagatcgatccacacctgcaagagagagttgacaaaggc atcgagacagatggctccaacctgagtggtgtcagtgccaagtgtgcctgggatgacctgagccggcccccgaggatgacgagga cagccggagcatctgcatcggcacacagccccggcgactctctggcaaagacacagagcagatccgggagaccctgaggagaggac tcgagatcaacagcaaacctgtccttccaccaatcaaccctcagcggcagaatggcctcgcccacgaccgggccccgagccgcaaa gacagcctggaaagtgacagctccacggccatcattcccatgagctgattcgcacgcggcagcttgagagcgtacatctgaaatt caaccaggagtccggagccctcattcctctctgcctaaggggcaggctcctgcatggacggcactttacatataaaagtatcacag gtgacatggccatcacgttttgtctccacgggagtggaaggcgccttttgccactgaggagcatccttacgcggctcatggaccctgg ttacaaattctgttgaccgaagagtttgtagagaaaatgttggaggatttagaagatttgacttctccagaggaattcaaacttcc caaagagtacagctggcctgaaaagaagctgaaggtctccatcctgcctgacgtggtgttcgacagtccgctacactag SuFu amino acid sequence - NP_057253.2

(SEQ ID NO: 28)

MAELRPSGAPGPTAPPAPGPTAPPAFASLFPPGLHAIYGECRRLYPDQPNPLQVTAIVKYWLGGPDPLDYVSMYRNVGSPSANIPE

HWHYISFGLSDLYGDNRVHEFTGTDGPSGFGFELTFRLKRETGESAPPTWPAELMQGLARYVFQSENTFCSGDHVSWHSPLDNSES

RIQHMLLTEDPQMQPVQTPFGVVTFLQIVGVCTEELHSAQQWNGQGILELLRTVPIAGGPWLITDMRRGETIFEIDPHLQERVDKG

IETDGSNLSGVSAKCAWDDLSRPPEDDEDSRSICIGTQPRRLSGKDTEQIRETLRRGLEINSKPVLPPINPQRQNGLAHDRAPSRK

DSLESDSSTAIIPHELIRTRQLESVHLKFNQESGALIPLCLRGRLLHGRHFTYKSITGDMAITFVSTGVEGAFATEEHPYAAHGPW

LQILLTEEFVEKMLEDLEDLTSPEEFKLPKEYSWPEKKLKVSILPDVVFDSPLH

The invention claimed is:

1. A method of modulating FSH signaling in a subject, comprising:
   administering to a subject in need of modulation of FSH signaling an effective amount of an Hh pathway modulator, thereby modulating FSH signaling.

2. The method of claim 1, further comprising identifying the subject as a subject in need of modulation of FSH signaling.

3. The method of claim 1, wherein the subject has a gynecologic disorder.

4. The method of claim 3, wherein the gynecologic disorder is endometriosis or leiomyomata.

5. The method of claim 1, wherein the Hh pathway modulator is an Hh pathway inhibitor.

6. The method of claim 5, wherein the Hh pathway inhibitor is an inhibitor of an Hh polypeptide, a Cdo polypeptide, a Boc polypeptide, a Gas1 polypeptide, a Smo polypeptide, or a Gli polypeptide.

7. The method of claim 5, wherein the Hh pathway inhibitor is an activator of a Ptc polypeptide, an Hhip polypeptide, or an SuFu polypeptide.

8. The method of claim 5, wherein the Hh pathway inhibitor is vismodegib.

9. A method of suppressing ovarian function in a subject, comprising:
   administering to a subject in need of ovarian suppression an effective amount of an Hh pathway inhibitor to reduce FSH signaling, thereby suppressing ovarian function in the subject.

10. The method of claim 9, wherein the subject has or is susceptible to a gynecologic condition.

11. The method of claim 10, wherein the gynecologic condition is endometriosis or leiomyomata.

12. The method of claim 9, wherein the Hh pathway inhibitor is an inhibitor of an Hh polypeptide, a Cdo polypeptide, a Boc polypeptide, a Gas1 polypeptide, a Smo polypeptide, or a Gli polypeptide.

13. The method of claim 9, wherein the Hh pathway inhibitor is an activator of a Ptc polypeptide, an Hhip polypeptide, or an SuFu polypeptide.

14. The method of claim 9, wherein the Hh pathway inhibitor is vismodegib.

15. A method of increasing fertility in a subject, comprising: administering to a subject in need of an increase in fertility an Hh pathway activator, to increase FSH signaling, thereby increasing fertility in the subject.

16. The method of claim 15, wherein the Hh pathway activator is an activator of an Hh polypeptide, a Cdo polypeptide, a Boc polypeptide, a Gas1 polypeptide, a Smo polypeptide, or a Gli polypeptide.

17. The method of claim 15, wherein the Hh pathway activator is an inhibitor of a Ptc polypeptide, an Hhip polypeptide, or an SuFu polypeptide.

18. The method of claim 9, wherein the effective amount of the Hh pathway inhibitor inhibits FSH signaling in the subject.

19. The method of claim 9, wherein the effective amount of the Hh pathway inhibitor increases level of FSH in the subject.

* * * * *

SEQUENCE LISTING

<160> NUMBER OF SEQ ID NOS: 28

<210> SEQ ID NO 1
<211> LENGTH: 4293
<212> TYPE: DNA
<213> ORGANISM: Homo sapiens

<400> SEQUENCE: 1

```
gtttctcata gttggcgtct tctaaaggaa aaacactaaa atgaggaact cagcggaccg      60
ggagcgacgc agcttgaggg aagcatccct agctgttggc gcagaggggc gaggctgaag     120
ccgagtggcc cgaggtgtct gagggctgg ggcaaaggtg aaagagtttc agaacaagct      180
tcctggaacc catgaccat gaagtcttgt cgacatttat accgtctgag ggtagcagct      240
cgaaagtaga agaagtggag tgttgccagg gacggcagta tctctttgtg tgaccctggc     300
ggcttatggg acgttggctt cagacctttg tgatacacca tgctgcgtgg gacgatgacg     360
gcgtggagag gaatgaggcc tgaggtcaca ctggcttgcc cctcctagc cacagcaggc      420 tgctttgctg acttgaacga ggtccctcag gtcaccgtcc agcctgcgtc accgtccag      480 aagcccggag gcactgtgat cttgggctgc gtggtggaac ctccaaggat gaatgtaacc     540
tggcgcctga atggaaagga gctgaatggc tcggatgatg ctctgggtgt cctcatcacc     600
cacgggaccc tcgtcatcac tgcccttaac aaccacactg tgggacggta ccagtgtgtg     660
gcccggatgc ctgcggggc tgtggccagc gtgccagcca ctgtgacact agccaatctc     720
caggacttca gttagatgt gcagcacgtg attgaagtgg atgagggaaa cacagcagtc     780
attgcctgcc acctgcctga gagccacccc aaagcccagg tccggtacag cgtcaaacaa     840
gagtggctgg aggcctccag aggtaactac ctgatcatgc cctcagggaa cctccagatt     900
gtgaatgcca gccaggagga cgagggcatg tacaagtgtg cagcctacaa cccagtgacc     960
caggaagtga aaacctccgg ctccagcgac aggctacgtg tgcgccgctc accgctgag    1020 gctgcccgca tcatctaccc cccagaggcc caaaccatca tcgtcaccaa aggccagagt    1080
ctcattctgg agtgtgtggc cagtggaatc ccaccccac gggtcacctg gccaaggat    1140 gggtccagtg tcaccggcta caacaagacg cgcttcctgc tgagcaacct cctcatcgac    1200
accaccagcg aggaggactc aggcacctac cgctgcatgg ccgacaatgg ggttgggcag    1260
cccggggcag cggtcatcct ctacaatgtc caggtgtttg aacccctga ggtcaccatg     1320 gagctatccc agctggtcat cccctggggc cagagtgcca gcttacctg tgaggtgcgt     1380 gggaaccccc cgccctccgt gctgtggctg aggaatgctg tgcccctcat ctccagccag    1440
cgcctccggc tctcccgcag ggccctgcgc gtgctcagca tggggcctga ggacgaaggc    1500
gtctaccagt gcatggccga aacgaggtt gggagcgccc atgccgtagt ccagctgcgg    1560
acctccaggc caagcataac cccaaggcta tggcaggatg ctgagctggc tactggcaca    1620
cctcctgtat caccctccaa actcggcaac cctgagcaga tgctgagggg gcaaccggcg    1680
ctccccagac ccccaacgtc agtggggcct gcttccccgc agtgtccagg agagaagggg    1740 caggggctc ccgccgaggc tcccatcatc ctcagctcgc cccgcacctc caagacagac     1800
tcatatgaac tggtgtggcg gcctcggcat gagggcagtg gccggcgcc aatcctctac    1860 tatgtggtga aacaccgcaa ggtcacaaat tcctctgacg attggaccat ctctggcatt    1920
ccagccaacc agcaccgcct gacctcacc agacttgacc ccgggagctt gtatgaagtg     1980
gagatggcag cttacaactg tgcgggagag ggccagacag ccatggtcac cttccgaact    2040
ggacggcggc ccaaacccga gatcatggcc agcaaagagc agcagatcca gagagacgac    2100
```

```
cctggagcca gtccccagag cagcagccag ccagaccacg gccgcctctc ccccccagaa    2160
gctcccgaca ggcccaccat ctccacggcc tccgagacct cagtgtacgt gacctggatt    2220
ccccgtggga atggtgggtt cccaatccag tccttccgtg tggagtacaa gaagctaaag    2280
aaagtgggag actggattct ggccaccagc gccatccccc catcgcggct gtccgtggag    2340
atcacgggcc tagagaaagg cacctcctac aagtttcgag tccgggctct gaacatgctg    2400
ggggagagcg agcccagcgc ccctctcgg cctacgtgg tgtcgggcta cagcggtcgc       2460
gtgtacgaga ggcccgtggc aggtccttat atcaccttca cggatgcggt caatgagacc    2520
accatcatgc tcaagtggat gtacatccca gcaagtaaca caacacccc aatccatggc      2580 ttttatatct attatcgacc cacagacagt gacaatgata gtgactacaa gaggatatg      2640 gtggaagggg acaagtactg gcactccatc agccacctgc agccagagac ctcctacgac    2700
attaagatgc agtgcttcaa tgaaggaggg gagagcgagt tcagcaacgt gatgatctgt    2760
gagaccaaag ctcggaagtc ttctggccag cctggtcgac tgccaccccc aactctggcc    2820
ccaccacagc cgccccttcc tgaaaccata gagcggccgg tgggcactgg ggccatggtg    2880
gctcgctcca cgacctgcc ctatctgatt gtcggggtcg tcctgggctc catcgttctc      2940
atcatcgtca ccttcatccc cttctgcttg tggagggcct ggtctaagca aaacataca     3000 acagacctgg ttttcctcg aagtgccctt ccaccctcct gcccgtatac tatggtgcca     3060
ttgggaggac tcccaggcca ccaggccagt ggacagccct acctcagtgg catcagtgga   3120
cgggcctgtg ctaatgggat ccacatgaat aggggctgcc cctcggctgc agtgggctac    3180
ccgggcatga agccccagca gcactgccca ggcgagcttc agcagcagag tgacaccagc    3240
agcctgctga ggcagaccca tcttggcaat ggatatgacc cccaaagtca ccagatcacg    3300
aggggtccca gtctagcccc ggacgagggc tctttcttat acacactgcc cgacgactcc    3360
actcaccagc tgctgcagcc ccatcacgac tgctgccaac gccaggagca gcctgctgct   3420
gtgggccagt cagggtgag gagagccccc gacagtcctg tcctggaagc agtgtgggac    3480
cctccatttc actcagggcc ccatgctgc ttgggccttg tgccagttga agaggtggac      3540
agtcctgact cctgccaagt gagtggagga gactggtgtc cccagcaccc cgtaggggcc    3600
tacgtaggac aggaacctgg aatgcagctc tccccggggc cactggtgcg tgtgtctttt    3660
gaaacaccac ctctcacaat ttaggcagaa gctgatatcc cagaaagact atatattgtt    3720 tttttttaa aaaaaaaag aagaaaaaag agacagagaa aattggtatt tatttttcta      3780
ttatagccat atttatatat ttatgcactt gtaaataaat gtatatgttt tataattctg     3840
gagagacata aggagtccta cccgttgagg ttggagaggg aaaataaaga agctgccacc    3900
taacaggagt cacccaggaa agcaccgcac aggctggcgc gggacagact cctaacctgg    3960
ggcctctgca gtggcaggcg aggctgcagg aggcccacag ataagctggc aagaggaagg    4020
atcccaggca catggttcat cacgagcatg agggaacagc aaggggcacg gtatcacagc    4080
ctggagacac ccacacagat ggctggatcc ggtgctacgg gaaacatttt cctaagatgc    4140
ccatgagaac agaccaagat gtgtacagca ctatgagcat taaaaaacct tccagaatca    4200
ataatccgtg gcaacatatc tctgtaaaaa caaaacactgt aacttctaaa taatgtttta    4260
gtcttccctg taaccttcaa aaaaaaaaaa aaa                                 4293
```

<210> SEQ ID NO 2
<211> LENGTH: 1114
<212> TYPE: PRT

<213> ORGANISM: Homo sapiens

<400> SEQUENCE: 2

```
Met Leu Arg Gly Thr Met Thr Ala Trp Arg Gly Met Pro Glu Val
1               5                   10                  15

Thr Leu Ala Cys Leu Leu Leu Ala Thr Ala Gly Cys Phe Ala Asp Leu
                20                  25                  30

Asn Glu Val Pro Gln Val Thr Val Gln Pro Ala Ser Thr Val Gln Lys
            35                  40                  45

Pro Gly Gly Thr Val Ile Leu Gly Cys Val Val Glu Pro Pro Arg Met
    50                  55                  60

Asn Val Thr Trp Arg Leu Asn Gly Lys Glu Leu Asn Gly Ser Asp Asp
65                  70                  75                  80

Ala Leu Gly Val Leu Ile Thr His Gly Thr Leu Val Ile Thr Ala Leu
                85                  90                  95

Asn Asn His Thr Val Gly Arg Tyr Gln Cys Val Ala Arg Met Pro Ala
            100                 105                 110

Gly Ala Val Ala Ser Val Pro Ala Thr Val Thr Leu Ala Asn Leu Gln
            115                 120                 125

Asp Phe Lys Leu Asp Val Gln His Val Ile Glu Val Asp Glu Gly Asn
130                 135                 140

Thr Ala Val Ile Ala Cys His Leu Pro Glu Ser His Pro Lys Ala Gln
145                 150                 155                 160

Val Arg Tyr Ser Val Lys Gln Glu Trp Leu Glu Ala Ser Arg Gly Asn
                165                 170                 175

Tyr Leu Ile Met Pro Ser Gly Asn Leu Gln Ile Val Asn Ala Ser Gln
            180                 185                 190

Glu Asp Glu Gly Met Tyr Lys Cys Ala Ala Tyr Asn Pro Val Thr Gln
            195                 200                 205

Glu Val Lys Thr Ser Gly Ser Ser Asp Arg Leu Arg Val Arg Arg Ser
            210                 215                 220

Thr Ala Glu Ala Ala Arg Ile Ile Tyr Pro Pro Glu Ala Gln Thr Ile
225                 230                 235                 240

Ile Val Thr Lys Gly Gln Ser Leu Ile Leu Glu Cys Val Ala Ser Gly
                245                 250                 255

Ile Pro Pro Pro Arg Val Thr Trp Ala Lys Asp Gly Ser Ser Val Thr
            260                 265                 270

Gly Tyr Asn Lys Thr Arg Phe Leu Leu Ser Asn Leu Leu Ile Asp Thr
            275                 280                 285

Thr Ser Glu Glu Asp Ser Gly Thr Tyr Arg Cys Met Ala Asp Asn Gly
            290                 295                 300

Val Gly Gln Pro Gly Ala Ala Val Ile Leu Tyr Asn Val Gln Val Phe
305                 310                 315                 320

Glu Pro Pro Glu Val Thr Met Glu Leu Ser Gln Leu Val Ile Pro Trp
                325                 330                 335

Gly Gln Ser Ala Lys Leu Thr Cys Glu Val Arg Gly Asn Pro Pro Pro
            340                 345                 350

Ser Val Leu Trp Leu Arg Asn Ala Val Pro Leu Ile Ser Ser Gln Arg
            355                 360                 365

Leu Arg Leu Ser Arg Arg Ala Leu Arg Val Leu Ser Met Gly Pro Glu
            370                 375                 380

Asp Glu Gly Val Tyr Gln Cys Met Ala Glu Asn Glu Val Gly Ser Ala
385                 390                 395                 400
```

```
His Ala Val Val Gln Leu Arg Thr Ser Arg Pro Ser Ile Thr Pro Arg
                405                 410                 415
Leu Trp Gln Asp Ala Glu Leu Ala Thr Gly Thr Pro Pro Val Ser Pro
            420                 425                 430
Ser Lys Leu Gly Asn Pro Glu Gln Met Leu Arg Gly Gln Pro Ala Leu
        435                 440                 445
Pro Arg Pro Pro Thr Ser Val Gly Pro Ala Ser Pro Gln Cys Pro Gly
    450                 455                 460
Glu Lys Gly Gln Gly Ala Pro Ala Glu Ala Pro Ile Ile Leu Ser Ser
465                 470                 475                 480
Pro Arg Thr Ser Lys Thr Asp Ser Tyr Glu Leu Val Trp Arg Pro Arg
                485                 490                 495
His Glu Gly Ser Gly Arg Ala Pro Ile Leu Tyr Tyr Val Val Lys His
            500                 505                 510
Arg Lys Val Thr Asn Ser Ser Asp Trp Thr Ile Ser Gly Ile Pro
        515                 520                 525
Ala Asn Gln His Arg Leu Thr Leu Thr Arg Leu Asp Pro Gly Ser Leu
    530                 535                 540
Tyr Glu Val Glu Met Ala Ala Tyr Asn Cys Ala Gly Glu Gly Gln Thr
545                 550                 555                 560
Ala Met Val Thr Phe Arg Thr Gly Arg Arg Pro Lys Pro Glu Ile Met
                565                 570                 575
Ala Ser Lys Glu Gln Gln Ile Gln Arg Asp Asp Pro Gly Ala Ser Pro
            580                 585                 590
Gln Ser Ser Ser Gln Pro Asp His Gly Arg Leu Ser Pro Pro Glu Ala
        595                 600                 605
Pro Asp Arg Pro Thr Ile Ser Thr Ala Ser Glu Thr Ser Val Tyr Val
    610                 615                 620
Thr Trp Ile Pro Arg Gly Asn Gly Gly Phe Pro Ile Gln Ser Phe Arg
625                 630                 635                 640
Val Glu Tyr Lys Lys Leu Lys Lys Val Gly Asp Trp Ile Leu Ala Thr
                645                 650                 655
Ser Ala Ile Pro Pro Ser Arg Leu Ser Val Glu Ile Thr Gly Leu Glu
            660                 665                 670
Lys Gly Thr Ser Tyr Lys Phe Arg Val Arg Ala Leu Asn Met Leu Gly
        675                 680                 685
Glu Ser Glu Pro Ser Ala Pro Ser Arg Pro Tyr Val Val Ser Gly Tyr
    690                 695                 700
Ser Gly Arg Val Tyr Glu Arg Pro Val Ala Gly Pro Tyr Ile Thr Phe
705                 710                 715                 720
Thr Asp Ala Val Asn Glu Thr Thr Ile Met Leu Lys Trp Met Tyr Ile
                725                 730                 735
Pro Ala Ser Asn Asn Asn Thr Pro Ile His Gly Phe Tyr Ile Tyr Tyr
            740                 745                 750
Arg Pro Thr Asp Ser Asp Asn Asp Ser Asp Tyr Lys Lys Asp Met Val
        755                 760                 765
Glu Gly Asp Lys Tyr Trp His Ser Ile Ser His Leu Gln Pro Glu Thr
    770                 775                 780
Ser Tyr Asp Ile Lys Met Gln Cys Phe Asn Glu Gly Gly Glu Ser Glu
785                 790                 795                 800
Phe Ser Asn Val Met Ile Cys Glu Thr Lys Ala Arg Lys Ser Ser Gly
                805                 810                 815
Gln Pro Gly Arg Leu Pro Pro Pro Thr Leu Ala Pro Pro Gln Pro Pro
```

-continued

```
                820                 825                 830
Leu Pro Glu Thr Ile Glu Arg Pro Val Gly Thr Gly Ala Met Val Ala
        835                 840                 845

Arg Ser Ser Asp Leu Pro Tyr Leu Ile Val Gly Val Leu Gly Ser
    850                 855                 860

Ile Val Leu Ile Ile Val Thr Phe Ile Pro Phe Cys Leu Trp Arg Ala
865                 870                 875                 880

Trp Ser Lys Gln Lys His Thr Thr Asp Leu Gly Phe Pro Arg Ser Ala
                885                 890                 895

Leu Pro Pro Ser Cys Pro Tyr Thr Met Val Pro Leu Gly Gly Leu Pro
            900                 905                 910

Gly His Gln Ala Ser Gly Gln Pro Tyr Leu Ser Gly Ile Ser Gly Arg
        915                 920                 925

Ala Cys Ala Asn Gly Ile His Met Asn Arg Gly Cys Pro Ser Ala Ala
        930                 935                 940

Val Gly Tyr Pro Gly Met Lys Pro Gln Gln His Cys Pro Gly Glu Leu
945                 950                 955                 960

Gln Gln Gln Ser Asp Thr Ser Ser Leu Leu Arg Gln Thr His Leu Gly
                965                 970                 975

Asn Gly Tyr Asp Pro Gln Ser His Gln Ile Thr Arg Gly Pro Lys Ser
            980                 985                 990

Ser Pro Asp Glu Gly Ser Phe Leu Tyr Thr Leu Pro Asp Asp Ser Thr
        995                 1000                1005

His Gln Leu Leu Gln Pro His Asp Cys Cys Gln Arg Gln Glu
    1010                1015                1020

Gln Pro Ala Ala Val Gly Gln Ser Gly Val Arg Arg Ala Pro Asp
    1025                1030                1035

Ser Pro Val Leu Glu Ala Val Trp Asp Pro Pro Phe His Ser Gly
    1040                1045                1050

Pro Pro Cys Cys Leu Gly Leu Val Pro Val Glu Glu Val Asp Ser
    1055                1060                1065

Pro Asp Ser Cys Gln Val Ser Gly Gly Asp Trp Cys Pro Gln His
    1070                1075                1080

Pro Val Gly Ala Tyr Val Gly Gln Glu Pro Gly Met Gln Leu Ser
    1085                1090                1095

Pro Gly Pro Leu Val Arg Val Ser Phe Glu Thr Pro Pro Leu Thr
    1100                1105                1110

Ile
```

<210> SEQ ID NO 3
<211> LENGTH: 4277
<212> TYPE: DNA
<213> ORGANISM: Homo sapiens

<400> SEQUENCE: 3

```
gtttctcata gttggcgtct tctaaaggaa aaacactaaa atgaggaact cagcggaccg      60
ggagcgacgc agcttgaggg aagcatccct agctgttggc gcagaggggc gaggctgaag    120
ccgagtggcc cgaggtgtct gaggggctgg ggcaaaggtg aaagagtttc agaacaagct    180
tcctggaacc catgacccat gaagtcttgt cgacatttat accgtctgag ggtagcagct    240
cgaaactaga agaagtggag tgttgccagg acggcagta tctctttgtg tgaccctggc     300
ggcctatggg acgttggctt cagacctttg tgatacacca tgctgcgtgg acgatgacg     360 gcgtggagag gaatgaggcc tgaggtcaca ctggcttgcc tcctcctagc cacagcaggc    420
```

```
tgctttgctg acttgaacga ggtccctcag gtcaccgtcc agcctgcgtc caccgtccag    480
aagcccggag gcactgtgat cttgggctgc gtggtggaac ctccaaggat gaatgtaacc    540
tggcgcctga atggaaagga gctgaatggc tcggatgatg ctctgggtgt cctcatcacc    600
cacgggaccc tcgtcatcac tgcccttaac aaccacactg tgggacggta ccagtgtgtg    660
gcccggatgc ctgcggggc tgtggccagc gtgccagcca ctgtgacact agccaatctc    720
caggacttca gttagatgt gcagcacgtg attgaagtgg atgagggaaa cacagcagtc    780
attgcctgcc acctgcctga gccacccc aaagcccagg tccggtacag cgtcaaacaa    840
gagtggctga aggcctccag aggtaactac ctgatcatgc cctcagggaa cctccagatt    900
gtgaatgcca gccaggagga cgagggcatg tacaagtgtg cagcctacaa cccagtgacc    960
caggaagtga aaacctccgg ctccagcgac aggctacgtg tgcgccgctc caccgctgag   1020
gctgcccgca tcatctaccc cccagaggcc caaaccatca tcgtcaccaa aggccagagt   1080
ctcattctgg agtgtgtggc cagtggaatc ccaccccac gggtcacctg gccaaggat    1140 gggtccagtg tcaccggcta acaagacg cgcttcctgc tgagcaacct cctcatcgac    1200
accaccagcg aggaggactc aggcacctac cgctgcatgg ccgacaatgg ggttgggcag   1260
cccggggcag cggtcatcct ctacaatgtc caggtgtttg aaccccctga ggtcaccatg   1320
gagctatccc agctggtcat cccctggggc cagagtgcca agcttacctg tgaggtgcgt   1380
gggaaccccc cgccctccgt gctgtggctg aggaatgctg tgcccctcat ctccagccag   1440
cgcctccggc tctcccgcag ggccctgcgc gtgctcagca tggggcctga ggacgaaggc   1500
gtctaccagt gcatggccga gaacgaggtt gggagcgccc atgccgtagt ccagctgcgg   1560
acctccaggc caagcataac cccaaggcta tggcaggatg ctgagctggc tactggcaca   1620
cctcctgtat caccctccaa actcggcaac cctgagcaga tgctgagggg caaccggcg   1680 ctccccagac cccaacgtc agtggggcct gcttccccga gtgtccagg agagaagggg   1740 caggggctc ccgccgaggc tcccatcatc ctcagctcgc cccgcacctc caagacagac   1800
tcatatgaac tggtgtggcg gcctcggcat gagggcagtg gccgggcgcc aatcctctac   1860
tatgtggtga acaccgcaa gcaggtcaca aattcctctg acgattggac catctctggc   1920
attccagcca accagcaccg cctgaccctc accagacttg accccgggag cttgtatgaa   1980
gtggagatgg cagcttacaa ctgtgcggga gagggccaga cagccatggt caccttccga   2040
actggacggc ggcccaaacc cgagatcatg ccagcaaag agcagcagat ccagagagac   2100
gaccctggag ccagtcccca gagcagcagc cagccagacc acggccgcct ctcccccca   2160 gaagctcccg acaggcccac catctccacg gcctccgaga cctcagtgta cgtgacctgg   2220 attcccgtg ggaatggtgg gttcccaatc cagtccttcc gtgtgagta caagaagcta   2280 aagaaagtgg gagactggat tctggccacc agcgccatcc cccatcgcg gctgtccgtg   2340 gagatcacgg gcctagagaa aggcaccct tacaagttc gagtccgggc tctgaacatg   2400
ctgggggaga gcgagcccag cgccccctct cggccctacg tggtgtcggg ctacagcggt   2460
cgcgtgtacg agaggcccgt ggcaggtcct tatatcacct tcacggatgc ggtcaatgag   2520
accaccatca tgctcaagtg gatgtacatc ccagcaagta caacaacac cccaatccat   2580 ggcttttata tctattatcg acccacagac agtgacaatg atagtgacta caagaaggat   2640
atggtggaag gggacaagta ctggcactcc atcagccacc tgcagccaga gacctcctac   2700
gacattaaga tgcagtgctt caatgaagga ggggagagcg agttcagcaa cgtgatgatc   2760
```

-continued

```
tgtgagacca aagctcggaa gtcttctggc cagcctggtc gactgccacc cccaactctg    2820
gccccaccac agccgcccct tcctgaaacc atagagcggc cggtgggcac tggggccatg    2880
gtggctcgct ccagcgacct gccctatctg attgtcgggg tcgtcctggg ctccatcgtt    2940
ctcatcatcg tcaccttcat cccettctgc ttgtggaggg cctggtctaa gcaaaaacat    3000
acaacagacc tgggttttcc tcgaagtgcc cttccaccct cctgcccgta tactatggtg    3060
ccattgggag gactcccagg ccaccaggcc agtggacagc cctacctcag tggcatcagt    3120
ggacgggcct gtgctaatgg gatccacatg aatagggggct gcccctcggc tgcagtgggc    3180
tacccgggca tgaagcccca gcagcactgc ccaggcgagc ttcagcagca gagtgacacc    3240
agcagcctgc tgaggcagac ccatcttggc aatggatatg accccaaag tcaccagatc    3300 acgaggggtc ccaagtctag cccggacgag ggctctttct tatacacact gcccgacgac    3360
tccactcacc agctgctgca gccccatcac gactgctgcc aacgccagga gcagcctgct    3420
gctgtgggcc agtcaggggt gaggagagcc cccgacagtc ctgtcctgga agcagtgtgg    3480
gaccctccat ttcactcagg gccccatgc tgcttgggcc ttgtgccagt tgaagaggtg    3540
gacagtcctg actcctgcca agtgagtgga ggagactggt gtcccagca cccgtaggg    3600 gcctacgtag acaggaacc tggaatgcag ctctccccgg ggccactggt gcgtgtgtct    3660
tttgaaacac cacctctcac aatttaggca gaagctgata tcccagaaag actatatatt    3720 gtttttttt taaaaaaaaa agaagaaaaa agagacagag aaaattggta tttatttttc    3780
tattatagcc atatttatat atttatgcac ttgtaaataa atgtatatgt tttataattc    3840
tggagagaca taaggagtcc tacccgttga ggttggagag ggaaaataaa gaagctgcca    3900
cctaacagga gtcacccagg aaagcaccgc acaggctggc gcgggacaga ctcctaacct    3960
ggggcctctg cagtggcagg cgaggctgca ggaggcccac agataagctg gcaagaggaa    4020
ggatcccagg cacatggttc atcacgagca tgagggaaca gcaaggggca cggtatcaca    4080
gcctggagac acccccacag atggctggat ccggtgctac gggaaacatt ttcctaagat    4140
gcccatgaga acagaccaag atgtgtacag cactatgagc attaaaaaac cttccagaat    4200
caataatccg tggcaacata tctctgtaaa aacaaacact gtaacttcta aataaatgtt    4260
tagtcttccc tgtaaaa                                                 4277
```

<210> SEQ ID NO 4
<211> LENGTH: 1287
<212> TYPE: PRT
<213> ORGANISM: Homo sapiens

<400> SEQUENCE: 4

```
Met His Pro Asp Leu Gly Pro Leu Cys Thr Leu Leu Tyr Val Thr Leu
1               5                   10                  15

Thr Ile Leu Cys Ser Ser Val Ser Ser Asp Leu Ala Pro Tyr Phe Thr
            20                  25                  30

Ser Glu Pro Leu Ser Ala Val Gln Lys Leu Gly Gly Pro Val Val Leu
        35                  40                  45

His Cys Ser Ala Gln Pro Val Thr Thr Arg Ile Ser Trp Leu His Asn
    50                  55                  60

Gly Lys Thr Leu Asp Gly Asn Leu Glu His Val Lys Ile His Gln Gly
65                  70                  75                  80

Thr Leu Thr Ile Leu Ser Leu Asn Ser Ser Leu Leu Gly Tyr Tyr Gln
                85                  90                  95

Cys Leu Ala Asn Asn Ser Ile Gly Ala Ile Val Ser Gly Pro Ala Thr
```

```
                100             105             110
Val Ser Val Ala Val Leu Gly Asp Phe Gly Ser Ser Thr Lys His Val
        115             120             125
Ile Thr Ala Glu Glu Lys Ser Ala Gly Phe Ile Gly Cys Arg Val Pro
        130             135             140
Glu Ser Asn Pro Lys Ala Glu Val Arg Tyr Lys Ile Arg Gly Lys Trp
145             150             155             160
Leu Glu His Ser Thr Glu Asn Tyr Leu Ile Leu Pro Ser Gly Asn Leu
                165             170             175
Gln Ile Leu Asn Val Ser Leu Glu Asp Lys Gly Ser Tyr Lys Cys Ala
        180             185             190
Ala Tyr Asn Pro Val Thr His Gln Leu Lys Val Glu Pro Ile Gly Arg
        195             200             205
Lys Leu Leu Val Ser Arg Pro Ser Ser Asp Val His Ile Leu His
        210             215             220
Pro Thr His Ser Gln Ala Leu Ala Val Leu Ser Arg Ser Pro Val Thr
225             230             235             240
Leu Glu Cys Val Val Ser Gly Val Pro Ala Pro Gln Val Tyr Trp Leu
                245             250             255
Lys Asp Gly Gln Asp Ile Ala Pro Gly Ser Asn Trp Arg Arg Leu Tyr
        260             265             270
Ser His Leu Ala Thr Asp Ser Val Asp Pro Ala Asp Ser Gly Asn Tyr
        275             280             285
Ser Cys Met Ala Gly Asn Lys Ser Gly Asp Val Lys Tyr Val Thr Tyr
        290             295             300
Met Val Asn Val Leu Glu His Ala Ser Ile Ser Lys Gly Leu Gln Asp
305             310             315             320
Gln Ile Val Ser Leu Gly Ala Thr Val His Phe Thr Cys Asp Val His
                325             330             335
Gly Asn Pro Ala Pro Asn Cys Thr Trp Phe His Asn Ala Gln Pro Ile
        340             345             350
His Pro Ser Ala Arg His Leu Thr Ala Gly Asn Gly Leu Lys Ile Ser
        355             360             365
Gly Val Thr Val Glu Asp Val Gly Met Tyr Gln Cys Val Ala Asp Asn
        370             375             380
Gly Ile Gly Phe Met His Ser Thr Gly Arg Leu Glu Ile Glu Asn Asp
385             390             395             400
Gly Gly Phe Lys Pro Val Ile Thr Ala Pro Val Ser Ala Lys Val
                405             410             415
Ala Asp Gly Asp Phe Val Thr Leu Ser Cys Asn Ala Ser Gly Leu Pro
        420             425             430
Val Pro Val Ile Arg Trp Tyr Asp Ser His Gly Leu Ile Thr Ser His
        435             440             445
Pro Ser Gln Val Leu Arg Ser Lys Ser Arg Lys Ser Gln Leu Ser Arg
        450             455             460
Pro Glu Gly Leu Asn Leu Glu Pro Val Tyr Phe Val Leu Ser Gln Ala
465             470             475             480
Gly Ala Ser Ser Leu His Ile Gln Ala Val Thr Gln Glu His Ala Gly
                485             490             495
Lys Tyr Ile Cys Glu Ala Ala Asn Glu His Gly Thr Thr Gln Ala Glu
        500             505             510
Ala Ser Leu Met Val Val Pro Phe Glu Thr Asn Thr Lys Ala Glu Thr
        515             520             525
```

-continued

Val Thr Leu Pro Asp Ala Ala Gln Asn Asp Asp Arg Ser Lys Arg Asp
    530                 535                 540

Gly Ser Glu Thr Gly Leu Leu Ser Ser Phe Pro Val Lys Val His Pro
545                 550                 555                 560

Ser Ala Val Glu Ser Ala Pro Glu Lys Asn Ala Ser Gly Ile Ser Val
                565                 570                 575

Pro Asp Ala Pro Ile Ile Leu Ser Pro Pro Gln Thr His Thr Pro Asp
            580                 585                 590

Thr Tyr Asn Leu Val Trp Arg Ala Gly Lys Asp Gly Gly Leu Pro Ile
        595                 600                 605

Asn Ala Tyr Phe Val Lys Tyr Arg Lys Leu Asp Asp Gly Val Gly Met
    610                 615                 620

Leu Gly Ser Trp His Thr Val Arg Val Pro Gly Ser Glu Asn Glu Leu
625                 630                 635                 640

His Leu Ala Glu Leu Glu Pro Ser Ser Leu Tyr Glu Val Leu Met Val
                645                 650                 655

Ala Arg Ser Ala Ala Gly Glu Gly Gln Pro Ala Met Leu Thr Phe Arg
            660                 665                 670

Thr Ser Lys Glu Lys Thr Ala Ser Ser Lys Asn Thr Gln Ala Ser Ser
        675                 680                 685

Pro Pro Val Gly Ile Pro Lys Tyr Pro Val Val Ser Glu Ala Ala Asn
    690                 695                 700

Asn Asn Phe Gly Val Val Leu Thr Asp Ser Ser Arg His Ser Gly Val
705                 710                 715                 720

Pro Glu Ala Pro Asp Arg Pro Thr Ile Ser Thr Ala Ser Glu Thr Ser
                725                 730                 735

Val Tyr Val Thr Trp Ile Pro Arg Ala Asn Gly Gly Ser Pro Ile Thr
            740                 745                 750

Ala Phe Lys Val Glu Tyr Lys Arg Met Arg Thr Ser Asn Trp Leu Val
        755                 760                 765

Ala Ala Glu Asp Ile Pro Pro Ser Lys Leu Ser Val Glu Val Arg Ser
    770                 775                 780

Leu Glu Pro Gly Ser Thr Tyr Lys Phe Arg Val Ile Ala Ile Asn His
785                 790                 795                 800

Tyr Gly Glu Ser Phe Arg Ser Ser Ala Ser Arg Pro Tyr Gln Val Val
                805                 810                 815

Gly Phe Pro Asn Arg Phe Ser Ser Arg Pro Ile Thr Gly Pro His Ile
            820                 825                 830

Ala Tyr Thr Glu Ala Val Ser Asp Thr Gln Ile Met Leu Lys Trp Thr
        835                 840                 845

Tyr Ile Pro Ser Ser Asn Asn Asn Thr Pro Ile Gln Gly Phe Tyr Ile
    850                 855                 860

Tyr Tyr Arg Pro Thr Asp Ser Asp Asn Asp Ser Asp Tyr Lys Arg Asp
865                 870                 875                 880

Val Val Glu Gly Ser Lys Gln Trp His Met Ile Gly His Leu Gln Pro
                885                 890                 895

Glu Thr Ser Tyr Asp Ile Lys Met Gln Cys Phe Asn Glu Gly Gly Glu
            900                 905                 910

Ser Glu Phe Ser Asn Val Met Ile Cys Glu Thr Lys Val Lys Arg Val
        915                 920                 925

Pro Gly Ala Ser Glu Tyr Pro Val Lys Asp Leu Ser Thr Pro Pro Asn
    930                 935                 940

-continued

```
Ser Leu Gly Ser Gly Gly Asn Val Gly Pro Ala Thr Ser Pro Ala Arg
945                 950                 955                 960

Ser Ser Asp Met Leu Tyr Leu Ile Val Gly Cys Val Leu Gly Val Met
            965                 970                 975

Val Leu Ile Leu Met Val Phe Ile Ala Met Cys Leu Trp Lys Asn Arg
        980                 985                 990

Gln Gln Asn Thr Ile Gln Lys Tyr Asp Pro Pro Gly Tyr Leu Tyr Gln
    995                 1000                1005

Gly Ser Asp Met Asn Gly Gln Met Val Asp Tyr Thr Thr Leu Ser
    1010                1015                1020

Gly Ala Ser Gln Ile Asn Gly Asn Val His Gly Gly Phe Leu Thr
    1025                1030                1035

Asn Gly Gly Leu Ser Ser Gly Tyr Ser His Leu His His Lys Val
    1040                1045                1050

Pro Asn Ala Val Asn Gly Ile Val Asn Gly Ser Leu Asn Gly Gly
    1055                1060                1065

Leu Tyr Ser Gly His Ser Asn Ser Leu Thr Arg Thr His Val Asp
    1070                1075                1080

Phe Glu His Pro His His Leu Val Asn Gly Gly Met Tyr Thr
    1085                1090                1095

Ala Val Pro Gln Ile Asp Pro Leu Glu Cys Val Asn Cys Arg Asn
    1100                1105                1110

Cys Arg Asn Asn Asn Arg Cys Phe Thr Lys Thr Asn Ser Thr Phe
    1115                1120                1125

Ser Ser Ser Pro Pro Pro Val Val Pro Val Val Ala Pro Tyr Pro
    1130                1135                1140

Gln Asp Gly Leu Glu Met Lys Pro Leu Ser His Val Lys Val Pro
    1145                1150                1155

Val Cys Leu Thr Ser Ala Val Pro Asp Cys Gly Gln Leu Pro Glu
    1160                1165                1170

Glu Ser Val Lys Asp Asn Val Glu Pro Val Pro Thr Gln Arg Thr
    1175                1180                1185

Cys Cys Gln Asp Ile Val Asn Asp Val Ser Ser Asp Gly Ser Glu
    1190                1195                1200

Asp Pro Ala Glu Phe Ser Arg Gly Gln Glu Gly Met Ile Asn Leu
    1205                1210                1215

Arg Ile Pro Asp His Leu Gln Leu Ala Lys Ser Cys Val Trp Glu
    1220                1225                1230

Gly Asp Ser Cys Ala His Ser Glu Thr Glu Ile Asn Ile Val Ser
    1235                1240                1245

Trp Asn Ala Leu Ile Leu Pro Pro Val Pro Glu Gly Cys Ala Glu
    1250                1255                1260

Lys Thr Met Trp Ser Pro Pro Gly Ile Pro Leu Asp Ser Pro Thr
    1265                1270                1275

Glu Val Leu Gln Gln Pro Arg Glu Thr
    1280                1285
```

<210> SEQ ID NO 5
<211> LENGTH: 1327
<212> TYPE: DNA
<213> ORGANISM: Homo sapiens

<400> SEQUENCE: 5

```
caaactttc caccggctcc gcgtccgccg ctccccgcgc ctcgtctcct ttccctcct        60
```

```
ctcccggcgg ccgccgctgc ccgcgatggt ggccgcgctg ctgggcggcg cggcgaggc      120
ccgcgggggg acagtgccgg gcgcctggct gtgcctgatg cgctgctgc agctgctggg      180
ctcggcgccg cggggatcgg ggctggcgca cggccgccgc ctcatctgct ggcaggcgct      240
gctgcagtgc caggggggagc cggagtgcag ctacgcctac aaccaatacg ccgaggcgtg      300
cgcgccggtg ctggcgcagc acggcggggg cgacgcgccc ggggccgccg ccgccgcttt      360
cccggcctcg gccgcctctt tctcgtcgcg ctggcgctgc ccgagtcact gcatctcggc      420
cctcattcag ctcaaccaca cgcgccgcgg gcccgccctg gaggactgtg actgcgcgca      480
ggacgagaac tgcaagtcca ccaagcgcgc cattgagccg tgcctgcccc ggacgagcgg      540
cggcggcgcg ggcggccccg gcgcggggcgg ggtcatgggc tgcaccgagg cccggcggcg      600
ctgcgaccgc gacagccgct gcaacctggc gctgagccgc tacctgacct actgcggcaa      660
agtcttcaac gggctgcgct gcacggacga atgccgcacc gtcattgagg acatgctggc      720
tatgcccaag gcggcgctgc tcaacgactg cgtgtgcgac ggcctcgagc ggcccatctg      780
cgagtcggtc aaggagaaca tggcccgcct gtgcttcggc gccgagctgg caacggccc      840
cggcagcagc ggctcggacg ggggcctgga cgactactac gatgaggact acgatgacga      900
gcagcgcacc gggggcgcgg gtggtgagca gccgctggac gacgacgacg gcgtcccgca      960
cccaccgcgc ccgggcagcg cgctgctgc atcgggcggc cgcggggacc tgccctatgg      1020
gcctgggcgc aggagcagcg gcggcggcgg ccgcttggcg ccccggggcg cctggacccc      1080
actcgcctcc atcttgctgc tgctgcttgg gccgctcttt tagccctcgc gccccccgcc      1140
gttggctgcg ggagagcccg cgtcccactc ccgtgctcgc ctcgaccccg cgccgggcac      1200
ctgtggcttg ggacagatag aagggatggt tggggatact tcccaaaact ttttccaagt      1260
caacttggtg tagccggttc cccggccacg actctgggca cttcccctga agctcctctc      1320
cggagct                                                               1327
```

<210> SEQ ID NO 6
<211> LENGTH: 345
<212> TYPE: PRT
<213> ORGANISM: Homo sapiens

<400> SEQUENCE: 6

```
Met Val Ala Ala Leu Gly Gly Gly Glu Ala Arg Gly Gly Thr
1               5                   10                  15

Val Pro Gly Ala Trp Leu Cys Leu Met Ala Leu Leu Gln Leu Leu Gly
            20                  25                  30

Ser Ala Pro Arg Gly Ser Gly Leu Ala His Gly Arg Arg Leu Ile Cys
        35                  40                  45

Trp Gln Ala Leu Leu Gln Cys Gln Gly Glu Pro Glu Cys Ser Tyr Ala
    50                  55                  60

Tyr Asn Gln Tyr Ala Glu Ala Cys Ala Pro Val Leu Ala Gln His Gly
65                  70                  75                  80

Gly Gly Asp Ala Pro Gly Ala Ala Ala Ala Phe Pro Ala Ser Ala
                85                  90                  95

Ala Ser Phe Ser Ser Arg Trp Arg Cys Pro Ser His Cys Ile Ser Ala
            100                 105                 110

Leu Ile Gln Leu Asn His Thr Arg Arg Gly Pro Ala Leu Glu Asp Cys
        115                 120                 125

Asp Cys Ala Gln Asp Glu Asn Cys Lys Ser Thr Lys Arg Ala Ile Glu
    130                 135                 140
```

| | | | | | | | | | | | | | | |
|---|---|---|---|---|---|---|---|---|---|---|---|---|---|---|
| Pro | Cys | Leu | Pro | Arg | Thr | Ser | Gly | Gly | Ala | Gly | Gly | Pro | Gly | Ala |
| 145 | | | | 150 | | | | | 155 | | | | | 160 |
| Gly | Gly | Val | Met | Gly | Cys | Thr | Glu | Ala | Arg | Arg | Cys | Asp | Arg | Asp |
| | | | | 165 | | | | | 170 | | | | | 175 |
| Ser | Arg | Cys | Asn | Leu | Ala | Leu | Ser | Arg | Tyr | Leu | Thr | Tyr | Cys | Gly | Lys |
| | | | 180 | | | | | 185 | | | | | 190 | | |
| Val | Phe | Asn | Gly | Leu | Arg | Cys | Thr | Asp | Glu | Cys | Arg | Thr | Val | Ile | Glu |
| | | | 195 | | | | | 200 | | | | | 205 | | |
| Asp | Met | Leu | Ala | Met | Pro | Lys | Ala | Ala | Leu | Leu | Asn | Asp | Cys | Val | Cys |
| | 210 | | | | | 215 | | | | | 220 | | | | |
| Asp | Gly | Leu | Glu | Arg | Pro | Ile | Cys | Glu | Ser | Val | Lys | Glu | Asn | Met | Ala |
| 225 | | | | | 230 | | | | | 235 | | | | | 240 |
| Arg | Leu | Cys | Phe | Gly | Ala | Glu | Leu | Gly | Asn | Gly | Pro | Gly | Ser | Ser | Gly |
| | | | | 245 | | | | | 250 | | | | | 255 | |
| Ser | Asp | Gly | Gly | Leu | Asp | Asp | Tyr | Tyr | Asp | Glu | Asp | Tyr | Asp | Asp | Glu |
| | | | 260 | | | | | 265 | | | | | 270 | | |
| Gln | Arg | Thr | Gly | Gly | Ala | Gly | Gly | Glu | Gln | Pro | Leu | Asp | Asp | Asp |
| | | 275 | | | | | 280 | | | | | 285 | | |
| Gly | Val | Pro | His | Pro | Pro | Arg | Pro | Gly | Ser | Gly | Ala | Ala | Ala | Ser | Gly |
| | 290 | | | | | 295 | | | | | 300 | | | | |
| Gly | Arg | Gly | Asp | Leu | Pro | Tyr | Gly | Pro | Gly | Arg | Arg | Ser | Ser | Gly | Gly |
| 305 | | | | | 310 | | | | | 315 | | | | | 320 |
| Gly | Gly | Arg | Leu | Ala | Pro | Arg | Gly | Ala | Trp | Thr | Pro | Leu | Ala | Ser | Ile |
| | | | | 325 | | | | | 330 | | | | | 335 | |
| Leu | Leu | Leu | Leu | Leu | Gly | Pro | Leu | Phe | | | | | | | |
| | | 340 | | | | | 345 | | | | | | | | |

<210> SEQ ID NO 7
<211> LENGTH: 3321
<212> TYPE: DNA
<213> ORGANISM: Homo sapiens

<400> SEQUENCE: 7

```
atgttcaact cgatgacccc accaccaatc agtagctatg cgagccctg  ctgtctccgg    60
cccctcccca gtcaggggc  ccccagtgtg gggacagaag gactgtctgg cccgcccttc   120
tgccaccaag ctaacctcat gtccggcccc cacagttatg gccagccag  agagaccaac   180
agctgcaccg agggcccact cttttcttct ccccggagtg cagtcaagtt gaccaagaag   240
cgggcactgt ccatctcacc tctgtcggat gccagcctgg acctgcagac ggttatccgc   300
acctcaccca gctccctcgt agctttcatc aactcgcgat gcacatctcc aggaggctcc   360
tacggtcatc tctccattgg caccatgagc ccatctctgg gattcccagc cagatgaat   420
caccaaaaag ggccctcgcc ttcctttggg gtccagcctt gtggtcccca tgactctgcc   480
cggggtggga tgatcccaca tcctcagtcc cggggaccct tcccaacttg ccagctgaag   540
tctgagctgg acatgctggt tggcaagtgc cgggaggaac ccttggaagg tgatatgtcc   600
agccccaact ccacaggcat acaggatccc ctgttgggga tgctggatgg gcgggaggac   660
ctcgagagag aggagaagcg tgagcctgaa tctgtgtatg aaactgactg ccgttgggat   720
ggctgcagcc aggaatttga ctcccaagag cagctggtgc accacatcaa cagcgagcac   780
atccacgggg agcggaagga gttcgtgtgc cactgggggg gctgctccag ggagctgagg   840
cccttcaaag cccagtacat gctggtggtt cacatgcgca gacacactgg cgagaagcca   900
cacaagtgca cgtttgaagg gtgccggaag tcatactcac gcctcgaaaa cctgaagacg   960
```

-continued

```
cacctgcggt cacacacggg tgagaagcca tacatgtgtg agcacgaggg ctgcagtaaa    1020
gccttcagca atgccagtga ccgagccaag caccagaatc ggacccattc caatgagaag    1080
ccgtatgtat gtaagctccc tggctgcacc aaacgctata cagatcctag ctcgctgcga    1140
aaacatgtca agacagtgca tggtcctgac gcccatgtga ccaaacggca ccgtgggat    1200
ggcccctgc ctcgggcacc atccatttct acagtggagc ccaagaggga gcgggaagga    1260
ggtcccatca gggaggaaag cagactgact gtgccagagg gtgccatgaa gccacagcca    1320
agccctgggg cccagtcatc ctgcagcagt gaccactccc cggcagggag tgcagccaat    1380
acagacagtg gtgtggaaat gactggcaat gcaggggca gcactgaaga cctctccagc    1440
ttggacgagg gaccttgcat tgctggcact ggtctgtcca ctcttcgccg ccttgagaac    1500
ctcaggctgg accagctaca tcaactccgg ccaataggga cccggggtct caaactgccc    1560
agcttgtccc acaccggtac cactgtgtcc cgccgcgtgg gcccccagt tctcttgaa     1620
cgccgcagca gcagctccag cagcatcagc tctgcctata ctgtcagccg ccgctcctcc    1680
ctggcctctc ctttcccccc tggctcccca ccagagaatg gagcatcctc cctgcctggc    1740
cttatgcctg cccagcacta cctgcttcgg gcaagatatg cttcagccag agggggtggt    1800
acttcgccca ctgcagcatc cagcctggat cggataggtg gtcttcccat gcctccttgg    1860
agaagccgag ccgagtatcc aggatacaac cccaatgcag gggtcacccg gagggccagt    1920
gacccagccc aggctgctga ccgtcctgct ccagctagag tccagaggtt caagagcctg    1980
ggctgtgtcc ataccccacc cactgtggca gggggaggac agaactttga tccttacctc    2040
ccaacctctg tctactcacc acagcccccc agcatcactg agaatgctgc catggatgct    2100
agagggctac aggaagagcc agaagttggg acctccatgg tgggcagtgg tctgaacccc    2160
tatatggact tcccacctac tgatactctg ggatatgggg gacctgaagg ggcagcagct    2220
gagccttatg gagcgagggg tccaggctct ctgcctcttg ggcctggtcc acccaccaac    2280
tatgccccca cccctgtcc ccagcaggcc tcatatcctg accccaccca agaaacatgg    2340
ggtgagttcc cttcccactc tgggctgtac ccaggcccca aggctctagg tggaacctac    2400
agccagtgtc ctcgacttga acattatgga caagtgcaag tcaagccaga acaggggtgc    2460
ccagtggggt ctgactccac aggactggca ccctgcctca atgcccaccc cagtgagggg    2520
cccccacatc cacagcctct cttttcccat taccccagc cctctcctcc caatatctc     2580
cagtcaggcc cctataccca gccaccccct gattatcttc cttcagaacc caggccttgc    2640
ctggactttg attcccccac ccattccaca gggcagctca aggctcagct tgtgtgtaat    2700
tatgttcaat ctcaacagga gctactgtgg gagggtgggg gcaggaaga tgcccccgcc    2760
caggaacctt cctaccagag tcccaagttt ctgggggtt cccaggttag cccaagccgt    2820
gctaaagctc cagtgaacac atatggaccct ggctttggac ccaacttgcc caatcacaag    2880
tcaggttcct atcccacccc ttcaccatgc catgaaaatt ttgtagtggg ggcaaatagg    2940
gcttcacata gggcagcagc accacctcga cttctgcccc cattgcccac ttgctatggg    3000
cctctcaaag tgggaggcac aaaccccagc tgtggtcatc ctgaggtggg caggctagga    3060
gggggtcctg ccttgtaccc tcctcccgaa ggacaggtat gtaaccccct ggactctctt    3120
gatcttgaca acactcagct ggactttgtg gctattctgg atgagcccca ggggctgagt    3180
cctcctcctt cccatgatca gcggggcagc tctggacata ccccacctcc ctctgggccc    3240
cccaacatgg ctgtgggcaa catgagtgtc ttactgagat ccctacctgg ggaaacagaa    3300
ttcctcaact ctagtgccta a                                              3321
```

<210> SEQ ID NO 8
<211> LENGTH: 1106
<212> TYPE: PRT
<213> ORGANISM: Homo sapiens

<400> SEQUENCE: 8

```
Met Phe Asn Ser Met Thr Pro Pro Ile Ser Ser Tyr Gly Glu Pro
1               5                   10                  15

Cys Cys Leu Arg Pro Leu Pro Ser Gln Gly Ala Pro Ser Val Gly Thr
            20                  25                  30

Glu Gly Leu Ser Gly Pro Pro Phe Cys His Gln Ala Asn Leu Met Ser
        35                  40                  45

Gly Pro His Ser Tyr Gly Pro Ala Arg Glu Thr Asn Ser Cys Thr Glu
    50                  55                  60

Gly Pro Leu Phe Ser Ser Pro Arg Ser Ala Val Lys Leu Thr Lys Lys
65                  70                  75                  80

Arg Ala Leu Ser Ile Ser Pro Leu Ser Asp Ala Ser Leu Asp Leu Gln
                85                  90                  95

Thr Val Ile Arg Thr Ser Pro Ser Ser Leu Val Ala Phe Ile Asn Ser
            100                 105                 110

Arg Cys Thr Ser Pro Gly Gly Ser Tyr Gly His Leu Ser Ile Gly Thr
        115                 120                 125

Met Ser Pro Ser Leu Gly Phe Pro Ala Gln Met Asn His Gln Lys Gly
    130                 135                 140

Pro Ser Pro Ser Phe Gly Val Gln Pro Cys Gly Pro His Asp Ser Ala
145                 150                 155                 160

Arg Gly Gly Met Ile Pro His Pro Gln Ser Arg Gly Pro Phe Pro Thr
                165                 170                 175

Cys Gln Leu Lys Ser Glu Leu Asp Met Leu Val Gly Lys Cys Arg Glu
            180                 185                 190

Glu Pro Leu Glu Gly Asp Met Ser Ser Pro Asn Ser Thr Gly Ile Gln
        195                 200                 205

Asp Pro Leu Leu Gly Met Leu Asp Gly Arg Glu Asp Leu Glu Arg Glu
    210                 215                 220

Glu Lys Arg Glu Pro Glu Ser Val Tyr Glu Thr Asp Cys Arg Trp Asp
225                 230                 235                 240

Gly Cys Ser Gln Glu Phe Asp Ser Gln Glu Gln Leu Val His His Ile
                245                 250                 255

Asn Ser Glu His Ile His Gly Glu Arg Lys Glu Phe Val Cys His Trp
            260                 265                 270

Gly Gly Cys Ser Arg Glu Leu Arg Pro Phe Lys Ala Gln Tyr Met Leu
        275                 280                 285

Val Val His Met Arg Arg His Thr Gly Glu Lys Pro His Lys Cys Thr
    290                 295                 300

Phe Glu Gly Cys Arg Lys Ser Tyr Ser Arg Leu Glu Asn Leu Lys Thr
305                 310                 315                 320

His Leu Arg Ser His Thr Gly Glu Lys Pro Tyr Met Cys Glu His Glu
                325                 330                 335

Gly Cys Ser Lys Ala Phe Ser Asn Ala Ser Asp Arg Ala Lys His Gln
            340                 345                 350

Asn Arg Thr His Ser Asn Glu Lys Pro Tyr Val Cys Lys Leu Pro Gly
        355                 360                 365

Cys Thr Lys Arg Tyr Thr Asp Pro Ser Ser Leu Arg Lys His Val Lys
```

```
                370                 375                 380
Thr Val His Gly Pro Asp Ala His Val Thr Lys Arg His Arg Gly Asp
385                 390                 395                 400

Gly Pro Leu Pro Arg Ala Pro Ser Ile Ser Thr Val Glu Pro Lys Arg
            405                 410                 415

Glu Arg Glu Gly Gly Pro Ile Arg Glu Ser Arg Leu Thr Val Pro
            420                 425                 430

Glu Gly Ala Met Lys Pro Gln Pro Ser Pro Gly Ala Gln Ser Ser Cys
            435                 440                 445

Ser Ser Asp His Ser Pro Ala Gly Ser Ala Ala Asn Thr Asp Ser Gly
            450                 455                 460

Val Glu Met Thr Gly Asn Ala Gly Gly Ser Thr Glu Asp Leu Ser Ser
465                 470                 475                 480

Leu Asp Glu Gly Pro Cys Ile Ala Gly Thr Gly Leu Ser Thr Leu Arg
                485                 490                 495

Arg Leu Glu Asn Leu Arg Leu Asp Gln Leu His Gln Leu Arg Pro Ile
            500                 505                 510

Gly Thr Arg Gly Leu Lys Leu Pro Ser Leu Ser His Thr Gly Thr Thr
            515                 520                 525

Val Ser Arg Arg Val Gly Pro Pro Val Ser Leu Glu Arg Ser Ser
            530                 535                 540

Ser Ser Ser Ser Ile Ser Ser Ala Tyr Thr Val Ser Arg Arg Ser Ser
545                 550                 555                 560

Leu Ala Ser Pro Phe Pro Pro Gly Ser Pro Pro Glu Asn Gly Ala Ser
                565                 570                 575

Ser Leu Pro Gly Leu Met Pro Ala Gln His Tyr Leu Leu Arg Ala Arg
            580                 585                 590

Tyr Ala Ser Ala Arg Gly Gly Gly Thr Ser Pro Thr Ala Ala Ser Ser
            595                 600                 605

Leu Asp Arg Ile Gly Gly Leu Pro Met Pro Pro Trp Arg Ser Arg Ala
            610                 615                 620

Glu Tyr Pro Gly Tyr Asn Pro Asn Ala Gly Val Thr Arg Arg Ala Ser
625                 630                 635                 640

Asp Pro Ala Gln Ala Ala Asp Arg Pro Ala Pro Ala Arg Val Gln Arg
                645                 650                 655

Phe Lys Ser Leu Gly Cys Val His Thr Pro Thr Val Ala Gly Gly
            660                 665                 670

Gly Gln Asn Phe Asp Pro Tyr Leu Pro Thr Ser Val Tyr Ser Pro Gln
            675                 680                 685

Pro Pro Ser Ile Thr Glu Asn Ala Ala Met Asp Ala Arg Gly Leu Gln
            690                 695                 700

Glu Glu Pro Glu Val Gly Thr Ser Met Val Gly Ser Gly Leu Asn Pro
705                 710                 715                 720

Tyr Met Asp Phe Pro Pro Thr Asp Thr Leu Gly Tyr Gly Gly Pro Glu
                725                 730                 735

Gly Ala Ala Ala Glu Pro Tyr Gly Ala Arg Gly Pro Gly Ser Leu Pro
            740                 745                 750

Leu Gly Pro Gly Pro Thr Asn Tyr Gly Pro Asn Pro Cys Pro Gln
            755                 760                 765

Gln Ala Ser Tyr Pro Asp Pro Thr Gln Glu Thr Trp Gly Glu Phe Pro
            770                 775                 780

Ser His Ser Gly Leu Tyr Pro Gly Pro Lys Ala Leu Gly Gly Thr Tyr
785                 790                 795                 800
```

Ser Gln Cys Pro Arg Leu Glu His Tyr Gly Gln Val Gln Val Lys Pro
              805                 810                 815

Glu Gln Gly Cys Pro Val Gly Ser Asp Ser Thr Gly Leu Ala Pro Cys
        820                 825                 830

Leu Asn Ala His Pro Ser Glu Gly Pro Pro His Pro Gln Pro Leu Phe
                835                 840                 845

Ser His Tyr Pro Gln Pro Ser Pro Pro Gln Tyr Leu Gln Ser Gly Pro
        850                 855                 860

Tyr Thr Gln Pro Pro Pro Asp Tyr Leu Pro Ser Glu Pro Arg Pro Cys
865                 870                 875                 880

Leu Asp Phe Asp Ser Pro Thr His Ser Thr Gly Gln Leu Lys Ala Gln
                885                 890                 895

Leu Val Cys Asn Tyr Val Gln Ser Gln Gln Glu Leu Leu Trp Glu Gly
                900                 905                 910

Gly Gly Arg Glu Asp Ala Pro Ala Gln Glu Pro Ser Tyr Gln Ser Pro
        915                 920                 925

Lys Phe Leu Gly Gly Ser Gln Val Ser Pro Ser Arg Ala Lys Ala Pro
        930                 935                 940

Val Asn Thr Tyr Gly Pro Gly Phe Gly Pro Asn Leu Pro Asn His Lys
945                 950                 955                 960

Ser Gly Ser Tyr Pro Thr Pro Ser Pro Cys His Glu Asn Phe Val Val
                965                 970                 975

Gly Ala Asn Arg Ala Ser His Arg Ala Ala Pro Pro Arg Leu Leu
        980                 985                 990

Pro Pro Leu Pro Thr Cys Tyr Gly Pro Leu Lys Val Gly Gly Thr Asn
        995                 1000                1005

Pro Ser Cys Gly His Pro Glu Val Gly Arg Leu Gly Gly Pro
    1010                1015                1020

Ala Leu Tyr Pro Pro Glu Gly Gln Val Cys Asn Pro Leu Asp
    1025                1030                1035

Ser Leu Asp Leu Asp Asn Thr Gln Leu Asp Phe Val Ala Ile Leu
    1040                1045                1050

Asp Glu Pro Gln Gly Leu Ser Pro Pro Ser His Asp Gln Arg
    1055                1060                1065

Gly Ser Ser Gly His Thr Pro Pro Pro Ser Gly Pro Pro Asn Met
    1070                1075                1080

Ala Val Gly Asn Met Ser Val Leu Leu Arg Ser Leu Pro Gly Glu
    1085                1090                1095

Thr Glu Phe Leu Asn Ser Ser Ala
    1100                1105

<210> SEQ ID NO 9
<211> LENGTH: 4635
<212> TYPE: DNA
<213> ORGANISM: Mus musculus

<400> SEQUENCE: 9
atggagactt ctgccccagc ccctgcactg gagaagaaag aagccaagag tggtctcttg      60
gaggacagca gcttccccga cccagggaaa aaggcctgtc ctctggcggt ggccgcagct     120
gtagccgccc acggagttcc tcagcagctc ctgccggctt ccacgcgcc tttgccgatt     180 gacatgagac accaggaggg aaggtaccat tatgaccctc actctgtcca cagtgtacac     240
gggcctccca ccctaagtgg cagccctgtc atctcagata tctccttgat acgactttct     300

```
ccacaccctg ctggccctgg agagtcaccc ttcagcgccc accacccecta cgtgaacccc      360 catatggagc actacctccg gtctgtgcac agcagcccca cactctcaat gatctctgcc      420
gccaggggcc tcagccctgc tgatgtggcc cacgaacatc tgaaagagag gggactcttt      480
agcctcgcag ccccaggcac caaccecttca gactattacc accagatgac cctcatggca      540
agccacccca cccecttatgg ggaccttcta atgcagagcg ggggtgctgc tagcgcaccc      600
catctccatg actacctcaa ccctgtggat gcatcacgat tctctagtcc acgtgtgacc      660
ccacgactga gccgcaagcg ggctctgtcc atctccccgc tctcagatgc cagcctcgac      720
ctacaacgca tgattcggac ctctcccaac tcgctggtag cttacatcaa caactccagg      780
agcagctcag cagccagtgg ctcttatgga catctgtctg ctggtgccct cagcccagcc      840
ttcacttttc cccacecccat caatcctgtg gcctaccagc agatcctgag ccagcagcgg      900
ggcctgggct cagcctttgg acacacacca cccectgatcc agccttcacc caccttcttg      960
gcccagcagc ccatgactct cacctccatc agcaccatgc ctacccaact cagcagcagt     1020
agcagcaact gtctaaatga tgccaaccag aacaagcaga cagcgagtc agctgtgagc     1080 agcaccgtga accccatcac cattcataag cggagcaagg tcaagactga ggctgagggc     1140
ctgcgtccag catcccecgct tggactgaca caggagcagc tggccgatct caaggaagac     1200
ctggacaggg atgactgtaa gcaggaggcc gaggtggtca tctacgagac caactgccac     1260
tgggcagact gcaccaagga gtatgacaca caggagcagc tggtgcatca tatcaacaat     1320
gaacacatcc acggggagaa gaaggagttc gtgtgccgct ggcaggcctg cacgagagag     1380
cagaagccct tcaaggccca gtacatgctg gttgttcaca tgcgcagaca cacggggtgag     1440 aagccacaca agtgcacgtt cgaaggctgt tccaaggcct actctcgcct ggagaacctg     1500
aagacacacc tgcgttcaca cacaggagag aagccatatg tgtgtgaaca cgaaggctgt     1560
aacaaagcct tctccaatgc ctcagaccgc gccaagcacc agaaccgcac tcactccaat     1620
gagaaaccct acatctgcaa gatcccaggc tgcaccaaga ggtacacaga ccccagctca     1680
ctccgcaagc atgtgaagac tgtccatggg ccagacgccc atgtcaccaa gaaacagcgt     1740
aatgatgtgc atgtccgtgc tccactgctc aaggagaatg gggataatga ggccagcgcc     1800
gagccaggtg gccggggacc tgaggagagt gtggaggcca gtagcaccag ccacactgtg     1860
gaggactgcc tacatatcaa agccatcaag acagagagct ccgggctttg tcagtccagc     1920 ccegggcccec agtcatcctg cagcagcgag ccctctcccc tgggcagtgc ccecaacaat     1980 gacagtggca tggagatgcc ggggacaggg cctgggagtc tgggagacct gacagcactg     2040
gctgacacgt gtccaggagc tgacacctca gccctggctg caccctccac tggtggcctg     2100
cagctgcgca acacatgag caccgtgcat cgctttgagc agctgaagag agagaagctc     2160
aagtcactga aggattcctg ctcgtgggcc ggcccagctc cacacaccccg caacaccaag     2220 ctgcctcccc ttccagtcaa tggttctgtc ctggaaaact tcaacaatac aggggggcgt      2280
ggaccggcag gactgctgcc cagccagcgg ctaccagagc tgaccgaagt gacgatgctg      2340
agccagctgc aggaacgaag agacagctcc accagcacca tgagctcggc ctacactgtg      2400 agccgccget cctctggcat ctccccatac ttctctagcc gtcgctccag cgaggcttcg      2460
cctctcggtg gcctacgccc gcacaacgcc agctcagcag actcctatga ccccatctcc      2520
acagatgcct ctcggcgctc cagtgaagcc agccagtgca gtggcggtgg cccagggctg      2580
ctcaacctca cacctgcgca gcagtacaac ctgcgtgcca gtacgcagc ggccacaggt      2640 ggaccaccgc ccacgccact gccgggcctc gatcgtgtaa gccttcgtac ccgcctggcc      2700
```

```
ttgctggatg ctcctgagcg tgcacttcct ggtgcctgcc cacatccact ggggccacgg    2760
cgtggcagcg atgggcctac ctatagccat ggtcatggcc atggctacgc aggtgcggct    2820
ccagcattcc cccacgaggg gccaaacagc agcacacggc gggccagcga ccctgtgcgg    2880
cgccctgacc cccttattct gcctcgagtg caacgtttcc acagtaccca aacatgaat    2940 ccaggttcac tgccaccctg cgctgatcgg cgtggcctgc acgtacagag ccaccccagc    3000
gtagacagca acctgacccg caacgcctac tctcccagac cccctagcat caatgagaac    3060
gtggtgatgg aggccgtggc tgctggggta gacggcccag gctagagtg cgacctgggg    3120 ctggtggagg atgagctggt gctgccagat gatgtggtac agtacatcaa ggctcacacc    3180
ggtggtacct tggatgacgg cattcggcag gggtatccca cagaaggtac tggcttcccc    3240
gagaactcta agctgcccag tcctgggcta caaggccacc gcaggctagc agctgccgac    3300
tccaacatgg gtccttctgc tcctggactc gggggctgcc agctgagcta cagcccctcc    3360
tccaacctca acaagagcaa catgcctgtg cagtggaatg aggtgagttc tggcaccgtg    3420
gatgccctgc ctacccaggt gaagccacct cctttccctc acagcaacct ggctgtggtc    3480
caacagaagc cagcctttgg ccagtatcca ggatataatc cacaatccgt gcagagcagc    3540
tccggaggtc tagacagcac ccagccgcac ctacagcttc gaggagcccc ctctgcatca    3600
agagggagct acacgcaaca gcctcgacag ccagctgcag gcagtcagtg cctgggtatg    3660
agtgcggcca tgagcccgca ggccagctac agccaagccc accccagct gagcccaaac    3720 attgtcagcg atctctgaa ccagttttct ccctcctgca gcaatatggc agccaagccc    3780
agccacctgg gactccctca gcaaatggaa gttgtcccca atgccaccat catgaatggc    3840
catcaacggg agcacggggt ccccaattca tccctggctg cggtgtcaca acctcaccca    3900
gtcctgagct atccccagca ggacagctac caacagggct ccaaccttct gtcatcccat    3960
cagcctggct tcatggagtc ccagcagaac gcgggctttg gtctcatgca gcctcggcca    4020
cccctggaac ccaacacggc cagccgtcac cgtggagtac gttctgggca acagcagttg    4080
tatgccagga ccactggcca agccatggtc acatcagcca accaagagac agcagaagct    4140
atgcccaagg accagcagg gaccatggta tccctagctc ctcagccatc tcaggacaca    4200
gggcgggcac aagatcagaa cacgctatac tactatggcc agatccacat gtatgaacag    4260
aatggaggct gcccagccgt gcagcccag ccgccacaac cacaagcttg tcagacagt    4320 atccagcctg agcctttgcc ttcaccggga gtcaaccagg tgtctagcac cgtggactcc    4380
cagctcctgg agcccccca gattgacttt gatgccatca tggatgatgg tgatcactcg    4440
agtttgtttt ctggtgcact gagcccaacc cttctccaca atctctccca gaattcctca    4500
cgcctcacca cacccggaa ttccttgaca ctgccctcca tccctgcggg catcagcaac    4560
atggccgtgg gcgacatgag ttccatgctc accagcctgg ctgaagagag caagttttta    4620
aacatgatga cctaa                                                    4635
```

<210> SEQ ID NO 10
<211> LENGTH: 1544
<212> TYPE: PRT
<213> ORGANISM: Mus musculus

<400> SEQUENCE: 10

Met Glu Thr Ser Ala Pro Ala Pro Ala Leu Glu Lys Lys Glu Ala Lys
1               5                   10                  15

Ser Gly Leu Leu Glu Asp Ser Ser Phe Pro Asp Pro Gly Lys Lys Ala

-continued

```
                 20                  25                  30
Cys Pro Leu Ala Val Ala Ala Val Ala Ala His Gly Val Pro Gln
             35                  40                  45
Gln Leu Leu Pro Ala Phe His Ala Pro Leu Pro Ile Asp Met Arg His
 50                  55                  60
Gln Glu Gly Arg Tyr His Tyr Asp Pro His Ser Val His Ser Val His
 65                  70                  75                  80
Gly Pro Pro Thr Leu Ser Gly Ser Pro Val Ile Ser Asp Ile Ser Leu
                 85                  90                  95
Ile Arg Leu Ser Pro His Pro Ala Gly Pro Gly Glu Ser Pro Phe Ser
             100                 105                 110
Ala His His Pro Tyr Val Asn Pro His Met Glu His Tyr Leu Arg Ser
             115                 120                 125
Val His Ser Ser Pro Thr Leu Ser Met Ile Ser Ala Ala Arg Gly Leu
             130                 135                 140
Ser Pro Ala Asp Val Ala His Glu His Leu Lys Glu Arg Gly Leu Phe
145                 150                 155                 160
Ser Leu Ala Ala Pro Gly Thr Asn Pro Ser Asp Tyr Tyr His Gln Met
             165                 170                 175
Thr Leu Met Ala Ser His Pro Thr Pro Tyr Gly Asp Leu Leu Met Gln
             180                 185                 190
Ser Gly Gly Ala Ala Ser Ala Pro His Leu His Asp Tyr Leu Asn Pro
             195                 200                 205
Val Asp Ala Ser Arg Phe Ser Ser Pro Arg Val Thr Pro Arg Leu Ser
    210                 215                 220
Arg Lys Arg Ala Leu Ser Ile Ser Pro Leu Ser Asp Ala Ser Leu Asp
225                 230                 235                 240
Leu Gln Arg Met Ile Arg Thr Ser Pro Asn Ser Leu Val Ala Tyr Ile
             245                 250                 255
Asn Asn Ser Arg Ser Ser Ser Ala Ala Ser Gly Ser Tyr Gly His Leu
             260                 265                 270
Ser Ala Gly Ala Leu Ser Pro Ala Phe Thr Phe Pro His Pro Ile Asn
             275                 280                 285
Pro Val Ala Tyr Gln Gln Ile Leu Ser Gln Gln Arg Gly Leu Gly Ser
             290                 295                 300
Ala Phe Gly His Thr Pro Pro Leu Ile Gln Pro Ser Pro Thr Phe Leu
305                 310                 315                 320
Ala Gln Gln Pro Met Thr Leu Thr Ser Ile Ser Thr Met Pro Thr Gln
             325                 330                 335
Leu Ser Ser Ser Ser Asn Cys Leu Asn Asp Ala Asn Gln Asn Lys
             340                 345                 350
Gln Asn Ser Glu Ser Ala Val Ser Ser Thr Val Asn Pro Ile Thr Ile
             355                 360                 365
His Lys Arg Ser Lys Val Lys Thr Glu Ala Glu Gly Leu Arg Pro Ala
             370                 375                 380
Ser Pro Leu Gly Leu Thr Gln Glu Gln Leu Ala Asp Leu Lys Glu Asp
385                 390                 395                 400
Leu Asp Arg Asp Asp Cys Lys Gln Glu Ala Glu Val Val Ile Tyr Glu
             405                 410                 415
Thr Asn Cys His Trp Ala Asp Cys Thr Lys Glu Tyr Asp Thr Gln Glu
             420                 425                 430
Gln Leu Val His His Ile Asn Asn Glu His Ile His Gly Glu Lys Lys
             435                 440                 445
```

-continued

```
Glu Phe Val Cys Arg Trp Gln Ala Cys Thr Arg Glu Gln Lys Pro Phe
    450                 455                 460
Lys Ala Gln Tyr Met Leu Val Val His Met Arg His Thr Gly Glu
465                 470                 475                 480
Lys Pro His Lys Cys Thr Phe Glu Gly Cys Ser Lys Ala Tyr Ser Arg
                485                 490                 495
Leu Glu Asn Leu Lys Thr His Leu Arg Ser His Thr Gly Glu Lys Pro
            500                 505                 510
Tyr Val Cys Glu His Glu Gly Cys Asn Lys Ala Phe Ser Asn Ala Ser
        515                 520                 525
Asp Arg Ala Lys His Gln Asn Arg Thr His Ser Asn Glu Lys Pro Tyr
    530                 535                 540
Ile Cys Lys Ile Pro Gly Cys Thr Lys Arg Tyr Thr Asp Pro Ser Ser
545                 550                 555                 560
Leu Arg Lys His Val Lys Thr Val His Gly Pro Asp Ala His Val Thr
                565                 570                 575
Lys Lys Gln Arg Asn Asp Val His Val Arg Ala Pro Leu Leu Lys Glu
            580                 585                 590
Asn Gly Asp Asn Glu Ala Ser Ala Glu Pro Gly Gly Arg Gly Pro Glu
        595                 600                 605
Glu Ser Val Glu Ala Ser Ser Thr Ser His Thr Val Glu Asp Cys Leu
    610                 615                 620
His Ile Lys Ala Ile Lys Thr Glu Ser Ser Gly Leu Cys Gln Ser Ser
625                 630                 635                 640
Pro Gly Ala Gln Ser Ser Cys Ser Ser Glu Pro Ser Pro Leu Gly Ser
                645                 650                 655
Ala Pro Asn Asn Asp Ser Gly Met Glu Met Pro Gly Thr Gly Pro Gly
            660                 665                 670
Ser Leu Gly Asp Leu Thr Ala Leu Ala Asp Thr Cys Pro Gly Ala Asp
        675                 680                 685
Thr Ser Ala Leu Ala Ala Pro Ser Thr Gly Gly Leu Gln Leu Arg Lys
    690                 695                 700
His Met Ser Thr Val His Arg Phe Glu Gln Leu Lys Arg Glu Lys Leu
705                 710                 715                 720
Lys Ser Leu Lys Asp Ser Cys Ser Trp Ala Gly Pro Ala Pro His Thr
                725                 730                 735
Arg Asn Thr Lys Leu Pro Pro Leu Pro Val Asn Gly Ser Val Leu Glu
            740                 745                 750
Asn Phe Asn Asn Thr Gly Gly Gly Pro Ala Gly Leu Leu Pro Ser
        755                 760                 765
Gln Arg Leu Pro Glu Leu Thr Glu Val Thr Met Leu Ser Gln Leu Gln
    770                 775                 780
Glu Arg Arg Asp Ser Ser Thr Ser Thr Met Ser Ser Ala Tyr Thr Val
785                 790                 795                 800
Ser Arg Arg Ser Ser Gly Ile Ser Pro Tyr Phe Ser Ser Arg Arg Ser
                805                 810                 815
Ser Glu Ala Ser Pro Leu Gly Gly Leu Arg Pro His Asn Ala Ser Ser
            820                 825                 830
Ala Asp Ser Tyr Asp Pro Ile Ser Thr Asp Ala Ser Arg Arg Ser Ser
        835                 840                 845
Glu Ala Ser Gln Cys Ser Gly Gly Pro Gly Leu Leu Asn Leu Thr
    850                 855                 860
```

```
Pro Ala Gln Gln Tyr Asn Leu Arg Ala Lys Tyr Ala Ala Thr Gly
865                 870                 875                 880

Gly Pro Pro Thr Pro Leu Pro Gly Leu Asp Arg Val Ser Leu Arg
            885                 890                 895

Thr Arg Leu Ala Leu Leu Asp Ala Pro Glu Arg Ala Leu Pro Gly Ala
        900                 905                 910

Cys Pro His Pro Leu Gly Pro Arg Arg Gly Ser Asp Gly Pro Thr Tyr
        915                 920                 925

Ser His Gly His Gly His Gly Tyr Ala Gly Ala Ala Pro Ala Phe Pro
    930                 935                 940

His Glu Gly Pro Asn Ser Ser Thr Arg Arg Ala Ser Asp Pro Val Arg
945                 950                 955                 960

Arg Pro Asp Pro Leu Ile Leu Pro Arg Val Gln Arg Phe His Ser Thr
                965                 970                 975

His Asn Met Asn Pro Gly Ser Leu Pro Pro Cys Ala Asp Arg Arg Gly
            980                 985                 990

Leu His Val Gln Ser His Pro Ser Val Asp Ser Asn Leu Thr Arg Asn
        995                 1000                1005

Ala Tyr Ser Pro Arg Pro Pro Ser Ile Asn Glu Asn Val Val Met
    1010                1015                1020

Glu Ala Val Ala Ala Gly Val Asp Gly Pro Gly Leu Glu Cys Asp
    1025                1030                1035

Leu Gly Leu Val Glu Asp Glu Leu Val Leu Pro Asp Asp Val Val
    1040                1045                1050

Gln Tyr Ile Lys Ala His Thr Gly Gly Thr Leu Asp Asp Gly Ile
    1055                1060                1065

Arg Gln Gly Tyr Pro Thr Glu Gly Thr Gly Phe Pro Glu Asn Ser
    1070                1075                1080

Lys Leu Pro Ser Pro Gly Leu Gln Gly His Arg Arg Leu Ala Ala
    1085                1090                1095

Ala Asp Ser Asn Met Gly Pro Ser Ala Pro Gly Leu Gly Gly Cys
    1100                1105                1110

Gln Leu Ser Tyr Ser Pro Ser Ser Asn Leu Asn Lys Ser Asn Met
    1115                1120                1125

Pro Val Gln Trp Asn Glu Val Ser Ser Gly Thr Val Asp Ala Leu
    1130                1135                1140

Pro Thr Gln Val Lys Pro Pro Pro Phe Pro His Ser Asn Leu Ala
    1145                1150                1155

Val Val Gln Gln Lys Pro Ala Phe Gly Gln Tyr Pro Gly Tyr Asn
    1160                1165                1170

Pro Gln Ser Val Gln Ser Ser Gly Gly Leu Asp Ser Thr Gln
    1175                1180                1185

Pro His Leu Gln Leu Arg Gly Ala Pro Ser Ala Ser Arg Gly Ser
    1190                1195                1200

Tyr Thr Gln Gln Pro Arg Gln Pro Ala Ala Gly Ser Gln Cys Leu
    1205                1210                1215

Gly Met Ser Ala Ala Met Ser Pro Gln Ala Ser Tyr Ser Gln Ala
    1220                1225                1230

His Pro Gln Leu Ser Pro Asn Ile Val Ser Gly Ser Leu Asn Gln
    1235                1240                1245

Phe Ser Pro Ser Cys Ser Asn Met Ala Ala Lys Pro Ser His Leu
    1250                1255                1260

Gly Leu Pro Gln Gln Met Glu Val Val Pro Asn Ala Thr Ile Met
```

```
                    1265                1270                1275
Asn Gly His Gln Arg Glu His Gly Val Pro Asn Ser Ser Leu Ala
        1280                1285                1290
Ala Val Ser Gln Pro His Pro Val Leu Ser Tyr Pro Gln Gln Asp
        1295                1300                1305
Ser Tyr Gln Gln Gly Ser Asn Leu Leu Ser Ser His Gln Pro Gly
        1310                1315                1320
Phe Met Glu Ser Gln Gln Asn Ala Gly Phe Gly Leu Met Gln Pro
        1325                1330                1335
Arg Pro Pro Leu Glu Pro Asn Thr Ala Ser Arg His Arg Gly Val
        1340                1345                1350
Arg Ser Gly Gln Gln Gln Leu Tyr Ala Arg Thr Thr Gly Gln Ala
        1355                1360                1365
Met Val Thr Ser Ala Asn Gln Glu Thr Ala Glu Ala Met Pro Lys
        1370                1375                1380
Gly Pro Ala Gly Thr Met Val Ser Leu Ala Pro Gln Pro Ser Gln
        1385                1390                1395
Asp Thr Gly Arg Ala Gln Asp Gln Asn Thr Leu Tyr Tyr Tyr Gly
        1400                1405                1410
Gln Ile His Met Tyr Glu Gln Asn Gly Gly Cys Pro Ala Val Gln
        1415                1420                1425
Pro Gln Pro Pro Gln Pro Gln Ala Cys Ser Asp Ser Ile Gln Pro
        1430                1435                1440
Glu Pro Leu Pro Ser Pro Gly Val Asn Gln Val Ser Ser Thr Val
        1445                1450                1455
Asp Ser Gln Leu Leu Glu Pro Pro Gln Ile Asp Phe Asp Ala Ile
        1460                1465                1470
Met Asp Asp Gly Asp His Ser Ser Leu Phe Ser Gly Ala Leu Ser
        1475                1480                1485
Pro Thr Leu Leu His Asn Leu Ser Gln Asn Ser Ser Arg Leu Thr
        1490                1495                1500
Thr Pro Arg Asn Ser Leu Thr Leu Pro Ser Ile Pro Ala Gly Ile
        1505                1510                1515
Ser Asn Met Ala Val Gly Asp Met Ser Ser Met Leu Thr Ser Leu
        1520                1525                1530
Ala Glu Glu Ser Lys Phe Leu Asn Met Met Thr
        1535                1540

<210> SEQ ID NO 11
<211> LENGTH: 4743
<212> TYPE: DNA
<213> ORGANISM: Homo sapiens

<400> SEQUENCE: 11
atggaggccc agtccacag ctccacgacc actgaaaaga aaaagttga gaattccata    60 gtgaagtgct ccactcgaac agatgtgagc gagaaagccg ttgcctccag caccacttct   120
aatgaggatg aaagtcctgg acagacttat cacagagaga aagaaacgc aatcactatg   180 cagccacaga atgtccaggg gctcagcaaa gtcagtgagg aaccttcaac atcgagtgac   240
gagagggcct cattgatcaa gaaagagatc catgggtccc tgccacacgt ggcggagccc   300
tctgtgccgt accgcgggac ggtgtttgcc atggacccca ggaatggtta catggagccc   360
cactaccacc ctcctcatct ttttcctgcc ttcatcctc ctgtaccaat tgatgccaga   420
catcatgagg gccgttacca ttacgatcca tctccgattc ctccattgca tatgacttcc   480
```

```
gccttatcta gtagccctac gtatccggac ctgcccttca ttaggatctc cccacaccgg      540
aaccccactg ctgcttccga gtctcccttc agccctccac atccctacat taatccctac      600
atggactata tccgctcctt gcacagcagc ccatcgctct ccatgatctc agcaacccgt      660
gggctgagcc ctacagatgc gccccatgca ggagtcagcc cagcagaata ctatcatcag      720
atggccctgc taactggcca gcgcagcccc tatgcagaca ttattccctc agctgccacc      780
gccggcacgg gggccatcca catggaatat cttcatgcta tggatagcac cagattctcc      840
agccccaggc tgtcagccag gccgagccga aaacgtacac tgtccatatc accactctcc      900
gatcatagct ttgaccttca gaccatgata aggacgtctc ccaactcctt ggtcacgatt      960
ctcaataatt cccgtagcag ctcttcagca agtggctcct atggtcactt atctgcaagt     1020
gcaatcagcc ctgccttgag cttcacctac tcttccgcgc ccgtctctct ccacatgcat     1080
cagcagatcc taagccgaca acagagctta ggttcagcct ttggacacag ccctccactc     1140
atccaccctg ccccaacttt tccaacacag aggcctattc cagggatccc tacggttctg     1200
aaccccgtcc aggtcagctc cggcccttct gagtcctcac agaacaagcc cacgagtgag     1260
tctgcagtga gcagcactgg tgacccgatg cacaacaaga ggtccaagat caaacccgat     1320
gaagacctcc ccagcccagg ggctcggggg cagcaggaac agcccgaagg aacaaccctt     1380
gtcaaggagg aaggggacaa agatgaaagc aaacaggagc tgaagtcat ctatgagaca     1440 aactgccact gggaaggctg cgcgagggag ttcgacaccc aagagcagct tgtgcaccat     1500
ataaataacg accatattca tggagagaag aaggagttcg tgtgcaggtg gctggactgc     1560
tcaagagagc agaaacccct caaagcccag tatatgttgg tagtgcatat gagaagacac     1620
acgggcgaga agcctcacaa atgcactttt gaaggttgca caaaggccta ctcgagacta     1680
gaaaacttga aaacacactt gagatctcac actggagaga accatacgt ctgtgagcac     1740 gaaggttgca acaaggcttt ctcaaatgcc tctgatcgcg ccaaacacca aaacagaacg     1800
cattccaatg agaaaccata tgtgtgcaaa atcccaggct gcactaagcg ttacacagac     1860
ccaagctccc tccggaaaca tgtgaagaca gtgcatggcc cagaggctca tgtcaccaag     1920
aagcagcgag gggacatcca tcctcggccg ccaccccga gagattccgg cagccattca     1980
cagtccaggt cgcctggccg accgactcag ggagcccttg gtgagcagca ggacctcagc     2040
aacactacct caaagcggga agaatgcctc caggtgaaaa ccgtcaaggc agagaagcca     2100
atgacatctc agccaagccc tggtggtcag tcttcatgca gcagccaaca gtcccccatc     2160
agcaactatt ccaacagtgg gctcgagctt cctctgaccg atggaggtag tataggagac     2220
ctcagtgcca tcgatgaaac cccaatcatg gactcaacca tttccactgc aaccacagcc     2280
cttgctttgc aagccaggag aaacccggca gggaccaaat ggatggagca cgtaaaacta     2340
gaaaggctaa acaagtgaa tggaatgttt ccgcgactga cccattct accccctaaa     2400 gcccctgcgg tctctcctct cataggaaat ggcacacagt ccaacaacac ctgcagcttg     2460
ggtgggccca tgacgcttct cccgggcaga agcgacctct ctggggtgga cgtcactatg     2520
ctgaacatgc tcaacagaag ggacagcagc gccagcacca tcagctcggc ctacctgagc     2580
agccgccgct cctcagggat ctcgccctgc ttctccagcc gccgctccag cgaggcgtca     2640
caggccgagg gccggccgca gaacgtgagc gtggccgact cctacgaccc catctccacc     2700
gacgcctcgc gccgctccag cgaagccagc cagagcgacg gcctgccag cctgctcagc     2760 ctcacgcccg cccagcagta ccgcctcaag gccaagtacg cggctgccac aggagggccg     2820
```

| | |
|---|---|
| ccgccgacgc ccctgcccaa catggagagg atgagcctga agacgcgcct ggcgctgctc | 2880 |
| ggggatgccc tcgagcctgg cgtggccctg cctccagttc atgccccgag gaggtgcagc | 2940 |
| gacgggggag cccacggcta cgggcggcgc cacctgcagc cgcacgatgc gccgggccac | 3000 |
| ggcgtgagga gggccagcga cccggtgcgg acaggctccg agggcctggc cctgcctcgt | 3060 |
| gtgccgcgct tcagcagcct cagcagctgc aaccccccgg cgatggccac gtccgcggag | 3120 |
| aagcgcagtc tcgtgcttca gaattacacg cggcccgagg cggccagtc ccgaaacttc | 3180 |
| cactcgtccc cctgtcctcc cagcatcacc gagaacgtca cctggagtc cctgaccatg | 3240 |
| gacgctgatg ccaacctgaa cgatgaggat ttcctgccgg acgacgtggt gcagtattta | 3300 |
| aattcccaga accaagcagg gtacgagcag cacttcccca gcgccctccc ggacgacagc | 3360 |
| aaagtgcccc acgggcccgg tgactttgac gcgcccgggc tgccagacag ccacgctggc | 3420 |
| cagcagttcc atgccctcga gcagcctgc cccgagggca gcaaaaccga cctgcccatt | 3480 |
| cagtggaacg aagtcagctc cggaagcgcc gacctgtcct cctccaagct caagtgtggg | 3540 |
| ccgcggcccg ctgtgccgca gactcgcgcc tttgggttct gcaacggcat ggtcgtccac | 3600 |
| ccgcagaacc ccttgaggag cgggcctgct gggggctatc agaccctcgg ggagaacagc | 3660 |
| aaccccctacg gtgcccaga gcacttgatg ctccacaaca gccccggaag tggcaccagt | 3720 |
| ggaaacgcct tccatgaaca gccctgtaag gccccgcagt atgggaactg tctcaacagg | 3780 |
| cagccagtgg cccctggtgc actcgacggt gcctgtggtg ccgggattca agcctcaaag | 3840 |
| ctgaagagca cccccatgca agggagcggg ggccagctga atttcggcct gccggtagcg | 3900 |
| ccaaatgagt cagctggcag catggtgaat ggcatgcaga accaggaccc agtgggacag | 3960 |
| gggtacctgg ctcaccagct cctcggcgac agcatgcagc acccgggggc aggccgcccc | 4020 |
| ggtcagcaga tgcttgggca gattagtgct acctcacaca tcaacatcta ccaagggcca | 4080 |
| gagagctgcc tgccaggggc tcacggcatg ggcagccagc cgtcaagctt ggcagttgtc | 4140 |
| aggggctacc agccatgtgc cagctttggg ggcagcaggc gccaggctat gccgagggac | 4200 |
| agccttgctc tgcagtcagg acagctcagt gacacaagtc agacctgcag ggtgaatggt | 4260 |
| atcaagatgg agatgaaagg gcagcccccat ccgctgtgct ctaatctgca gaattactct | 4320 |
| ggtcagttct atgaccaaac cgtgggcttc agtcagcaag acacgaaagc tggttcattc | 4380 |
| tctatttcag acgccagctg cctgctacag gggaccagcg ccaaaaactc tgagttactt | 4440 |
| tccccaggtg ctaatcaggt gacaagcaca gtggacagcc tcgacagcca tgacctggaa | 4500 |
| ggggtacaga ttgacttcga tgccatcata gacgatgggg accactccag cctgatgtcg | 4560 |
| ggggccctga gccaagtat cattcagaac ctttcccata gctcctcccg cctcaccacg | 4620 |
| cctcgggcgt ccctcccatt cccagcgctg tccatgagca ccaccaacat ggctatcggg | 4680 |
| gacatgagtt ctttgctgac ctccctagcg gaagaaagca aattccttgc agttatgcaa | 4740 |
| tag | 4743 |

<210> SEQ ID NO 12
<211> LENGTH: 1580
<212> TYPE: PRT
<213> ORGANISM: Homo sapiens

<400> SEQUENCE: 12

```
Met Glu Ala Gln Ser His Ser Ser Thr Thr Thr Glu Lys Lys Lys Val
1               5                   10                  15

Glu Asn Ser Ile Val Lys Cys Ser Thr Arg Thr Asp Val Ser Glu Lys
            20                  25                  30
```

-continued

```
Ala Val Ala Ser Ser Thr Thr Ser Asn Glu Asp Glu Ser Pro Gly Gln
            35                  40                  45

Thr Tyr His Arg Glu Arg Arg Asn Ala Ile Thr Met Gln Pro Gln Asn
        50                  55                  60

Val Gln Gly Leu Ser Lys Val Ser Glu Glu Pro Ser Thr Ser Ser Asp
65                  70                  75                  80

Glu Arg Ala Ser Leu Ile Lys Lys Glu Ile His Gly Ser Leu Pro His
                85                  90                  95

Val Ala Glu Pro Ser Val Pro Tyr Arg Gly Thr Val Phe Ala Met Asp
                100                 105                 110

Pro Arg Asn Gly Tyr Met Glu Pro His Tyr His Pro His Leu Phe
            115                 120                 125

Pro Ala Phe His Pro Pro Val Pro Ile Asp Ala Arg His His Glu Gly
            130                 135                 140

Arg Tyr His Tyr Asp Pro Ser Pro Ile Pro Pro Leu His Met Thr Ser
145                 150                 155                 160

Ala Leu Ser Ser Pro Thr Tyr Pro Asp Leu Pro Phe Ile Arg Ile
                165                 170                 175

Ser Pro His Arg Asn Pro Thr Ala Ala Ser Glu Ser Pro Phe Ser Pro
                180                 185                 190

Pro His Pro Tyr Ile Asn Pro Tyr Met Asp Tyr Ile Arg Ser Leu His
            195                 200                 205

Ser Ser Pro Ser Leu Ser Met Ile Ser Ala Thr Arg Gly Leu Ser Pro
            210                 215                 220

Thr Asp Ala Pro His Ala Gly Val Ser Pro Ala Glu Tyr Tyr His Gln
225                 230                 235                 240

Met Ala Leu Leu Thr Gly Gln Arg Ser Pro Tyr Ala Asp Ile Ile Pro
                245                 250                 255

Ser Ala Ala Thr Ala Gly Thr Gly Ala Ile His Met Glu Tyr Leu His
                260                 265                 270

Ala Met Asp Ser Thr Arg Phe Ser Ser Pro Arg Leu Ser Ala Arg Pro
            275                 280                 285

Ser Arg Lys Arg Thr Leu Ser Ile Ser Pro Leu Ser Asp His Ser Phe
            290                 295                 300

Asp Leu Gln Thr Met Ile Arg Thr Ser Pro Asn Ser Leu Val Thr Ile
305                 310                 315                 320

Leu Asn Asn Ser Arg Ser Ser Ser Ala Ser Gly Ser Tyr Gly His
                325                 330                 335

Leu Ser Ala Ser Ala Ile Ser Pro Ala Leu Ser Phe Thr Tyr Ser Ser
                340                 345                 350

Ala Pro Val Ser Leu His Met His Gln Gln Ile Leu Ser Arg Gln Gln
            355                 360                 365

Ser Leu Gly Ser Ala Phe Gly His Ser Pro Leu Ile His Pro Ala
            370                 375                 380

Pro Thr Phe Pro Thr Gln Arg Pro Ile Pro Gly Ile Pro Thr Val Leu
385                 390                 395                 400

Asn Pro Val Gln Val Ser Ser Gly Pro Ser Glu Ser Ser Gln Asn Lys
                405                 410                 415

Pro Thr Ser Glu Ser Ala Val Ser Ser Thr Gly Asp Pro Met His Asn
                420                 425                 430

Lys Arg Ser Lys Ile Lys Pro Asp Glu Asp Leu Pro Ser Pro Gly Ala
            435                 440                 445
```

```
Arg Gly Gln Gln Glu Gln Pro Glu Gly Thr Thr Leu Val Lys Glu Glu
    450                 455                 460
Gly Asp Lys Asp Glu Ser Lys Gln Glu Pro Glu Val Ile Tyr Glu Thr
465                 470                 475                 480
Asn Cys His Trp Glu Gly Cys Ala Arg Glu Phe Asp Thr Gln Glu Gln
                485                 490                 495
Leu Val His His Ile Asn Asn Asp His Ile His Gly Glu Lys Lys Glu
            500                 505                 510
Phe Val Cys Arg Trp Leu Asp Cys Ser Arg Glu Gln Lys Pro Phe Lys
        515                 520                 525
Ala Gln Tyr Met Leu Val Val His Met Arg Arg His Thr Gly Glu Lys
530                 535                 540
Pro His Lys Cys Thr Phe Glu Gly Cys Thr Lys Ala Tyr Ser Arg Leu
545                 550                 555                 560
Glu Asn Leu Lys Thr His Leu Arg Ser His Thr Gly Glu Lys Pro Tyr
                565                 570                 575
Val Cys Glu His Glu Gly Cys Asn Lys Ala Phe Ser Asn Ala Ser Asp
            580                 585                 590
Arg Ala Lys His Gln Asn Arg Thr His Ser Asn Glu Lys Pro Tyr Val
        595                 600                 605
Cys Lys Ile Pro Gly Cys Thr Lys Arg Tyr Thr Asp Pro Ser Ser Leu
610                 615                 620
Arg Lys His Val Lys Thr Val His Gly Pro Glu Ala His Val Thr Lys
625                 630                 635                 640
Lys Gln Arg Gly Asp Ile His Pro Arg Pro Pro Pro Arg Asp Ser
                645                 650                 655
Gly Ser His Ser Gln Ser Arg Ser Pro Gly Arg Pro Thr Gln Gly Ala
            660                 665                 670
Leu Gly Glu Gln Gln Asp Leu Ser Asn Thr Thr Ser Lys Arg Glu Glu
        675                 680                 685
Cys Leu Gln Val Lys Thr Val Lys Ala Glu Lys Pro Met Thr Ser Gln
690                 695                 700
Pro Ser Pro Gly Gly Gln Ser Ser Cys Ser Ser Gln Gln Ser Pro Ile
705                 710                 715                 720
Ser Asn Tyr Ser Asn Ser Gly Leu Glu Leu Pro Leu Thr Asp Gly Gly
                725                 730                 735
Ser Ile Gly Asp Leu Ser Ala Ile Asp Glu Thr Pro Ile Met Asp Ser
            740                 745                 750
Thr Ile Ser Thr Ala Thr Thr Ala Leu Ala Leu Gln Ala Arg Arg Asn
        755                 760                 765
Pro Ala Gly Thr Lys Trp Met Glu His Val Lys Leu Glu Arg Leu Lys
770                 775                 780
Gln Val Asn Gly Met Phe Pro Arg Leu Asn Pro Ile Leu Pro Pro Lys
785                 790                 795                 800
Ala Pro Ala Val Ser Pro Leu Ile Gly Asn Gly Thr Gln Ser Asn Asn
                805                 810                 815
Thr Cys Ser Leu Gly Gly Pro Met Thr Leu Leu Pro Gly Arg Ser Asp
            820                 825                 830
Leu Ser Gly Val Asp Val Thr Met Leu Asn Met Leu Asn Arg Arg Asp
        835                 840                 845
Ser Ser Ala Ser Thr Ile Ser Ser Ala Tyr Leu Ser Ser Arg Arg Ser
850                 855                 860
Ser Gly Ile Ser Pro Cys Phe Ser Ser Arg Arg Ser Ser Glu Ala Ser
```

```
            865                 870                 875                 880
        Gln Ala Glu Gly Arg Pro Gln Asn Val Ser Val Ala Asp Ser Tyr Asp
                        885                 890                 895
        Pro Ile Ser Thr Asp Ala Ser Arg Arg Ser Ser Glu Ala Ser Gln Ser
                        900                 905                 910
        Asp Gly Leu Pro Ser Leu Leu Ser Leu Thr Pro Ala Gln Gln Tyr Arg
                        915                 920                 925
        Leu Lys Ala Lys Tyr Ala Ala Ala Thr Gly Gly Pro Pro Thr Pro
            930                 935                 940
        Leu Pro Asn Met Glu Arg Met Ser Leu Lys Thr Arg Leu Ala Leu Leu
        945                 950                 955                 960
        Gly Asp Ala Leu Glu Pro Gly Val Ala Leu Pro Val His Ala Pro
                        965                 970                 975
        Arg Arg Cys Ser Asp Gly Gly Ala His Gly Tyr Gly Arg His Leu
                        980                 985                 990
        Gln Pro His Asp Ala Pro Gly His  Gly Val Arg Arg Ala  Ser Asp Pro
                        995                 1000                1005
        Val Arg  Thr Gly Ser Glu Gly  Leu Ala Leu Pro Arg  Val Pro Arg
            1010                1015                1020
        Phe Ser  Ser Leu Ser Ser Cys  Asn Pro Pro Ala Met  Ala Thr Ser
            1025                1030                1035
        Ala Glu  Lys Arg Ser Leu Val  Leu Gln Asn Tyr Thr  Arg Pro Glu
            1040                1045                1050
        Gly Gly  Gln Ser Arg Asn Phe  His Ser Ser Pro Cys  Pro Pro Ser
            1055                1060                1065
        Ile Thr  Glu Asn Val Thr Leu  Glu Ser Leu Thr Met  Asp Ala Asp
            1070                1075                1080
        Ala Asn  Leu Asn Asp Glu Asp  Phe Leu Pro Asp Asp  Val Val Gln
            1085                1090                1095
        Tyr Leu  Asn Ser Gln Asn Gln  Ala Gly Tyr Glu Gln  His Phe Pro
            1100                1105                1110
        Ser Ala  Leu Pro Asp Asp Ser  Lys Val Pro His Gly  Pro Gly Asp
            1115                1120                1125
        Phe Asp  Ala Pro Gly Leu Pro  Asp Ser His Ala Gly  Gln Gln Phe
            1130                1135                1140
        His Ala  Leu Glu Gln Pro Cys  Pro Glu Gly Ser Lys  Thr Asp Leu
            1145                1150                1155
        Pro Ile  Gln Trp Asn Glu Val  Ser Ser Gly Ser Ala  Asp Leu Ser
            1160                1165                1170
        Ser Ser  Lys Leu Lys Cys Gly  Pro Arg Pro Ala Val  Pro Gln Thr
            1175                1180                1185
        Arg Ala  Phe Gly Phe Cys Asn  Gly Met Val Val His  Pro Gln Asn
            1190                1195                1200
        Pro Leu  Arg Ser Gly Pro Ala  Gly Gly Tyr Gln Thr  Leu Gly Glu
            1205                1210                1215
        Asn Ser  Asn Pro Tyr Gly Gly  Pro Glu His Leu Met  Leu His Asn
            1220                1225                1230
        Ser Pro  Gly Ser Gly Thr Ser  Gly Asn Ala Phe His  Glu Gln Pro
            1235                1240                1245
        Cys Lys  Ala Pro Gln Tyr Gly  Asn Cys Leu Asn Arg  Gln Pro Val
            1250                1255                1260
        Ala Pro  Gly Ala Leu Asp Gly  Ala Cys Gly Ala Gly  Ile Gln Ala
            1265                1270                1275
```

| | | | | | | | | | | |
|---|---|---|---|---|---|---|---|---|---|---|
| Ser | Lys | Leu | Lys | Ser | Thr | Pro | Met | Gln | Gly | Ser | Gly | Gly | Gln | Leu |
| | 1280 | | | | 1285 | | | | 1290 | | | | | |
| Asn | Phe | Gly | Leu | Pro | Val | Ala | Pro | Asn | Glu | Ser | Ala | Gly | Ser | Met |
| 1295 | | | | | 1300 | | | | | 1305 | | | | |
| Val | Asn | Gly | Met | Gln | Asn | Gln | Asp | Pro | Val | Gly | Gln | Gly | Tyr | Leu |
| 1310 | | | | | 1315 | | | | | 1320 | | | | |
| Ala | His | Gln | Leu | Leu | Gly | Asp | Ser | Met | Gln | His | Pro | Gly | Ala | Gly |
| 1325 | | | | | 1330 | | | | | 1335 | | | | |
| Arg | Pro | Gly | Gln | Gln | Met | Leu | Gly | Gln | Ile | Ser | Ala | Thr | Ser | His |
| 1340 | | | | | 1345 | | | | | 1350 | | | | |
| Ile | Asn | Ile | Tyr | Gln | Gly | Pro | Glu | Ser | Cys | Leu | Pro | Gly | Ala | His |
| 1355 | | | | | 1360 | | | | | 1365 | | | | |
| Gly | Met | Gly | Ser | Gln | Pro | Ser | Ser | Leu | Ala | Val | Val | Arg | Gly | Tyr |
| 1370 | | | | | 1375 | | | | | 1380 | | | | |
| Gln | Pro | Cys | Ala | Ser | Phe | Gly | Gly | Ser | Arg | Arg | Gln | Ala | Met | Pro |
| 1385 | | | | | 1390 | | | | | 1395 | | | | |
| Arg | Asp | Ser | Leu | Ala | Leu | Gln | Ser | Gly | Gln | Leu | Ser | Asp | Thr | Ser |
| 1400 | | | | | 1405 | | | | | 1410 | | | | |
| Gln | Thr | Cys | Arg | Val | Asn | Gly | Ile | Lys | Met | Glu | Met | Lys | Gly | Gln |
| 1415 | | | | | 1420 | | | | | 1425 | | | | |
| Pro | His | Pro | Leu | Cys | Ser | Asn | Leu | Gln | Asn | Tyr | Ser | Gly | Gln | Phe |
| 1430 | | | | | 1435 | | | | | 1440 | | | | |
| Tyr | Asp | Gln | Thr | Val | Gly | Phe | Ser | Gln | Gln | Asp | Thr | Lys | Ala | Gly |
| 1445 | | | | | 1450 | | | | | 1455 | | | | |
| Ser | Phe | Ser | Ile | Ser | Asp | Ala | Ser | Cys | Leu | Leu | Gln | Gly | Thr | Ser |
| 1460 | | | | | 1465 | | | | | 1470 | | | | |
| Ala | Lys | Asn | Ser | Glu | Leu | Leu | Ser | Pro | Gly | Ala | Asn | Gln | Val | Thr |
| 1475 | | | | | 1480 | | | | | 1485 | | | | |
| Ser | Thr | Val | Asp | Ser | Leu | Asp | Ser | His | Asp | Leu | Glu | Gly | Val | Gln |
| 1490 | | | | | 1495 | | | | | 1500 | | | | |
| Ile | Asp | Phe | Asp | Ala | Ile | Ile | Asp | Gly | Asp | His | Ser | Ser | Leu |
| 1505 | | | | | 1510 | | | | | 1515 | | | | |
| Met | Ser | Gly | Ala | Leu | Ser | Pro | Ser | Ile | Ile | Gln | Asn | Leu | Ser | His |
| 1520 | | | | | 1525 | | | | | 1530 | | | | |
| Ser | Ser | Ser | Arg | Leu | Thr | Thr | Pro | Arg | Ala | Ser | Leu | Pro | Phe | Pro |
| 1535 | | | | | 1540 | | | | | 1545 | | | | |
| Ala | Leu | Ser | Met | Ser | Thr | Thr | Asn | Met | Ala | Ile | Gly | Asp | Met | Ser |
| 1550 | | | | | 1555 | | | | | 1560 | | | | |
| Ser | Leu | Leu | Thr | Ser | Leu | Ala | Glu | Glu | Ser | Lys | Phe | Leu | Ala | Val |
| 1565 | | | | | 1570 | | | | | 1575 | | | | |
| Met | Gln |
| 1580 | |

<210> SEQ ID NO 13
<211> LENGTH: 1389
<212> TYPE: DNA
<213> ORGANISM: Homo sapiens

<400> SEQUENCE: 13

```
atgctgctgc tggcgagatg tctgctgcta gtcctcgtct cctcgctgct ggtatgctcg     60
ggactggcgt gcggaccggg caggggttc gggaagagga ggcacccaa aaagctgacc      120 cctttagcct acaagcagtt tatccccaat gtggccgaga gaccctagg cgccagcgga     180 aggtatgaag ggaagatctc cagaaactcc gagcgattta ggaactcac ccccaattac     240
```

```
aaccccgaca tcatatttaa ggatgaagaa aacaccggag cggacaggct gatgactcag    300
aggtgtaagg acaagttgaa cgctttggcc atctcggtga tgaaccagtg gccaggagtg    360
aaactgcggg tgaccgaggg ctgggacgaa gatggccacc actcagagga gtctctgcac    420
tacgagggcc gcgcagtgga catcaccacg tctgaccgcg accgcagcaa gtacggcatg    480
ctggcccgcc tggcggtgga ggccggcttc gactgggtgt actacgagtc caaggcacat    540
atccactgct cggtgaaagc agagaactcg gtggcggcca atcggggagg ctgcttcccg    600
ggctcggcca cggtgcacct ggagcagggc ggcaccaagc tggtgaagga cctgagcccc    660
ggggaccgcg tgctggcggc ggacgaccag ggccggctgc tctacagcga cttcctcact    720
ttcctggacc gcgacgacgg cgccaagaag gtcttctacg tgatcgagac gcgggagccg    780
cgcgagcgcg tgctgctcac cgccgcgcac ctgctctttg tggcgccgca caacgactcg    840
gccaccgggg agcccgaggc gtcctcgggc tcggggccgc cttccggggg cgcactgggg    900
cctcgggcgc tgttcgccag ccgcgtgcgc cgggccagc gcgtgtacgt ggtggccgag    960
cgtgacgggg accgccggct cctgcccgcc gctgtgcaca gcgtgaccct aagcgaggag    1020
gccgcgggcg cctacgcgcc gctcacggcc cagggcacca ttctcatcaa ccgggtgctg    1080
gcctcgtgct acgcggtcat cgaggagcac agctgggcgc accgggcctt cgcgcccttc    1140
cgcctggcgc acgcgctcct ggctgcactg gcgcccgcgc gcacggaccg cggcggggac    1200
agcggcggcg gggaccgcgg gggcggcggc ggcagagtag ccctaaccgc tccaggtgct    1260
gccgacgctc cgggtgcggg ggccaccgcg ggcatccact ggtactcgca gctgctctac    1320
caaataggca cctggctcct ggacagcgag gccctgcacc cgctgggcat ggcggtcaag    1380
tccagctga                                                          1389
```

<210> SEQ ID NO 14
<211> LENGTH: 462
<212> TYPE: PRT
<213> ORGANISM: Homo sapiens

<400> SEQUENCE: 14

```
Met Leu Leu Leu Ala Arg Cys Leu Leu Val Leu Val Ser Ser Leu
1               5                   10                  15

Leu Val Cys Ser Gly Leu Ala Cys Gly Pro Gly Arg Gly Phe Gly Lys
                20                  25                  30

Arg Arg His Pro Lys Lys Leu Thr Pro Leu Ala Tyr Lys Gln Phe Ile
            35                  40                  45

Pro Asn Val Ala Glu Lys Thr Leu Gly Ala Ser Gly Arg Tyr Glu Gly
        50                  55                  60

Lys Ile Ser Arg Asn Ser Glu Arg Phe Lys Glu Leu Thr Pro Asn Tyr
65                  70                  75                  80

Asn Pro Asp Ile Ile Phe Lys Asp Glu Glu Asn Thr Gly Ala Asp Arg
                85                  90                  95

Leu Met Thr Gln Arg Cys Lys Asp Lys Leu Asn Ala Leu Ala Ile Ser
            100                 105                 110

Val Met Asn Gln Trp Pro Gly Val Lys Leu Arg Val Thr Glu Gly Trp
        115                 120                 125

Asp Glu Asp Gly His His Ser Glu Glu Ser Leu His Tyr Glu Gly Arg
    130                 135                 140

Ala Val Asp Ile Thr Thr Ser Asp Arg Asp Arg Ser Lys Tyr Gly Met
145                 150                 155                 160
```

```
Leu Ala Arg Leu Ala Val Glu Ala Gly Phe Asp Trp Val Tyr Tyr Glu
            165                 170                 175
Ser Lys Ala His Ile His Cys Ser Val Lys Ala Glu Asn Ser Val Ala
        180                 185                 190
Ala Lys Ser Gly Gly Cys Phe Pro Gly Ser Ala Thr Val His Leu Glu
    195                 200                 205
Gln Gly Gly Thr Lys Leu Val Lys Asp Leu Ser Pro Gly Asp Arg Val
210                 215                 220
Leu Ala Ala Asp Asp Gln Gly Arg Leu Leu Tyr Ser Asp Phe Leu Thr
225                 230                 235                 240
Phe Leu Asp Arg Asp Asp Gly Ala Lys Lys Val Phe Tyr Val Ile Glu
            245                 250                 255
Thr Arg Glu Pro Arg Glu Arg Leu Leu Leu Thr Ala Ala His Leu Leu
        260                 265                 270
Phe Val Ala Pro His Asn Asp Ser Ala Thr Gly Glu Pro Glu Ala Ser
    275                 280                 285
Ser Gly Ser Gly Pro Pro Ser Gly Gly Ala Leu Gly Pro Arg Ala Leu
290                 295                 300
Phe Ala Ser Arg Val Arg Pro Gly Gln Arg Val Tyr Val Val Ala Glu
305                 310                 315                 320
Arg Asp Gly Asp Arg Arg Leu Leu Pro Ala Ala Val His Ser Val Thr
            325                 330                 335
Leu Ser Glu Glu Ala Ala Gly Ala Tyr Ala Pro Leu Thr Ala Gln Gly
        340                 345                 350
Thr Ile Leu Ile Asn Arg Val Leu Ala Ser Cys Tyr Ala Val Ile Glu
    355                 360                 365
Glu His Ser Trp Ala His Arg Ala Phe Ala Pro Phe Arg Leu Ala His
370                 375                 380
Ala Leu Leu Ala Ala Leu Ala Pro Ala Arg Thr Asp Arg Gly Gly Asp
385                 390                 395                 400
Ser Gly Gly Gly Asp Arg Gly Gly Gly Arg Val Ala Leu Thr
            405                 410                 415
Ala Pro Gly Ala Ala Asp Ala Pro Gly Ala Gly Ala Thr Ala Gly Ile
        420                 425                 430
His Trp Tyr Ser Gln Leu Leu Tyr Gln Ile Gly Thr Trp Leu Leu Asp
    435                 440                 445
Ser Glu Ala Leu His Pro Leu Gly Met Ala Val Lys Ser Ser
450                 455                 460

<210> SEQ ID NO 15
<211> LENGTH: 1236
<212> TYPE: DNA
<213> ORGANISM: Homo sapiens

<400> SEQUENCE: 15
atgtctcccg cccggctccg gccccgactg cacttctgcc tggtcctgtt gctgctgctg      60
gtggtgccgg cggcatgggg ctgcgggccg ggtcgggtgg tgggcagccg ccggcgaccg     120
ccacgcaaac tcgtgccgct cgcctacaag cagttcagcc ccaatgtgcc cgagaagacc     180
ctgggcgcca cgcgacgcta tgaaggcaag atcgctcgca gctccgagcg cttcaaggag     240
ctcaccccca attacaatcc agacatcatc ttcaaggacg aggagaacac aggcgccgac     300
cgcctcatga cccagcgctg caaggaccgc tgaactcgc tggctatctc ggtgatgaac     360
cagtggcccg gtgtgaagct gcgggtgacc gagggctggg acgaggacgg ccaccactca     420
```

```
gaggagtccc tgcattatga gggccgcgcg gtggacatca ccacatcaga ccgcgaccgc    480
aataagtatg gactgctggc gcgcttggca gtggaggccg gctttgactg ggtgtattac    540
gagtcaaagg cccacgtgca ttgctccgtc aagtccgagc actcggccgc agccaagacg    600
ggcggctgct tccctgccgg agcccaggta cgcctggaga gtggggcgcg tgtggccttg    660
tcagccgtga ggccgggaga ccgtgtgctg gccatggggg aggatgggag ccccaccttc    720
agcgatgtgc tcattttcct ggaccgcgag cctcacaggc tgagagcctt ccaggtcatc    780
gagactcagg acccccacg ccgcctggca ctcacacccg ctcacctgct ctttacggct     840
gacaatcaca cggagccggc agcccgcttc cgggccacat ttgccagcca cgtgcagcct    900
ggccagtacg tgctggtggc tggggtgcca ggcctgcagc ctgcccgcgt ggcagctgtc    960
tctacacacg tggccctcgg ggcctacgcc ccgctcacaa gcatgggac actggtggtg     1020
gaggatgtgg tggcatcctg cttcgcggcc gtggctgacc accacctggc tcagttggcc    1080
ttctggcccc tgagactctt tcacagcttg catggggca gctggacccc gggggagggt     1140
gtgcattggt accccagct gctctaccgc ctggggcgtc tcctgctaga agagggcagc     1200
ttccacccac tgggcatgtc cggggcaggg agctga                              1236
```

<210> SEQ ID NO 16
<211> LENGTH: 411
<212> TYPE: PRT
<213> ORGANISM: Homo sapiens

<400> SEQUENCE: 16

```
Met Ser Pro Ala Arg Leu Arg Pro Arg Leu His Phe Cys Leu Val Leu
1               5                   10                  15

Leu Leu Leu Val Val Pro Ala Ala Trp Gly Cys Gly Pro Gly Arg
            20                  25                  30

Val Val Gly Ser Arg Arg Arg Pro Pro Arg Lys Leu Val Pro Leu Ala
        35                  40                  45

Tyr Lys Gln Phe Ser Pro Asn Val Pro Glu Lys Thr Leu Gly Ala Ser
    50                  55                  60

Gly Arg Tyr Glu Gly Lys Ile Ala Arg Ser Ser Glu Arg Phe Lys Glu
65                  70                  75                  80

Leu Thr Pro Asn Tyr Asn Pro Asp Ile Ile Phe Lys Asp Glu Glu Asn
                85                  90                  95

Thr Gly Ala Asp Arg Leu Met Thr Gln Arg Cys Lys Asp Arg Leu Asn
            100                 105                 110

Ser Leu Ala Ile Ser Val Met Asn Gln Trp Pro Gly Val Lys Leu Arg
        115                 120                 125

Val Thr Glu Gly Trp Asp Glu Asp Gly His His Ser Glu Glu Ser Leu
    130                 135                 140

His Tyr Glu Gly Arg Ala Val Asp Ile Thr Thr Ser Asp Arg Asp Arg
145                 150                 155                 160

Asn Lys Tyr Gly Leu Leu Ala Arg Leu Ala Val Glu Ala Gly Phe Asp
                165                 170                 175

Trp Val Tyr Tyr Glu Ser Lys Ala His Val His Cys Ser Val Lys Ser
            180                 185                 190

Glu His Ser Ala Ala Ala Lys Thr Gly Gly Cys Phe Pro Ala Gly Ala
        195                 200                 205

Gln Val Arg Leu Glu Ser Gly Ala Arg Val Ala Leu Ser Ala Val Arg
    210                 215                 220

Pro Gly Asp Arg Val Leu Ala Met Gly Glu Asp Gly Ser Pro Thr Phe
```

```
                  225                 230                 235                 240

Ser Asp Val Leu Ile Phe Leu Asp Arg Glu Pro His Arg Leu Arg Ala
                            245                 250                 255

Phe Gln Val Ile Glu Thr Gln Asp Pro Pro Arg Arg Leu Ala Leu Thr
                            260                 265                 270

Pro Ala His Leu Leu Phe Thr Ala Asp Asn His Thr Glu Pro Ala Ala
                            275                 280                 285

Arg Phe Arg Ala Thr Phe Ala Ser His Val Gln Pro Gly Gln Tyr Val
                            290                 295                 300

Leu Val Ala Gly Val Pro Gly Leu Gln Pro Ala Arg Val Ala Ala Val
        305                 310                 315                 320

Ser Thr His Val Ala Leu Gly Ala Tyr Ala Pro Leu Thr Lys His Gly
                            325                 330                 335

Thr Leu Val Val Glu Asp Val Val Ala Ser Cys Phe Ala Ala Val Ala
                            340                 345                 350

Asp His His Leu Ala Gln Leu Ala Phe Trp Pro Leu Arg Leu Phe His
                            355                 360                 365

Ser Leu Ala Trp Gly Ser Trp Thr Pro Gly Glu Gly Val His Trp Tyr
                            370                 375                 380

Pro Gln Leu Leu Tyr Arg Leu Gly Arg Leu Leu Glu Glu Gly Ser
        385                 390                 395                 400

Phe His Pro Leu Gly Met Ser Gly Ala Gly Ser
                            405                 410

<210> SEQ ID NO 17
<211> LENGTH: 1191
<212> TYPE: DNA
<213> ORGANISM: Homo sapiens

<400> SEQUENCE: 17
atggctctcc tgaccaatct actgcccctg tgctgcttgg cacttctggc gctgccagcc      60
cagagctgcg ggccgggccg ggggccggtt ggccggcgcc gctatgcgcg caagcagctc     120
gtgccgctac tctacaagca atttgtgccc ggcgtgccag agcggaccct gggcgccagt     180
gggccagcgg aggggagggt ggcaaggggc tccgagcgct ccggaccct cgtgcccaac      240 tacaaccccg acatcatctt caaggatgag gagaacagtg gagccgaccg cctgatgacc     300
gagcgttgta aggagcgggt gaacgctttg gccattgccg tgatgaacat gtggcccgga     360
gtgcgcctac gagtgactga gggctgggac gaggacggcc accacgctca ggattcactc     420
cactacgaag gccgtgcttt ggacatcact acgtctgacc gcgaccgcaa caagtatggg     480
ttgctggcgc gcctcgcagt ggaagccggc ttcgactggg tctactacga gtcccgcaac     540
cacgtccacg tgtcggtcaa agctgataac tcactggcgg tccgggcggg cggctgcttt     600
ccgggaaatg caactgtgcg cctgtggagc ggcgagcgga agggctgcgg gaactgcac       660 cgcggagact gggttttggc ggccgatgcg tcaggccggg tggtgcccac gccggtgctg     720
ctcttcctgg accgggactt gcagcgccgg gcttcatttg tggctgtgga gaccgagtgg     780
cctccacgca aactgttgct cacgccctgg cacctggtgt tgccgctcg agggccggcg      840 cccgcgccag cgactttgc accggtgttc gcgcgccggc tacgcgctgg ggactcggtg     900
ctggcgcccg cggggatgc gcttcggcca gcgcgcgtgg cccgtgtggc gcgggaggaa     960
gccgtggggc tgttcgcgcc gctcaccgcg cacgggacgc tgctggtgaa cgatgtcctg    1020
gcctcttgct acgcggttct ggagagtcac cagtgggcgc accgcgcttt tgccccttg     1080
```

```
agactgctgc acgcgctagg ggcgctgctc cccggcgggg ccgtccagcc gactggcatg    1140
cattggtact ctcggctcct ctaccgctta gcggaggagc tactgggctg a             1191
```

<210> SEQ ID NO 18
<211> LENGTH: 396
<212> TYPE: PRT
<213> ORGANISM: Homo sapiens

<400> SEQUENCE: 18

```
Met Ala Leu Leu Thr Asn Leu Leu Pro Leu Cys Cys Leu Ala Leu Leu
1               5                   10                  15

Ala Leu Pro Ala Gln Ser Cys Gly Pro Gly Arg Gly Pro Val Gly Arg
            20                  25                  30

Arg Arg Tyr Ala Arg Lys Gln Leu Val Pro Leu Leu Tyr Lys Gln Phe
        35                  40                  45

Val Pro Gly Val Pro Glu Arg Thr Leu Gly Ala Ser Gly Pro Ala Glu
    50                  55                  60

Gly Arg Val Ala Arg Gly Ser Glu Arg Phe Arg Asp Leu Val Pro Asn
65                  70                  75                  80

Tyr Asn Pro Asp Ile Ile Phe Lys Asp Glu Glu Asn Ser Gly Ala Asp
                85                  90                  95

Arg Leu Met Thr Glu Arg Cys Lys Glu Arg Val Asn Ala Leu Ala Ile
            100                 105                 110

Ala Val Met Asn Met Trp Pro Gly Val Arg Leu Arg Val Thr Glu Gly
        115                 120                 125

Trp Asp Glu Asp Gly His His Ala Gln Asp Ser Leu His Tyr Glu Gly
130                 135                 140

Arg Ala Leu Asp Ile Thr Thr Ser Asp Arg Asp Arg Asn Lys Tyr Gly
145                 150                 155                 160

Leu Leu Ala Arg Leu Ala Val Glu Ala Gly Phe Asp Trp Val Tyr Tyr
                165                 170                 175

Glu Ser Arg Asn His Val His Val Ser Val Lys Ala Asp Asn Ser Leu
            180                 185                 190

Ala Val Arg Ala Gly Gly Cys Phe Pro Gly Asn Ala Thr Val Arg Leu
        195                 200                 205

Trp Ser Gly Glu Arg Lys Gly Leu Arg Glu Leu His Arg Gly Asp Trp
210                 215                 220

Val Leu Ala Ala Asp Ala Ser Gly Arg Val Val Pro Thr Pro Val Leu
225                 230                 235                 240

Leu Phe Leu Asp Arg Asp Leu Gln Arg Ala Ser Phe Val Ala Val
                245                 250                 255

Glu Thr Glu Trp Pro Pro Arg Lys Leu Leu Leu Thr Pro Trp His Leu
            260                 265                 270

Val Phe Ala Ala Arg Gly Pro Ala Pro Ala Pro Gly Asp Phe Ala Pro
        275                 280                 285

Val Phe Ala Arg Arg Leu Arg Ala Gly Asp Ser Val Leu Ala Pro Gly
        290                 295                 300

Gly Asp Ala Leu Arg Pro Ala Arg Val Ala Arg Val Ala Arg Glu Glu
305                 310                 315                 320

Ala Val Gly Val Phe Ala Pro Leu Thr Ala His Gly Thr Leu Leu Val
                325                 330                 335

Asn Asp Val Leu Ala Ser Cys Tyr Ala Val Leu Glu Ser His Gln Trp
            340                 345                 350

Ala His Arg Ala Phe Ala Pro Leu Arg Leu Leu His Ala Leu Gly Ala
```

```
                355                 360                 365
Leu Leu Pro Gly Gly Ala Val Gln Pro Thr Gly Met His Trp Tyr Ser
        370                 375                 380
Arg Leu Leu Tyr Arg Leu Ala Glu Glu Leu Leu Gly
385                 390                 395

<210> SEQ ID NO 19
<211> LENGTH: 2103
<212> TYPE: DNA
<213> ORGANISM: Homo sapiens

<400> SEQUENCE: 19
atgctgaaga tgctctcctt taagctgctg ctgctggccg tggctctggg cttctttgaa      60
ggagatgcta agtttgggga agaaacgaa gggagcggag caaggaggag aaggtgcctg      120
aatgggaacc ccccgaagcg cctgaaaagg agagacagga ggatgatgtc ccagctggag      180
ctgctgagtg ggggagagat gctgtgcggt ggcttctacc ctcggctgtc ctgctgcctg      240
cggagtgaca gcccggggct agggcgcctg agaaataaga tattttctgt taccaacaac      300
acagaatgtg ggaagttact ggaggaaatc aaatgtgcac tttgctctcc acattctcaa      360
agcctgttcc actcacctga gagaagtc ttggaaagag acctagtact tcctctgctc      420
tgcaaagact attgcaaaga attcttttac acttgccgag ccatattcc aggtttcctt      480
caaacaactg cggatgagtt tgcttttac tatgcaagaa aagatggtgg ttgtgcttt      540
ccagattttc caagaaaaca agtcagagga ccagcatcta actacttgga ccagatggaa      600
gaatatgaca agtggaaga gatcagcaga aagcacaaac acaactgctt ctgtattcag      660
gaggttgtga gtgggctgcg gcagcccgtt ggtgccctgc atagtgggga tggctcgcaa      720
cgtctcttca ttctggaaaa agaaggttat gtgaagatac ttacccctga aggagaaatt      780
ttcaaggagc cttatttgga cattcacaaa cttgttcaaa gtggaataaa gggaggagat      840
gaaagaggac tgctaagcct cgcattccat cccaattaca agaaaaatgg aaagttgtat      900
gtgtcctata ccaccaacca gaacggtgg gctatcgggc tcatgaccac cattcttagg      960
gttgtggaat acacagtatc cagaaaaat ccacaccaag ttgatttgag aacagccaga      1020
gtctttcttg aagttgcaga actccacaga aagcatctgg aggacaact gctctttggc      1080
cctgacggct ttttgtacat cattcttggt gatgggatga ttacactgga tgatatggaa      1140
gaaatggatg ggttaagtga tttcacaggc tcagtgctac ggctggatgt ggacacagac      1200
atgtgcaacg tgccttattc cataccaagg agcaacccac acttcaacag caccaaccag      1260
ccccccgaag tgtttgctca tgggctccac gatccaggca gatgtgctgt ggatagacat      1320
cccactgata taaacatcaa tttaacgata ctgtgttcag actccaatgg aaaaaacaga      1380
tcatcagcca gaattctaca gataataaag gggaaagatt atgaaagtga gccatcactt      1440
ttagaattca gccattcag taatggtcct ttggttggtg gatttgtata ccggggctgc      1500
cagtcagaaa gattgtatgg aagctacgtg tttggagatc gtaatgggaa tttcctaact      1560
ctccagcaaa gtcctgtgac aaagcagtgg caagaaaaac cactctgtct cggcactagt      1620
gggtcctgta gaggctactt ttccggtcac atcttggat ttggagaaga tgaactaggt      1680
gaagtttaca ttttatcaag cagtaaaagt atgacccaga ctcacaatgg aaaactctac      1740
aaaattgtag atcccaaaag acctttaatg cctgaggaat gcagagccac ggtacaacct      1800
gcacagacac tgacttcaga gtgctccagg ctctgtcgaa acggctactg cacccccacg      1860
ggaaagtgct gctgcagtcc aggctgggag ggggacttct gcagaactgc aaaatgtgag      1920
```

```
ccagcatgtc gtcatggagg tgtctgtgtt agaccgaaca agtgcctctg taaaaaagga   1980
tatcttggtc ctcaatgtga acaagtggac agaaacatcc gcagagtgac cagggcaggt   2040
attcttgatc agatcattga catgacatct tacttgctgg atctaacaag ttacattgta   2100
tag                                                                  2103

<210> SEQ ID NO 20
<211> LENGTH: 700
<212> TYPE: PRT
<213> ORGANISM: Homo sapiens

<400> SEQUENCE: 20

Met Leu Lys Met Leu Ser Phe Lys Leu Leu Leu Ala Val Ala Leu
1               5                   10                  15

Gly Phe Phe Glu Gly Asp Ala Lys Phe Gly Glu Arg Asn Glu Gly Ser
            20                  25                  30

Gly Ala Arg Arg Arg Cys Leu Asn Gly Asn Pro Pro Lys Arg Leu
        35                  40                  45

Lys Arg Arg Asp Arg Arg Met Met Ser Gln Leu Glu Leu Leu Ser Gly
    50                  55                  60

Gly Glu Met Leu Cys Gly Gly Phe Tyr Pro Arg Leu Ser Cys Cys Leu
65                  70                  75                  80

Arg Ser Asp Ser Pro Gly Leu Gly Arg Leu Glu Asn Lys Ile Phe Ser
                85                  90                  95

Val Thr Asn Asn Thr Glu Cys Gly Lys Leu Leu Glu Glu Ile Lys Cys
            100                 105                 110

Ala Leu Cys Ser Pro His Ser Gln Ser Leu Phe His Ser Pro Glu Arg
        115                 120                 125

Glu Val Leu Glu Arg Asp Leu Val Leu Pro Leu Leu Cys Lys Asp Tyr
    130                 135                 140

Cys Lys Glu Phe Phe Tyr Thr Cys Arg Gly His Ile Pro Gly Phe Leu
145                 150                 155                 160

Gln Thr Thr Ala Asp Glu Phe Cys Phe Tyr Tyr Ala Arg Lys Asp Gly
                165                 170                 175

Gly Leu Cys Phe Pro Asp Phe Pro Arg Lys Gln Val Arg Gly Pro Ala
            180                 185                 190

Ser Asn Tyr Leu Asp Gln Met Glu Glu Tyr Asp Lys Val Glu Glu Ile
        195                 200                 205

Ser Arg Lys His Lys His Asn Cys Phe Cys Ile Gln Glu Val Val Ser
    210                 215                 220

Gly Leu Arg Gln Pro Val Gly Ala Leu His Ser Gly Asp Gly Ser Gln
225                 230                 235                 240

Arg Leu Phe Ile Leu Glu Lys Glu Gly Tyr Val Lys Ile Leu Thr Pro
                245                 250                 255

Glu Gly Glu Ile Phe Lys Glu Pro Tyr Leu Asp Ile His Lys Leu Val
            260                 265                 270

Gln Ser Gly Ile Lys Gly Gly Asp Glu Arg Gly Leu Leu Ser Leu Ala
        275                 280                 285

Phe His Pro Asn Tyr Lys Lys Asn Gly Lys Leu Tyr Val Ser Tyr Thr
    290                 295                 300

Thr Asn Gln Glu Arg Trp Ala Ile Gly Pro His Asp His Ile Leu Arg
305                 310                 315                 320

Val Val Glu Tyr Thr Val Ser Arg Lys Asn Pro His Gln Val Asp Leu
                325                 330                 335
```

Arg Thr Ala Arg Val Phe Leu Glu Val Ala Glu Leu His Arg Lys His
                340                 345                 350

Leu Gly Gly Gln Leu Leu Phe Gly Pro Asp Gly Phe Leu Tyr Ile Ile
                355                 360                 365

Leu Gly Asp Gly Met Ile Thr Leu Asp Asp Met Glu Glu Met Asp Gly
            370                 375                 380

Leu Ser Asp Phe Thr Gly Ser Val Leu Arg Leu Asp Val Asp Thr Asp
385                 390                 395                 400

Met Cys Asn Val Pro Tyr Ser Ile Pro Arg Ser Asn Pro His Phe Asn
                405                 410                 415

Ser Thr Asn Gln Pro Pro Glu Val Phe Ala His Gly Leu His Asp Pro
                420                 425                 430

Gly Arg Cys Ala Val Asp Arg His Pro Thr Asp Ile Asn Ile Asn Leu
            435                 440                 445

Thr Ile Leu Cys Ser Asp Ser Asn Gly Lys Asn Arg Ser Ser Ala Arg
450                 455                 460

Ile Leu Gln Ile Ile Lys Gly Lys Asp Tyr Glu Ser Glu Pro Ser Leu
465                 470                 475                 480

Leu Glu Phe Lys Pro Phe Ser Asn Gly Pro Leu Val Gly Gly Phe Val
                485                 490                 495

Tyr Arg Gly Cys Gln Ser Glu Arg Leu Tyr Gly Ser Tyr Val Phe Gly
            500                 505                 510

Asp Arg Asn Gly Asn Phe Leu Thr Leu Gln Gln Ser Pro Val Thr Lys
            515                 520                 525

Gln Trp Gln Glu Lys Pro Leu Cys Leu Gly Thr Ser Gly Ser Cys Arg
            530                 535                 540

Gly Tyr Phe Ser Gly His Ile Leu Gly Phe Gly Glu Asp Glu Leu Gly
545                 550                 555                 560

Glu Val Tyr Ile Leu Ser Ser Lys Ser Met Thr Gln Thr His Asn
                565                 570                 575

Gly Lys Leu Tyr Lys Ile Val Asp Pro Lys Arg Pro Leu Met Pro Glu
            580                 585                 590

Glu Cys Arg Ala Thr Val Gln Pro Ala Gln Thr Leu Thr Ser Glu Cys
            595                 600                 605

Ser Arg Leu Cys Arg Asn Gly Tyr Cys Thr Pro Thr Gly Lys Cys Cys
            610                 615                 620

Cys Ser Pro Gly Trp Glu Gly Asp Phe Cys Arg Thr Ala Lys Cys Glu
625                 630                 635                 640

Pro Ala Cys Arg His Gly Gly Val Cys Val Arg Pro Asn Lys Cys Leu
            645                 650                 655

Cys Lys Lys Gly Tyr Leu Gly Pro Gln Cys Glu Gln Val Asp Arg Asn
            660                 665                 670

Ile Arg Arg Val Thr Arg Ala Gly Ile Leu Asp Gln Ile Ile Asp Met
            675                 680                 685

Thr Ser Tyr Leu Leu Asp Leu Thr Ser Tyr Ile Val
            690                 695                 700

<210> SEQ ID NO 21
<211> LENGTH: 4145
<212> TYPE: DNA
<213> ORGANISM: Homo sapiens

<400> SEQUENCE: 21
tggggaaggc tactggccgg aaagcgccgc tgtggctgag agcgaagttt cagagactct    60

```
tatttaaact gggttgttac attcaaaaaa actgcggcaa gttcttggtt gtgggcctcc    120
tcatatttgg ggccttcgcg gtgggattaa aagcagcgaa cctcgagacc aacgtggagg    180
agctgtgggt ggaagttgga ggacgagtaa gtcgtgaatt aaattatact cgccagaaga    240
ttggagaaga ggctatgttt aatcctcaac tcatgataca gaccctaaa gaagaaggtg     300
ctaatgtcct gaccacagaa gcgctcctac aacacctgga ctcggcactc caggccagcc    360
gtgtccatgt atacatgtac aacaggcagt ggaaattgga acatttgtgt tacaaatcag    420
gagagcttat cacagaaaca ggttacatgg atcagataat agaatatctt tacccttgtt    480
tgattattac acctttggac tgcttctggg aaggggcgaa attacagtct gggacagcat    540
acctcctagg taaacctcct ttgcggtgga caaacttcga ccctttggaa ttcctggaag    600
agttaaagaa aataaactat caagtggaca gctgggagga aatgctgaat aaggctgagg    660
ttggtcatgg ttacatggac cgcccctgcc tcaatccggc cgatccagac tgccccgcca    720
cagcccccaa caaaaattca accaaacctc ttgatatggc ccttgttttg aatggtggat    780
gtcatggctt atccagaaag tatatgcact ggcaggagga gttgattgtg ggtggcacag    840
tcaagaacag cactggaaaa ctcgtcagcg cccatgccct gcagaccatg ttccagttaa    900
tgactcccaa gcaaatgtac gagcacttca aggggtacga gtatgtctca cacatcaact    960
ggaacgagga caaagcggca gccatcctgg aggcctggca gaggacatat gtggaggtgg   1020
ttcatcagag tgtcgcacag aactccactc aaaaggtgct ttccttcacc accacgaccc   1080
tggacgacat cctgaaatcc ttctctgacg tcagtgtcat ccgcgtggcc agcggctact   1140
tactcatgct cgcctatgcc tgtctaacca tgctgcgctg ggactgctcc aagtcccagg   1200
gtgccgtggg gctggctggc gtcctgctgg ttgcactgtc agtggctgca ggactgggcc   1260
tgtgctcatt gatcggaatt tcctttaacg ctgcaacaac tcaggttttg ccatttctcg   1320
ctcttggtgt tggtgtggat gatgttttc ttctggccca cgccttcagt gaaacaggac   1380
agaataaaag aatccctttt gaggacagga ccggggagtg cctgaagcgc acaggagcca   1440
gcgtggccct cacgtccatc agcaatgtca cagccttctt catggccgcg ttaatcccaa   1500
ttcccgctct gcgggcgttc tccctccagg cagcggtagt agtggtgttc aattttgcca   1560
tggttctgct catttttcct gcaattctca gcatggattt atatcgacgc gaggacagga   1620
gactggatat tttctgctgt tttacaagcc cctgcgtcag cagagtgatt caggttgaac   1680
ctcaggccta caccgacaca cacgacaata cccgctacag ccccccacct ccctacagca   1740
gccacagctt tgcccatgaa acgcagatta ccatgcagtc cactgtccag ctccgcacgg   1800
agtacgaccc ccacacgcac gtgtactaca ccaccgctga gccgcgctcc gagatctctg   1860
tgcagcccgt caccgtgaca caggacaccc tcagctgcca gagcccagag agcaccagct   1920
ccacaaggga cctgctctcc cagttctccg actccagcct ccactgcctc gagcccccct   1980
gtacgaagtg gacactctca tcttttgctg agaagcacta tgctcctttc ctcttgaaac   2040
caaaagccaa ggtagtggtg atcttccttt ttctgggctt gctgggggtc agcctttatg   2100
gcaccacccg agtgagagac gggctggacc ttacggacat tgtacctcgg gaaaccagag   2160
aatatgactt tattgctgca caattcaaat acttttcttt ctacaacatg tatatagtca   2220
cccagaaagc agactacccg aatatccagc acttacttta cgacctacac aggagtttca   2280
gtaacgtgaa gtatgtcatg ttggaagaaa acaaacagct tcccaaaatg tggctgcact   2340
acttcagaga ctggcttcag ggacttcagg atgcatttga cagtgactgg gaaaccggga   2400
```

-continued

| | |
|---|---|
| aaatcatgcc aaacaattac aagaatggat cagacgatgg agtccttgcc tacaaactcc | 2460 |
| tggtgcaaac cggcagccgc gataagccca tcgacatcag ccagttgact aaacagcgtc | 2520 |
| tggtggatgc agatggcatc attaatccca gcgctttcta catctacctg acggcttggg | 2580 |
| tcagcaacga ccccgtcgcg tatgctgcct cccaggccaa catccggcca caccgaccag | 2640 |
| aatgggtcca cgacaaagcc gactacatgc tgaaacaag gctgagaatc ccggcagcag | 2700 |
| agcccatcga gtatgcccag ttcccttcct acctcaacgg cttgcgggac acctcagact | 2760 |
| tgtggaggc aattgaaaaa gtaaggacca tctgcagcaa ctatacgagc tggggctgt | 2820 |
| ccagttaccc caacggctac cccttcctct tctgggagca gtacatcggc ctccgccact | 2880 |
| ggctgctgct gttcatcagc gtggtgttgg cctgcacatt cctcgtgtgc gctgtcttcc | 2940 |
| ttctgaaccc ctggacggcc gggatcattg tgatggtcct ggcgctgatg acggtcgagc | 3000 |
| tgttcggcat gatgggcctc atcggaatca agctcagtgc cgtgcccgtg gtcatcctga | 3060 |
| tcgcttctgt tggcatagga gtggagttca ccgttcacgt tgctttggcc tttctgacgg | 3120 |
| ccatcggcga caagaaccgc agggctgtgc ttgccctgga gcacatgttt gcaccccgtcc | 3180 |
| tggatgcgc cgtgtccact ctgctgggag tgctgatgct ggcgggatct gagttcgact | 3240 |
| tcattgtcag gtatttcttt gctgtgctgg cgatcctcac catcctcggc gttctcaatg | 3300 |
| ggctggtttt gcttcccgtg ctttttgtctt tctttggacc atatcctgag gtgtctccag | 3360 |
| ccaacggctt gaaccgcctg cccacaccct cccctgagcc accccccagc gtggtccgct | 3420 |
| tcgccatgcc gcccggccac acgcacagcg ggtctgattc ctccgactcg gagtatagtt | 3480 |
| cccagacgac agtgtcaggc ctcagcgagg agcttcggca ctacgaggcc cagcagggcg | 3540 |
| cgggaggccc tgcccaccaa gtgatcgtgg aagccacaga aaaccccgtc ttcgcccact | 3600 |
| ccactgtggt ccatcccgaa tccaggcatc acccaccctc gaacccgaga cagcagcccc | 3660 |
| acctggactc agggtccctg cctcccggac ggcaaggcca gcagcccgc agggacccc | 3720 |
| ccagagaagg cttgtggcca ccccctaca gaccgcgcag agacgctttt gaaatttcta | 3780 |
| ctgaagggca ttctggcccct agcaataggg cccgctgggg ccctcgcggg gccgttctc | 3840 |
| acaaccctcg gaaccagcg tccactgcca tgggcagctc cgtgcccggc tactgccagc | 3900 |
| ccatcaccac tgtgacggct tctgcctccg tgactgtcgc cgtgcacccg ccgcctgtcc | 3960 |
| ctgggcctgg gcgaaccccc cgaggggac tctgcccagg ctaccctgag actgaccacg | 4020 |
| gcctgtttga ggaccccac gtgccttttcc acgtccggtg tgagaggagg gattcgaagg | 4080 |
| tggaagtcat tgagctgcag gacgtggaat gcgaggagag gccccgggga agcagctcca | 4140 |
| actga | 4145 |

<210> SEQ ID NO 22
<211> LENGTH: 1381
<212> TYPE: PRT
<213> ORGANISM: Homo sapiens

<400> SEQUENCE: 22

Met Gly Lys Ala Thr Gly Arg Lys Ala Pro Leu Trp Leu Arg Ala Lys
1               5                   10                  15

Phe Gln Arg Leu Leu Phe Lys Leu Gly Cys Tyr Ile Gln Lys Asn Cys
                20                  25                  30

Gly Lys Phe Leu Val Val Gly Leu Leu Ile Phe Gly Ala Phe Ala Val
            35                  40                  45

Gly Leu Lys Ala Ala Asn Leu Glu Thr Asn Val Glu Glu Leu Trp Val
        50                  55                  60

```
Glu Val Gly Gly Arg Val Ser Arg Glu Leu Asn Tyr Thr Arg Gln Lys
 65                  70                  75                  80

Ile Gly Glu Glu Ala Met Phe Asn Pro Gln Leu Met Ile Gln Thr Pro
             85                  90                  95

Lys Glu Glu Gly Ala Asn Val Leu Thr Thr Glu Ala Leu Leu Gln His
            100                 105                 110

Leu Asp Ser Ala Leu Gln Ala Ser Arg Val His Val Tyr Met Tyr Asn
            115                 120                 125

Arg Gln Trp Lys Leu Glu His Leu Cys Tyr Lys Ser Gly Glu Leu Ile
130             135                 140

Thr Glu Thr Gly Tyr Met Asp Gln Ile Ile Glu Tyr Leu Tyr Pro Cys
145             150                 155                 160

Leu Ile Ile Thr Pro Leu Asp Cys Phe Trp Glu Gly Ala Lys Leu Gln
                165                 170                 175

Ser Gly Thr Ala Tyr Leu Leu Gly Lys Pro Pro Leu Arg Trp Thr Asn
            180                 185                 190

Phe Asp Pro Leu Glu Phe Leu Glu Glu Leu Lys Lys Ile Asn Tyr Gln
            195                 200                 205

Val Asp Ser Trp Glu Glu Met Leu Asn Lys Ala Glu Val Gly His Gly
210             215                 220

Tyr Met Asp Arg Pro Cys Leu Asn Pro Ala Asp Pro Asp Cys Pro Ala
225             230                 235                 240

Thr Ala Pro Asn Lys Asn Ser Thr Lys Pro Leu Asp Met Ala Leu Val
                245                 250                 255

Leu Asn Gly Gly Cys His Gly Leu Ser Arg Lys Tyr Met His Trp Gln
            260                 265                 270

Glu Glu Leu Ile Val Gly Gly Thr Val Lys Asn Ser Thr Gly Lys Leu
            275                 280                 285

Val Ser Ala His Ala Leu Gln Thr Met Phe Gln Leu Met Thr Pro Lys
290             295                 300

Gln Met Tyr Glu His Phe Lys Gly Tyr Glu Tyr Val Ser His Ile Asn
305             310                 315                 320

Trp Asn Glu Asp Lys Ala Ala Ala Ile Leu Glu Ala Trp Gln Arg Thr
                325                 330                 335

Tyr Val Glu Val Val His Gln Ser Val Ala Gln Asn Ser Thr Gln Lys
            340                 345                 350

Val Leu Ser Phe Thr Thr Thr Thr Leu Asp Asp Ile Leu Lys Ser Phe
            355                 360                 365

Ser Asp Val Ser Val Ile Arg Val Ala Ser Gly Tyr Leu Leu Met Leu
            370                 375                 380

Ala Tyr Ala Cys Leu Thr Met Leu Arg Trp Asp Cys Ser Lys Ser Gln
385             390                 395                 400

Gly Ala Val Gly Leu Ala Gly Val Leu Val Ala Leu Ser Val Ala
            405                 410                 415

Ala Gly Leu Gly Leu Cys Ser Leu Ile Gly Ile Ser Phe Asn Ala Ala
            420                 425                 430

Thr Thr Gln Val Leu Pro Phe Leu Ala Leu Gly Val Gly Val Asp Asp
            435                 440                 445

Val Phe Leu Leu Ala His Ala Phe Ser Glu Thr Gly Gln Asn Lys Arg
            450                 455                 460

Ile Pro Phe Glu Asp Arg Thr Gly Glu Cys Leu Lys Arg Thr Gly Ala
465                 470                 475                 480
```

```
Ser Val Ala Leu Thr Ser Ile Ser Asn Val Thr Ala Phe Phe Met Ala
                485                 490                 495

Ala Leu Ile Pro Ile Pro Ala Leu Arg Ala Phe Ser Leu Gln Ala Ala
            500                 505                 510

Val Val Val Phe Asn Phe Ala Met Val Leu Leu Ile Phe Pro Ala
        515                 520                 525

Ile Leu Ser Met Asp Leu Tyr Arg Arg Glu Asp Arg Leu Asp Ile
    530                 535                 540

Phe Cys Cys Phe Thr Ser Pro Cys Val Ser Arg Val Ile Gln Val Glu
545                 550                 555                 560

Pro Gln Ala Tyr Thr Asp Thr His Asp Asn Thr Arg Tyr Ser Pro Pro
                565                 570                 575

Pro Pro Tyr Ser Ser His Ser Phe Ala His Glu Thr Gln Ile Thr Met
            580                 585                 590

Gln Ser Thr Val Gln Leu Arg Thr Glu Tyr Asp Pro His Thr His Val
        595                 600                 605

Tyr Tyr Thr Thr Ala Glu Pro Arg Ser Glu Ile Ser Val Gln Pro Val
    610                 615                 620

Thr Val Thr Gln Asp Thr Leu Ser Cys Gln Ser Pro Glu Ser Thr Ser
625                 630                 635                 640

Ser Thr Arg Asp Leu Leu Ser Gln Phe Ser Asp Ser Ser Leu His Cys
                645                 650                 655

Leu Glu Pro Pro Cys Thr Lys Trp Thr Leu Ser Ser Phe Ala Glu Lys
            660                 665                 670

His Tyr Ala Pro Phe Leu Leu Lys Pro Lys Ala Lys Val Val Ile
        675                 680                 685

Phe Leu Phe Leu Gly Leu Leu Gly Val Ser Leu Tyr Gly Thr Thr Arg
    690                 695                 700

Val Arg Asp Gly Leu Asp Leu Thr Asp Ile Val Pro Arg Glu Thr Arg
705                 710                 715                 720

Glu Tyr Asp Phe Ile Ala Ala Gln Phe Lys Tyr Phe Ser Phe Tyr Asn
                725                 730                 735

Met Tyr Ile Val Thr Gln Lys Ala Asp Tyr Pro Asn Ile Gln His Leu
            740                 745                 750

Leu Tyr Asp Leu His Arg Ser Phe Ser Asn Val Lys Tyr Val Met Leu
        755                 760                 765

Glu Glu Asn Lys Gln Leu Pro Lys Met Trp Leu His Tyr Phe Arg Asp
    770                 775                 780

Trp Leu Gln Gly Leu Gln Asp Ala Phe Asp Ser Asp Trp Glu Thr Gly
785                 790                 795                 800

Lys Ile Met Pro Asn Asn Tyr Lys Asn Gly Ser Asp Asp Gly Val Leu
                805                 810                 815

Ala Tyr Lys Leu Leu Val Gln Thr Gly Ser Arg Asp Lys Pro Ile Asp
            820                 825                 830

Ile Ser Gln Leu Thr Lys Gln Arg Leu Val Asp Ala Asp Gly Ile Ile
        835                 840                 845

Asn Pro Ser Ala Phe Tyr Ile Tyr Leu Thr Ala Trp Val Ser Asn Asp
    850                 855                 860

Pro Val Ala Tyr Ala Ala Ser Gln Ala Asn Ile Arg Pro His Arg Pro
865                 870                 875                 880

Glu Trp Val His Asp Lys Ala Asp Tyr Met Pro Glu Thr Arg Leu Arg
                885                 890                 895

Ile Pro Ala Ala Glu Pro Ile Glu Tyr Ala Gln Phe Pro Phe Tyr Leu
```

-continued

```
                900                 905                 910
Asn Gly Leu Arg Asp Thr Ser Asp Phe Val Glu Ala Ile Glu Lys Val
            915                 920                 925

Arg Thr Ile Cys Ser Asn Tyr Thr Ser Leu Gly Leu Ser Ser Tyr Pro
930                 935                 940

Asn Gly Tyr Pro Phe Leu Phe Trp Glu Gln Tyr Ile Gly Leu Arg His
945                 950                 955                 960

Trp Leu Leu Leu Phe Ile Ser Val Val Leu Ala Cys Thr Phe Leu Val
                965                 970                 975

Cys Ala Val Phe Leu Leu Asn Pro Trp Thr Ala Gly Ile Ile Val Met
            980                 985                 990

Val Leu Ala Leu Met Thr Val Glu Leu Phe Gly Met Met Gly Leu Ile
        995                 1000                1005

Gly Ile Lys Leu Ser Ala Val Pro Val Val Ile Leu Ile Ala Ser
    1010                1015                1020

Val Gly Ile Gly Val Glu Phe Thr Val His Val Ala Leu Ala Phe
    1025                1030                1035

Leu Thr Ala Ile Gly Asp Lys Asn Arg Arg Ala Val Leu Ala Leu
    1040                1045                1050

Glu His Met Phe Ala Pro Val Leu Asp Gly Ala Val Ser Thr Leu
    1055                1060                1065

Leu Gly Val Leu Met Leu Ala Gly Ser Glu Phe Asp Phe Ile Val
    1070                1075                1080

Arg Tyr Phe Phe Ala Val Leu Ala Ile Leu Thr Ile Leu Gly Val
    1085                1090                1095

Leu Asn Gly Leu Val Leu Leu Pro Val Leu Leu Ser Phe Phe Gly
    1100                1105                1110

Pro Tyr Pro Glu Val Ser Pro Ala Asn Gly Leu Asn Arg Leu Pro
    1115                1120                1125

Thr Pro Ser Pro Glu Pro Pro Pro Ser Val Val Arg Phe Ala Met
    1130                1135                1140

Pro Pro Gly His Thr His Ser Gly Ser Asp Ser Ser Asp Ser Glu
    1145                1150                1155

Tyr Ser Ser Gln Thr Thr Val Ser Gly Leu Ser Glu Glu Leu Arg
    1160                1165                1170

His Tyr Glu Ala Gln Gln Gly Ala Gly Gly Pro Ala His Gln Val
    1175                1180                1185

Ile Val Glu Ala Thr Glu Asn Pro Val Phe Ala His Ser Thr Val
    1190                1195                1200

Val His Pro Glu Ser Arg His His Pro Pro Ser Asn Pro Arg Gln
    1205                1210                1215

Gln Pro His Leu Asp Ser Gly Ser Leu Pro Pro Gly Arg Gln Gly
    1220                1225                1230

Gln Gln Pro Arg Arg Asp Pro Pro Arg Glu Gly Leu Trp Pro Pro
    1235                1240                1245

Pro Tyr Arg Pro Arg Arg Asp Ala Phe Glu Ile Ser Thr Glu Gly
    1250                1255                1260

His Ser Gly Pro Ser Asn Arg Ala Arg Trp Gly Pro Arg Gly Ala
    1265                1270                1275

Arg Ser His Asn Pro Arg Asn Pro Ala Ser Thr Ala Met Gly Ser
    1280                1285                1290

Ser Val Pro Gly Tyr Cys Gln Pro Ile Thr Thr Val Thr Ala Ser
    1295                1300                1305
```

```
Ala Ser Val Thr Val Ala Val His Pro Pro Val Pro Gly Pro
    1310            1315            1320

Gly Arg Asn Pro Arg Gly Gly Leu Cys Pro Gly Tyr Pro Glu Thr
1325            1330            1335

Asp His Gly Leu Phe Glu Asp Pro His Val Pro Phe His Val Arg
    1340            1345            1350

Cys Glu Arg Arg Asp Ser Lys Val Glu Val Ile Glu Leu Gln Asp
    1355            1360            1365

Val Glu Cys Glu Glu Arg Pro Arg Gly Ser Ser Ser Asn
    1370            1375            1380

<210> SEQ ID NO 23
<211> LENGTH: 3612
<212> TYPE: DNA
<213> ORGANISM: Homo sapiens

<400> SEQUENCE: 23
```

| | | | | | |
|---|---|---|---|---|---|
| atgactcgat | cgccgcccct | cagagagctg | cccccgagtt | acacaccccc | agctcgaacc | 60 |
| gcagcacccc | agatcctagc | tgggagcctg | aaggctccac | tctggcttcg | tgcttacttc | 120 |
| cagggcctgc | tcttctctct | gggatgcggg | atccagagac | attgtggcaa | agtgctcttt | 180 |
| ctggactgt | tggcctttgg | ggccctggca | ttaggtctcc | gcatggccat | tattgagaca | 240 |
| aacttggaac | agctctgggt | agaagtgggc | agccgggtga | gccaggagct | gcattacacc | 300 |
| aaggagaagc | tggggagga | ggctgcatac | acctctcaga | tgctgataca | gaccgcacgc | 360 |
| caggagggag | agaacatcct | cacacccgaa | gcacttggcc | tccacctcca | ggcagccctc | 420 |
| actgccagta | agtccaagt | atcactctat | gggaagtcct | gggatttgaa | caaaatctgc | 480 |
| tacaagtcag | gagttcccct | tattgaaaat | ggaatgattg | agtggatgat | tgagaagctg | 540 |
| tttccgtgcg | tgatcctcac | cccctcgac | tgcttctggg | agggagccaa | actccaaggg | 600 |
| ggctccgcct | acctgcccgg | ccgcccggat | atccagtgga | ccaacctgga | tccagagcag | 660 |
| ctgctggagg | agctgggtcc | cttttgcctcc | cttgagggct | tccgggagct | gctagacaag | 720 |
| gcacaggtgg | gccaggccta | cgtggggcgg | ccctgtctgc | accctgatga | cctccactgc | 780 |
| ccacctagtg | cccccaacca | tcacagcagg | caggctccca | atgtggctca | cgagctgagt | 840 |
| gggggctgcc | atggcttctc | ccacaaattc | atgcactggc | aggaggaatt | gctgctggga | 900 |
| ggcatggcca | gagaccccca | aggagagctg | ctgagggcag | aggccctgca | gagcaccttc | 960 |
| ttgctgatga | gtccccgcca | gctgtacgag | catttccggg | gtgactatca | gacacatgac | 1020 |
| attggctgga | gtgaggagca | ggccagcaca | gtgctacaag | cctggcagcg | gcgctttgtg | 1080 |
| cagctggccc | aggaggccct | gcctgagaac | gcttcccagc | agatccatgc | cttctcctcc | 1140 |
| accaccctgg | atgacatcct | gcatgcgttc | tctgaagtca | gtgctgcccg | tgtggtggga | 1200 |
| ggctatctgc | tcatgctggc | ctatgcctgt | gtgaccatgc | tgcggtggga | ctgcgcccag | 1260 |
| tcccagggtt | ccgtgggcct | tgccggggta | ctgctggtgg | ccctggcggt | ggcctcaggc | 1320 |
| cttgggctct | gtgccctgct | cggcatcacc | ttcaatgctg | ccactaccca | ggtgctgcct | 1380 |
| ttcttggctc | tgggaatcgg | cgtggatgac | gtattcctgc | tggcgcatgc | cttcacagag | 1440 |
| gctctgcctg | gcacccctct | ccaggagcgc | atgggcgagt | gtctgcagcg | cacgggcacc | 1500 |
| agtgtcgtac | tcacatccat | caacaacatg | gccgccttcc | tcatggctgc | cctcgttccc | 1560 |
| atccctgcgc | tgcgagcctt | ctccctacag | gcggccatag | tggttggctg | cacctttgta | 1620 |
| gccgtgatgc | ttgtcttccc | agccatcctc | agcctggacc | tacggcggcg | ccactgccag | 1680 |

```
cgccttgatg tgctctgctg cttctccagt ccctgctctg ctcaggtgat tcagatcctg    1740 cccccaggagc tggggacgg gacagtacca gtgggcattg cccacctcac tgccacagtt    1800
caagccttta cccactgtga agccagcagc cagcatgtgg tcaccatcct gcctccccaa    1860
gcccacctgg tgcccccacc ttctgaccca ctgggtctg agctcttcag ccctggaggg     1920
tccacacggg accttctagg ccaggaggag gagacaaggc agaaggcagc ctgcaagtcc    1980
ctgccctgtg cccgctggaa tcttgcccat ttcgcccgct atcagtttgc cccgttgctg    2040
ctccagtcac atgccaaggc catcgtgctg gtgctctttg gtgctcttct gggcctgagc    2100
ctctacggag ccaccttggt gcaagacggc ctggccctga cggatgtggt gcctcggggc    2160
accaaggagc atgccttcct gagcgcccag ctcaggtact tctccctgta cgaggtggcc    2220
ctggtgaccc agggtggctt tgactacgcc cattcccaac gcgccctctt tgatctgcac    2280
cagcgcttca gttccctcaa ggcggtgctg ccccaccggg cccccaggc acccccgcacc    2340 tggctgcact attaccgcaa ctggctacag ggaatccagg ctgcctttga ccaggactgg    2400
gcttctgggc gcatcacccg ccactcgtac cgcaatggct ctgaggatgg ggccctggcc    2460
tacaagctgc tcatccagac tggagacgcc caggagcctc tggatttcag ccagctgacc    2520
acaaggaagc tggtggacag agagggactg attccacccg agctcttcta catggggctg    2580
accgtgtggg tgagcagtga ccccctgggt ctggcagcct cacaggccaa cttctacccc    2640
ccacctcctg aatggctgca cgacaaatac gacaccacgg gggagaacct tcgcatcccg    2700
ccagctcagc ccttggagtt tgcccagttc cccttcctgc tgcgtggcct ccagaagact    2760
gcagactttg tggaggccat cgagggggcc cgggcagcat gcgcagaggc cggccaggct    2820
ggggtgcacg cctaccccag cggctccccc ttcctcttct gggaacagta tctgggcctg    2880
cggcgctgct tcctgctggc cgtctgcatc ctgctggtgt gcactttcct cgtctgtgct    2940
ctgctgctcc tcaaccccctg gacggctggc tcatagtgc tggtcctggc gatgatgaca    3000
gtggaactct ttggtatcat gggtttcctg ggcatcaagc tgagtgccat ccccgtggtg    3060
atccttgtgg cctctgtagg cattggcgtt gagttcacag tccacgtggc tctgggcttc    3120
ctgaccaccc agggcagccg gaacctgcgg ccgcccatg cccttgagca cacatttgcc     3180
cccgtgaccg atggggccat ctccacattg ctgggtctgc tcatgcttgc tggttcccac    3240
tttgacttca ttgtaaggta cttctttgcg gcgctgacag tgctcacgct cctgggcctc    3300
ctccatggac tcgtgctgct gcctgtgctg ctgtccatcc tgggcccgcc gccagaggtg    3360
atacagatgt acaaggaaag cccagagatc ctgagtccac cagctccaca gggaggcggg    3420
cttaggtggg gggcatcctc ctccctgccc cagagctttg ccagagtgac tacctccatg    3480
accgtggcca tccaccccacc cccctgcct ggtgcctaca tccatccagc ccctgatgag     3540 ccccccttggt cccctgctgc cactagctct ggcaacctca gttccagggg accaggtcca    3600
gccactgggt ga                                                        3612
```

<210> SEQ ID NO 24
<211> LENGTH: 1203
<212> TYPE: PRT
<213> ORGANISM: Homo sapiens
<400> SEQUENCE: 24

```
Met Thr Arg Ser Pro Pro Leu Arg Glu Leu Pro Pro Ser Tyr Thr Pro
1               5                   10                  15

Pro Ala Arg Thr Ala Ala Pro Gln Ile Leu Ala Gly Ser Leu Lys Ala
```

-continued

```
                 20                  25                  30
Pro Leu Trp Leu Arg Ala Tyr Phe Gln Gly Leu Leu Phe Ser Leu Gly
             35                  40                  45
Cys Gly Ile Gln Arg His Cys Gly Lys Val Leu Phe Leu Gly Leu Leu
         50                  55                  60
Ala Phe Gly Ala Leu Ala Leu Gly Leu Arg Met Ala Ile Ile Glu Thr
 65                  70                  75                  80
Asn Leu Glu Gln Leu Trp Val Glu Val Gly Ser Arg Val Ser Gln Glu
                 85                  90                  95
Leu His Tyr Thr Lys Glu Lys Leu Gly Glu Glu Ala Ala Tyr Thr Ser
            100                 105                 110
Gln Met Leu Ile Gln Thr Ala Arg Gln Glu Gly Glu Asn Ile Leu Thr
            115                 120                 125
Pro Glu Ala Leu Gly Leu His Leu Gln Ala Ala Leu Thr Ala Ser Lys
            130                 135                 140
Val Gln Val Ser Leu Tyr Gly Lys Ser Trp Asp Leu Asn Lys Ile Cys
145                 150                 155                 160
Tyr Lys Ser Gly Val Pro Leu Ile Glu Asn Gly Met Ile Glu Trp Met
                165                 170                 175
Ile Glu Lys Leu Phe Pro Cys Val Ile Leu Thr Pro Leu Asp Cys Phe
            180                 185                 190
Trp Glu Gly Ala Lys Leu Gln Gly Gly Ser Ala Tyr Leu Pro Gly Arg
            195                 200                 205
Pro Asp Ile Gln Trp Thr Asn Leu Asp Pro Glu Gln Leu Leu Glu Glu
            210                 215                 220
Leu Gly Pro Phe Ala Ser Leu Glu Gly Phe Arg Glu Leu Leu Asp Lys
225                 230                 235                 240
Ala Gln Val Gly Gln Ala Tyr Val Gly Arg Pro Cys Leu His Pro Asp
                245                 250                 255
Asp Leu His Cys Pro Pro Ser Ala Pro Asn His His Ser Arg Gln Ala
            260                 265                 270
Pro Asn Val Ala His Glu Leu Ser Gly Gly Cys His Gly Phe Ser His
            275                 280                 285
Lys Phe Met His Trp Gln Glu Glu Leu Leu Leu Gly Gly Met Ala Arg
            290                 295                 300
Asp Pro Gln Gly Glu Leu Leu Arg Ala Glu Ala Leu Gln Ser Thr Phe
305                 310                 315                 320
Leu Leu Met Ser Pro Arg Gln Leu Tyr Glu His Phe Arg Gly Asp Tyr
                325                 330                 335
Gln Thr His Asp Ile Gly Trp Ser Glu Glu Gln Ala Ser Thr Val Leu
            340                 345                 350
Gln Ala Trp Gln Arg Arg Phe Val Gln Leu Ala Gln Glu Ala Leu Pro
            355                 360                 365
Glu Asn Ala Ser Gln Gln Ile His Ala Phe Ser Ser Thr Thr Leu Asp
            370                 375                 380
Asp Ile Leu His Ala Phe Ser Glu Val Ser Ala Ala Arg Val Val Gly
385                 390                 395                 400
Gly Tyr Leu Leu Met Leu Ala Tyr Ala Cys Val Thr Met Leu Arg Trp
                405                 410                 415
Asp Cys Ala Gln Ser Gln Gly Ser Val Gly Leu Ala Gly Val Leu Leu
            420                 425                 430
Val Ala Leu Ala Val Ala Ser Gly Leu Gly Leu Cys Ala Leu Leu Gly
            435                 440                 445
```

-continued

```
Ile Thr Phe Asn Ala Ala Thr Thr Gln Val Leu Pro Phe Leu Ala Leu
    450                 455                 460
Gly Ile Gly Val Asp Asp Val Phe Leu Leu Ala His Ala Phe Thr Glu
465                 470                 475                 480
Ala Leu Pro Gly Thr Pro Leu Gln Glu Arg Met Gly Glu Cys Leu Gln
                485                 490                 495
Arg Thr Gly Thr Ser Val Val Leu Thr Ser Ile Asn Asn Met Ala Ala
                500                 505                 510
Phe Leu Met Ala Ala Leu Val Pro Ile Pro Ala Leu Arg Ala Phe Ser
            515                 520                 525
Leu Gln Ala Ala Ile Val Val Gly Cys Thr Phe Val Ala Val Met Leu
    530                 535                 540
Val Phe Pro Ala Ile Leu Ser Leu Asp Leu Arg Arg Arg His Cys Gln
545                 550                 555                 560
Arg Leu Asp Val Leu Cys Cys Phe Ser Ser Pro Cys Ser Ala Gln Val
                565                 570                 575
Ile Gln Ile Leu Pro Gln Glu Leu Gly Asp Gly Thr Val Pro Val Gly
                580                 585                 590
Ile Ala His Leu Thr Ala Thr Val Gln Ala Phe Thr His Cys Glu Ala
            595                 600                 605
Ser Ser Gln His Val Val Thr Ile Leu Pro Pro Gln Ala His Leu Val
    610                 615                 620
Pro Pro Pro Ser Asp Pro Leu Gly Ser Glu Leu Phe Ser Pro Gly Gly
625                 630                 635                 640
Ser Thr Arg Asp Leu Leu Gly Gln Glu Glu Thr Arg Gln Lys Ala
                645                 650                 655
Ala Cys Lys Ser Leu Pro Cys Ala Arg Trp Asn Leu Ala His Phe Ala
                660                 665                 670
Arg Tyr Gln Phe Ala Pro Leu Leu Gln Ser His Ala Lys Ala Ile
            675                 680                 685
Val Leu Val Leu Phe Gly Ala Leu Leu Gly Leu Ser Leu Tyr Gly Ala
    690                 695                 700
Thr Leu Val Gln Asp Gly Leu Ala Leu Thr Asp Val Val Pro Arg Gly
705                 710                 715                 720
Thr Lys Glu His Ala Phe Leu Ser Ala Gln Leu Arg Tyr Phe Ser Leu
                725                 730                 735
Tyr Glu Val Ala Leu Val Thr Gln Gly Gly Phe Asp Tyr Ala His Ser
                740                 745                 750
Gln Arg Ala Leu Phe Asp Leu His Gln Arg Phe Ser Ser Leu Lys Ala
            755                 760                 765
Val Leu Pro Pro Pro Ala Thr Gln Ala Pro Arg Thr Trp Leu His Tyr
    770                 775                 780
Tyr Arg Asn Trp Leu Gln Gly Ile Gln Ala Ala Phe Asp Gln Asp Trp
785                 790                 795                 800
Ala Ser Gly Arg Ile Thr His Ser Tyr Arg Asn Gly Ser Glu Asp
                805                 810                 815
Gly Ala Leu Ala Tyr Lys Leu Leu Ile Gln Thr Gly Asp Ala Gln Glu
            820                 825                 830
Pro Leu Asp Phe Ser Gln Leu Thr Thr Arg Lys Leu Val Asp Arg Glu
            835                 840                 845
Gly Leu Ile Pro Pro Glu Leu Phe Tyr Met Gly Leu Thr Val Trp Val
    850                 855                 860
```

Ser Ser Asp Pro Leu Gly Leu Ala Ala Ser Gln Ala Asn Phe Tyr Pro
865                 870                 875                 880

Pro Pro Pro Glu Trp Leu His Asp Lys Tyr Asp Thr Thr Gly Glu Asn
                885                 890                 895

Leu Arg Ile Pro Pro Ala Gln Pro Leu Glu Phe Ala Gln Phe Pro Phe
            900                 905                 910

Leu Leu Arg Gly Leu Gln Lys Thr Ala Asp Phe Val Glu Ala Ile Glu
        915                 920                 925

Gly Ala Arg Ala Ala Cys Ala Glu Ala Gly Gln Ala Gly Val His Ala
    930                 935                 940

Tyr Pro Ser Gly Ser Pro Phe Leu Phe Trp Glu Gln Tyr Leu Gly Leu
945                 950                 955                 960

Arg Arg Cys Phe Leu Leu Ala Val Cys Ile Leu Leu Val Cys Thr Phe
                965                 970                 975

Leu Val Cys Ala Leu Leu Leu Asn Pro Trp Thr Ala Gly Leu Ile
            980                 985                 990

Val Leu Val Leu Ala Met Met Thr Val Glu Leu Phe Gly Ile Met Gly
        995                 1000                1005

Phe Leu Gly Ile Lys Leu Ser Ala Ile Pro Val Val Ile Leu Val
    1010                1015                1020

Ala Ser Val Gly Ile Gly Val Glu Phe Thr Val His Val Ala Leu
    1025                1030                1035

Gly Phe Leu Thr Thr Gln Gly Ser Arg Asn Leu Arg Ala Ala His
    1040                1045                1050

Ala Leu Glu His Thr Phe Ala Pro Val Thr Asp Gly Ala Ile Ser
    1055                1060                1065

Thr Leu Leu Gly Leu Leu Met Leu Ala Gly Ser His Phe Asp Phe
    1070                1075                1080

Ile Val Arg Tyr Phe Phe Ala Ala Leu Thr Val Leu Thr Leu Leu
    1085                1090                1095

Gly Leu Leu His Gly Leu Val Leu Leu Pro Val Leu Leu Ser Ile
    1100                1105                1110

Leu Gly Pro Pro Pro Glu Val Ile Gln Met Tyr Lys Glu Ser Pro
    1115                1120                1125

Glu Ile Leu Ser Pro Pro Ala Pro Gln Gly Gly Gly Leu Arg Trp
    1130                1135                1140

Gly Ala Ser Ser Ser Leu Pro Gln Ser Phe Ala Arg Val Thr Thr
    1145                1150                1155

Ser Met Thr Val Ala Ile His Pro Pro Pro Leu Pro Gly Ala Tyr
    1160                1165                1170

Ile His Pro Ala Pro Asp Glu Pro Pro Trp Ser Pro Ala Ala Thr
    1175                1180                1185

Ser Ser Gly Asn Leu Ser Ser Arg Gly Pro Gly Pro Ala Thr Gly
    1190                1195                1200

<210> SEQ ID NO 25
<211> LENGTH: 2364
<212> TYPE: DNA
<213> ORGANISM: Homo sapiens

<400> SEQUENCE: 25
atggccgctg cccgcccagc gcgggggccg gagctcccgc tcctggggct gctgctgctg      60
ctgctgctgg ggacccgggg ccggggggcg gcctcgagcg ggaacgcgac cgggcctggg     120
cctcggagcg cgggcgggag cgcgaggagg agcgcggcgg tgactggccc tccgccgccg     180

```
ctgagccact gcggccgggc tgcccctgc gagccgctgc gctacaacgt gtgcctgggc    240
tcggtgctgc cctacggggc cacctccaca ctgctggccg gagactcgga ctcccaggag    300
gaagcgcacg gcaagctcgt gctctggtcg ggcctccgga atgcccccg ctgctgggca    360 gtgatccagc ccctgctgtg tgccgtatac atgcccaagt gtgagaatga ccgggtggag    420
ctgcccagcc gtaccctctg ccaggccacc cgaggcccct gtgccatcgt ggagagggag    480
cggggctggc ctgacttcct cgctgcact cctgaccgct tccctgaagg ctgcacgaat    540
gaggtgcaga acatcaagtt caacagttca ggccagtgcg aagtgcccttggttcggaca    600 gacaacccca gagctggta cgaggacgtg gagggctgcg gcatccagtg ccagaacccg    660
ctcttcacag aggctgagca ccaggacatg cacagctaca tcgcggcctt cggggccgtc    720
acgggcctct gcacgctctt caccctggcc acattcgtgg ctgactgcg gaactcgaat    780 cgctaccctg ctgttattct cttctacgtc aatgcgtgct tctttgtggg cagcattggc    840
tggctggccc agttcatgga tggtgcccgc cgagagatcg tctgccgtgc agatggcacc    900
atgaggcttg gggagcccac ctccaatgag actctgtcct gcgtcatcat ctttgtcatc    960
gtgtactacg ccctgatggc tggtgtggtt tggtttgtgg tcctcaccta tgcctggcac    1020
acttccttca agccctggg caccacctac cagcctctct cgggcaagac ctcctacttc    1080
cacctgctca cctggtcact cccctttgtc ctcactgtgg caatccttgc tgtggcgcag    1140
gtggatgggg actctgtgag tgggatttgt tttgtgggct acaagaacta ccgataccgt    1200
gcgggcttcg tgctggcccc aatcggcctg gtgctcatcg tgggaggcta cttcctcatc    1260
cgaggagtca tgactctgtt ctccatcaag agcaaccacc ccgggctgct gagtgagaag    1320
gctgccagca agatcaacga gaccatgctg cgcctgggca ttttggcttcctggccttt    1380 ggctttgtgc tcattacctt cagctgccac ttctacgact tcttcaacca ggctgagtgg    1440
gagcgcagct ccgggacta tgtgctatgt caggccaatg tgaccatcgg gctgccacc    1500 aagcagccca tccctgactg tgagatcaag aatcgcccga gccttctggt ggagaagatc    1560
aacctgtttg ccatgtttgg aactggcatc gccatgagca cctgggtctg gaccaaggcc    1620
acgctgctca tctggaggcg tacctggtgc aggttgactg ggcagagtga cgatgagcca    1680
aagcggatca agaagagcaa gatgattgcc aaggccttct ctaagcggca cgagctcctg    1740
cagaacccag gccaggagct gtccttcagc atgcacactg tgtcccacga cgggcccgtg    1800
gcgggcttgg cctttgacct caatgagccc tcagctgatg tctcctctgc ctgggcccag    1860
catgtcacca agatggtggc tcggagagga gccatactgc cccaggatat ttctgtcacc    1920
cctgtggcaa ctccagtgcc cccagaggaa caagccaacc tgtggctggt tgaggcagag    1980
atctccccag agctgcagaa gcgcctgggc cggaagaaga gaggaggaa gaggaagaag    2040 gaggtgtgcc cgctggcgcc gccccctgag cttcacccccctgcccctgc cccagtacc    2100 attcctcgac tgcctcagct gccccggcag aaatgcctgg tggctgcagg tgcctgggga    2160
gctggggact cttgccgaca gggagcgtgg accctggtct ccaacccattctgcccagag    2220 cccagtcccc ctcaggatcc attttctgccc agtgcaccgg ccccgtggc atgggctcat    2280 ggccgccgac agggcctggg gcctattcac tcccgcacca acctgatgga cacagaactc    2340
atggatgcag actcggactt ctga                                            2364
```

<210> SEQ ID NO 26
<211> LENGTH: 787
<212> TYPE: PRT

<213> ORGANISM: Homo sapiens

<400> SEQUENCE: 26

| | | | | | | | | | | | | | | |
|---|---|---|---|---|---|---|---|---|---|---|---|---|---|---|
| Met | Ala | Ala | Ala | Arg | Pro | Ala | Arg | Gly | Pro | Glu | Leu | Pro | Leu | Leu | Gly |
| 1 | | | | 5 | | | | | 10 | | | | | 15 | |
| Leu | Leu | Leu | Leu | Leu | Leu | Leu | Gly | Asp | Pro | Gly | Arg | Gly | Ala | Ala | Ser |
| | | | 20 | | | | | 25 | | | | | 30 | | |
| Ser | Gly | Asn | Ala | Thr | Gly | Pro | Gly | Pro | Arg | Ser | Ala | Gly | Gly | Ser | Ala |
| | | 35 | | | | | 40 | | | | | 45 | | | |
| Arg | Arg | Ser | Ala | Ala | Val | Thr | Gly | Pro | Pro | Pro | Leu | Ser | His | Cys | |
| 50 | | | | | 55 | | | | | 60 | | | | | |
| Gly | Arg | Ala | Ala | Pro | Cys | Glu | Pro | Leu | Arg | Tyr | Asn | Val | Cys | Leu | Gly |
| 65 | | | | | 70 | | | | | 75 | | | | | 80 |
| Ser | Val | Leu | Pro | Tyr | Gly | Ala | Thr | Ser | Thr | Leu | Leu | Ala | Gly | Asp | Ser |
| | | | | 85 | | | | | 90 | | | | | 95 | |
| Asp | Ser | Gln | Glu | Glu | Ala | His | Gly | Lys | Leu | Val | Leu | Trp | Ser | Gly | Leu |
| | | | 100 | | | | | 105 | | | | | 110 | | |
| Arg | Asn | Ala | Pro | Arg | Cys | Trp | Ala | Val | Ile | Gln | Pro | Leu | Leu | Cys | Ala |
| | | 115 | | | | | 120 | | | | | 125 | | | |
| Val | Tyr | Met | Pro | Lys | Cys | Glu | Asn | Asp | Arg | Val | Glu | Leu | Pro | Ser | Arg |
| 130 | | | | | 135 | | | | | 140 | | | | | |
| Thr | Leu | Cys | Gln | Ala | Thr | Arg | Gly | Pro | Cys | Ala | Ile | Val | Glu | Arg | Glu |
| 145 | | | | | 150 | | | | | 155 | | | | | 160 |
| Arg | Gly | Trp | Pro | Asp | Phe | Leu | Arg | Cys | Thr | Pro | Asp | Arg | Phe | Pro | Glu |
| | | | | 165 | | | | | 170 | | | | | 175 | |
| Gly | Cys | Thr | Asn | Glu | Val | Gln | Asn | Ile | Lys | Phe | Asn | Ser | Ser | Gly | Gln |
| | | | 180 | | | | | 185 | | | | | 190 | | |
| Cys | Glu | Val | Pro | Leu | Val | Arg | Thr | Asp | Asn | Pro | Lys | Ser | Trp | Tyr | Glu |
| | | 195 | | | | | 200 | | | | | 205 | | | |
| Asp | Val | Glu | Gly | Cys | Gly | Ile | Gln | Cys | Gln | Asn | Pro | Leu | Phe | Thr | Glu |
| 210 | | | | | 215 | | | | | 220 | | | | | |
| Ala | Glu | His | Gln | Asp | Met | His | Ser | Tyr | Ile | Ala | Ala | Phe | Gly | Ala | Val |
| 225 | | | | | 230 | | | | | 235 | | | | | 240 |
| Thr | Gly | Leu | Cys | Thr | Leu | Phe | Thr | Leu | Ala | Thr | Phe | Val | Ala | Asp | Trp |
| | | | | 245 | | | | | 250 | | | | | 255 | |
| Arg | Asn | Ser | Asn | Arg | Tyr | Pro | Ala | Val | Ile | Leu | Phe | Tyr | Val | Asn | Ala |
| | | | 260 | | | | | 265 | | | | | 270 | | |
| Cys | Phe | Phe | Val | Gly | Ser | Ile | Gly | Trp | Leu | Ala | Gln | Phe | Met | Asp | Gly |
| | | 275 | | | | | 280 | | | | | 285 | | | |
| Ala | Arg | Arg | Glu | Ile | Val | Cys | Arg | Ala | Asp | Gly | Thr | Met | Arg | Leu | Gly |
| | | 290 | | | | | 295 | | | | | 300 | | | |
| Glu | Pro | Thr | Ser | Asn | Glu | Thr | Leu | Ser | Cys | Val | Ile | Ile | Phe | Val | Ile |
| 305 | | | | | 310 | | | | | 315 | | | | | 320 |
| Val | Tyr | Tyr | Ala | Leu | Met | Ala | Gly | Val | Val | Trp | Phe | Val | Val | Leu | Thr |
| | | | | 325 | | | | | 330 | | | | | 335 | |
| Tyr | Ala | Trp | His | Thr | Ser | Phe | Lys | Ala | Leu | Gly | Thr | Thr | Tyr | Gln | Pro |
| | | | 340 | | | | | 345 | | | | | 350 | | |
| Leu | Ser | Gly | Lys | Thr | Ser | Tyr | Phe | His | Leu | Leu | Thr | Trp | Ser | Leu | Pro |
| | | | 355 | | | | | 360 | | | | | 365 | | |
| Phe | Val | Leu | Thr | Val | Ala | Ile | Leu | Ala | Val | Ala | Gln | Val | Asp | Gly | Asp |
| | | 370 | | | | | 375 | | | | | 380 | | | |
| Ser | Val | Ser | Gly | Ile | Cys | Phe | Val | Gly | Tyr | Lys | Asn | Tyr | Arg | Tyr | Arg |
| 385 | | | | | 390 | | | | | 395 | | | | | 400 |

Ala Gly Phe Val Leu Ala Pro Ile Gly Leu Val Leu Ile Val Gly Gly
            405                 410                 415

Tyr Phe Leu Ile Arg Gly Val Met Thr Leu Phe Ser Ile Lys Ser Asn
        420                 425                 430

His Pro Gly Leu Leu Ser Glu Lys Ala Ala Ser Lys Ile Asn Glu Thr
    435                 440                 445

Met Leu Arg Leu Gly Ile Phe Gly Phe Leu Ala Phe Gly Phe Val Leu
450                 455                 460

Ile Thr Phe Ser Cys His Phe Tyr Asp Phe Phe Asn Gln Ala Glu Trp
465                 470                 475                 480

Glu Arg Ser Phe Arg Asp Tyr Val Leu Cys Gln Ala Asn Val Thr Ile
                485                 490                 495

Gly Leu Pro Thr Lys Gln Pro Ile Pro Asp Cys Glu Ile Lys Asn Arg
            500                 505                 510

Pro Ser Leu Leu Val Glu Lys Ile Asn Leu Phe Ala Met Phe Gly Thr
        515                 520                 525

Gly Ile Ala Met Ser Thr Trp Val Trp Thr Lys Ala Thr Leu Leu Ile
    530                 535                 540

Trp Arg Arg Thr Trp Cys Arg Leu Thr Gly Gln Ser Asp Asp Glu Pro
545                 550                 555                 560

Lys Arg Ile Lys Lys Ser Lys Met Ile Ala Lys Ala Phe Ser Lys Arg
                565                 570                 575

His Glu Leu Leu Gln Asn Pro Gly Gln Glu Leu Ser Phe Ser Met His
            580                 585                 590

Thr Val Ser His Asp Gly Pro Val Ala Gly Leu Ala Phe Asp Leu Asn
        595                 600                 605

Glu Pro Ser Ala Asp Val Ser Ser Ala Trp Ala Gln His Val Thr Lys
    610                 615                 620

Met Val Ala Arg Arg Gly Ala Ile Leu Pro Gln Asp Ile Ser Val Thr
625                 630                 635                 640

Pro Val Ala Thr Pro Val Pro Pro Glu Glu Gln Ala Asn Leu Trp Leu
                645                 650                 655

Val Glu Ala Glu Ile Ser Pro Glu Leu Gln Lys Arg Leu Gly Arg Lys
            660                 665                 670

Lys Lys Arg Arg Lys Arg Lys Lys Glu Val Cys Pro Leu Ala Pro Pro
        675                 680                 685

Pro Glu Leu His Pro Pro Ala Pro Ala Pro Ser Thr Ile Pro Arg Leu
    690                 695                 700

Pro Gln Leu Pro Arg Gln Lys Cys Leu Val Ala Ala Gly Ala Trp Gly
705                 710                 715                 720

Ala Gly Asp Ser Cys Arg Gln Gly Ala Trp Thr Leu Val Ser Asn Pro
                725                 730                 735

Phe Cys Pro Glu Pro Ser Pro Gln Asp Pro Phe Leu Pro Ser Ala
            740                 745                 750

Pro Ala Pro Val Ala Trp Ala His Gly Arg Arg Gln Gly Leu Gly Pro
        755                 760                 765

Ile His Ser Arg Thr Asn Leu Met Asp Thr Glu Leu Met Asp Ala Asp
    770                 775                 780

Ser Asp Phe
785

<210> SEQ ID NO 27
<211> LENGTH: 1455
<212> TYPE: DNA

<213> ORGANISM: Homo sapiens

<400> SEQUENCE: 27

```
atggcggagc tgcggcctag cggcgccccc ggccccaccg cgccccggc ccctggcccg      60
actgccccc cggccttcgc ttcgctcttt ccccgggac tgcacgccat ctacggagag      120
tgccgccgcc tttaccctga ccagccgaac ccgctccagg ttaccgctat cgtcaagtac     180
tggttgggtg gcccagaccc cttggactat gttagcatgt acaggaatgt ggggagccct     240
tctgctaaca tccccgagca ctggcactac atcagcttcg gcctgagtga tctctatggt     300
gacaacagag tccatgagtt tacaggaaca gatggaccta gtggttttgg ctttgagttg     360
acctttcgtc tgaagagaga aactggggag tctgccccac caacatggcc cgcagagtta     420
atgcagggct tggcacgata cgtgttccag tcagagaaca ccttctgcag tggggaccat     480
gtgtcctggc acagcccttt ggataacagt gagtcaagaa ttcagcacat gctgctgaca     540
gaggacccac agatgcagcc cgtgcagaca ccctttgggg tagttacctt cctccagatc     600
gttggtgtct gcactgaaga gctacactca gcccagcagt ggaacgggca gggcatcctg     660
gagctgctgc ggacagtgcc tattgctggc ggcccctggc tgataactga catgcggagg     720
ggagagacca tatttgagat cgatccacac ctgcaagaga gagttgacaa aggcatcgag     780
acagatggct ccaacctgag tggtgtcagt gccaagtgtg cctgggatga cctgagccgg     840
ccccccgagg atgacgagga cagccggagc atctgcatcg cacacagcc ccggcgactc      900
tctggcaaag acacagagca gatccgggag accctgagga gaggactcga gatcaacagc     960
aaacctgtcc ttccaccaat caaccctcag cggcagaatg cctcgcccca cgaccgggcc    1020
ccgagccgca agacagcct ggaaagtgac agctccacgg ccatcattcc ccatgagctg     1080
attcgcacgc ggcagcttga gagcgtacat ctgaaattca accaggagtc cggagccctc    1140
attcctctct gcctaagggg caggctcctg catggacggc actttacata taaaagtatc    1200
acaggtgaca tggccatcac gtttgtctcc acgggagtgg aaggcgcctt tgccactgag    1260
gagcatcctt acgcggctca tggaccctgg ttacaaattc tgttgaccga gagtttgta     1320
gagaaaatgt tggaggattt agaagatttg acttctccag aggaattcaa acttcccaaa    1380
gagtacagct ggcctgaaaa gaagctgaag gtctccatcc tgcctgacgt ggtgttcgac    1440
agtccgctac actag                                                    1455
```

<210> SEQ ID NO 28
<211> LENGTH: 484
<212> TYPE: PRT
<213> ORGANISM: Homo sapiens

<400> SEQUENCE: 28

```
Met Ala Glu Leu Arg Pro Ser Gly Ala Pro Gly Pro Thr Ala Pro Pro
1               5                   10                  15

Ala Pro Gly Pro Thr Ala Pro Pro Ala Phe Ala Ser Leu Phe Pro Pro
                20                  25                  30

Gly Leu His Ala Ile Tyr Gly Glu Cys Arg Arg Leu Tyr Pro Asp Gln
            35                  40                  45

Pro Asn Pro Leu Gln Val Thr Ala Ile Val Lys Tyr Trp Leu Gly Gly
        50                  55                  60

Pro Asp Pro Leu Asp Tyr Val Ser Met Tyr Arg Asn Val Gly Ser Pro
65                  70                  75                  80

Ser Ala Asn Ile Pro Glu His Trp His Tyr Ile Ser Phe Gly Leu Ser
                85                  90                  95
```

```
Asp Leu Tyr Gly Asp Asn Arg Val His Glu Phe Thr Gly Thr Asp Gly
            100                 105                 110

Pro Ser Gly Phe Gly Phe Glu Leu Thr Phe Arg Leu Lys Arg Glu Thr
        115                 120                 125

Gly Glu Ser Ala Pro Pro Thr Trp Pro Ala Glu Leu Met Gln Gly Leu
    130                 135                 140

Ala Arg Tyr Val Phe Gln Ser Glu Asn Thr Phe Cys Ser Gly Asp His
145                 150                 155                 160

Val Ser Trp His Ser Pro Leu Asp Asn Ser Glu Ser Arg Ile Gln His
                165                 170                 175

Met Leu Leu Thr Glu Asp Pro Gln Met Gln Pro Val Gln Thr Pro Phe
            180                 185                 190

Gly Val Val Thr Phe Leu Gln Ile Val Gly Val Cys Thr Glu Glu Leu
        195                 200                 205

His Ser Ala Gln Gln Trp Asn Gly Gln Gly Ile Leu Glu Leu Leu Arg
210                 215                 220

Thr Val Pro Ile Ala Gly Gly Pro Trp Leu Ile Thr Asp Met Arg Arg
225                 230                 235                 240

Gly Glu Thr Ile Phe Glu Ile Asp Pro His Leu Gln Glu Arg Val Asp
                245                 250                 255

Lys Gly Ile Glu Thr Asp Gly Ser Asn Leu Ser Gly Val Ser Ala Lys
            260                 265                 270

Cys Ala Trp Asp Asp Leu Ser Arg Pro Pro Glu Asp Asp Glu Asp Ser
        275                 280                 285

Arg Ser Ile Cys Ile Gly Thr Gln Pro Arg Arg Leu Ser Gly Lys Asp
290                 295                 300

Thr Glu Gln Ile Arg Glu Thr Leu Arg Arg Gly Leu Glu Ile Asn Ser
305                 310                 315                 320

Lys Pro Val Leu Pro Pro Ile Asn Pro Gln Arg Gln Asn Gly Leu Ala
                325                 330                 335

His Asp Arg Ala Pro Ser Arg Lys Asp Ser Leu Glu Ser Asp Ser Ser
            340                 345                 350

Thr Ala Ile Ile Pro His Glu Leu Ile Arg Thr Arg Gln Leu Glu Ser
        355                 360                 365

Val His Leu Lys Phe Asn Gln Glu Ser Gly Ala Leu Ile Pro Leu Cys
370                 375                 380

Leu Arg Gly Arg Leu Leu His Gly Arg His Phe Thr Tyr Lys Ser Ile
385                 390                 395                 400

Thr Gly Asp Met Ala Ile Thr Phe Val Ser Thr Gly Val Glu Gly Ala
                405                 410                 415

Phe Ala Thr Glu Glu His Pro Tyr Ala Ala His Gly Pro Trp Leu Gln
            420                 425                 430

Ile Leu Leu Thr Glu Glu Phe Val Glu Lys Met Leu Glu Asp Leu Glu
        435                 440                 445

Asp Leu Thr Ser Pro Glu Glu Phe Lys Leu Pro Lys Glu Tyr Ser Trp
450                 455                 460

Pro Glu Lys Lys Leu Lys Val Ser Ile Leu Pro Asp Val Val Phe Asp
465                 470                 475                 480

Ser Pro Leu His
```